(12) United States Patent
Alley et al.

(10) Patent No.: US 8,574,907 B2
(45) Date of Patent: Nov. 5, 2013

(54) METHODS AND COMPOSITIONS FOR MAKING ANTIBODIES AND ANTIBODY DERIVATIVES WITH REDUCED CORE FUCOSYLATION

(75) Inventors: Stephen C. Alley, Bothell, WA (US); Scott C. Jeffrey, Bothell, WA (US); Django Sussman, Bothell, WA (US); Dennis R. Benjamin, Bothell, WA (US); Brian Toki, Bothell, WA (US); Patrick J. Burke, Bothell, WA (US)

(73) Assignee: Seattle Genetics, Inc., Bothell, WA (US)

( * ) Notice: Subject to any disclaimer, the term of this patent is extended or adjusted under 35 U.S.C. 154(b) by 0 days.

(21) Appl. No.: 13/405,143

(22) Filed: Feb. 24, 2012

(65) Prior Publication Data
US 2012/0183997 A1 Jul. 19, 2012

Related U.S. Application Data

(62) Division of application No. 12/434,533, filed on May 1, 2009, now Pat. No. 8,163,551.

(60) Provisional application No. 61/107,289, filed on Oct. 21, 2008, provisional application No. 61/092,700, filed on Aug. 28, 2008, provisional application No. 61/050,173, filed on May 2, 2008.

(51) Int. Cl.
*C12N 5/00* (2006.01)

(52) U.S. Cl.
USPC .......................................................... 435/405

(58) Field of Classification Search
None
See application file for complete search history.

(56) References Cited

U.S. PATENT DOCUMENTS

| | | | |
|---|---|---|---|
| 4,407,817 | A | 10/1983 | Chan |
| 5,461,143 | A | 10/1995 | Wong et al. |
| 5,595,976 | A | 1/1997 | Billington et al. |
| 5,770,407 | A | 6/1998 | Wong et al. |
| 5,945,404 | A | 8/1999 | Sugai et al. |
| 6,075,134 | A | 6/2000 | Bertozzi et al. |
| 6,458,937 | B1 | 10/2002 | Bertozzi et al. |
| 6,936,701 | B2 | 8/2005 | Bertozzi et al. |
| 7,335,500 | B2 | 2/2008 | Wong et al. |
| 7,351,408 | B2 | 4/2008 | Bertozzi et al. |
| 7,968,687 | B2 | 6/2011 | McDonagh et al. |
| 2004/0132140 | A1 | 7/2004 | Satoh et al. |
| 2006/0009400 | A1 | 1/2006 | Eckhaerdt et al. |
| 2006/0246456 | A1 | 11/2006 | Tsuchiya et al. |
| 2007/0190597 | A1 | 8/2007 | Agnew et al. |
| 2007/0249014 | A1 | 10/2007 | Agnew et al. |
| 2008/0026943 | A1 | 1/2008 | Fischer et al. |
| 2008/0166756 | A1 | 7/2008 | Tsuchiya et al. |
| 2011/0003338 | A1 | 1/2011 | Bayer et al. |

FOREIGN PATENT DOCUMENTS

| | | |
|---|---|---|
| EP | 1 676 910 A1 | 7/2006 |
| WO | WO 98/25940 A1 | 6/1998 |
| WO | WO 2004/033651 A2 | 4/2004 |
| WO | WO 2004/091499 A2 | 10/2004 |
| WO | WO 2004/099231 A2 | 11/2004 |
| WO | WO 2007/048122 A2 | 4/2007 |
| WO | WO 2007/111952 A2 | 10/2007 |
| WO | WO 2008/052030 A2 | 5/2008 |

OTHER PUBLICATIONS

Gonzalez et al., "Fragmentation of carbohydrate anomeric alkoxy radicals: A mew synthesis of chiral 1-halo-1-iodo Alditols," Chemistry-A European Journal, 2003, vol. 9, No. 23, pp. 5800-5809.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," Journal of Biological Chemistry, 2003, vol. 278, No. 5, pp. 3466-3473.
Supplementary European Search Report, Oct. 2, 2012, EP application No. 09 73 9983, 2 pages.
Albermann et al. "Preparative Synthesis of GDP-β-L-Fucose by Recombinant Enzymes From Enterobacterial Sources," *Glycobiology*, 2000, vol. 10, No. 9, pp. 875-881.
Alton et al. "Direct Utilization of Mannose for Mammalian Glycoprotein Biosynthesis," *Glycobiology*, 1998, vol. 8, No. 3, pp. 285-295.
Baisch et al. "Synthetic Potential of Cloned Fucosyl-Transferase III and VI," *Bioorganic & Medicinal Chemistry Letters*, 1997, vol. 7, No. 19, pp. 2447-2450.
Barbin, K. et al., "Influence of Variable N-Glycosylation on the Cytolytic Potential of Chimeric CD19 Antibodies," *J. Immunother.*, Mar./Apr. 2006, vol. 29, No. 2, pp. 122-133.
Baskin et al. "Bioorthogonal Click Chemistry: Covalent Labeling in Living Systems," *QSAR Comb. Sci.*, 2007, vol. 26, No. 11-12, pp. 1211-1219.
Beacham et al. "Inhibition of Fucosyl Transferase and Fucosidase by a Rigid Bicyclic Mimic of α-L-Fucose," *Tetrahedron Letters*, 1998, vol. 39, pp. 151-154.
Becker et al. "Fucose: Biosynthesis and Biological Function in Mammals," *Glycobiology*, 2003, vol. 13, No. 7, pp. 41R-53R.
Braun et al. "Mechanism-Based Inhibition of Yeast α-Glucosidase and Human Pancreatic α-Amylase by a New Class of Inhibitors," *The Journal of Biological Chemistry*, 1995, vol. 270, No. 45, pp. 26778-26781.
Brown et al. "Glycan Antagonists and Inhibitors: A Fount for Drug Discovery," *Critical Reviews in Biochemistry and Molecular Biology*, 2007, vol. 42, pp. 481-515.
Burkart et al. "Chemo-Enzymatic Synthesis of Fluorinated Sugar Nucleotide: Useful Mechanistic Probes for Glycosyltransferases," *Bioorganic & Medicinal Chemistry*, 2000, vol. 8, pp. 1937-1946.
Butters et al. "Molecular Requirements of Imino Sugars for the Selective Control of N-Linked Glycosylation and Glycosphingolipid Biosynthesis," *Tetrahedron: Asymmetry*, 2000, vol. 11, pp. 113-124.
Cai et al. "Synthesis of Carbocyclic Analogs of Guanosine 5'-(.Beta.-I-Fucopyranosyl Diphosphate) (GDP-Fucose) as Potential Inhibitors of Fucosyltransferases," *J. Org. Chem.*, 1992, vol. 57, pp. 6693-6696.

(Continued)

*Primary Examiner* — Michail Belyavskyi
(74) *Attorney, Agent, or Firm* — Kilpatrick Townsend & Stockton LLP

(57) ABSTRACT

The invention provides methods and compositions for preparing antibodies and antibody derivatives with reduced core fucosylation.

27 Claims, 9 Drawing Sheets

(56) References Cited

OTHER PUBLICATIONS

Calderón et al. "Structure/Activity Relationship of Carba- and C-Fucopyranosides as Inhibitors of an α1,6-Fucosyltransferase by Molecular Modeling and Kinetic Studies," *Letters in Organic Chemistry*, 2005, vol. 2, pp. 247-251.

Clark et al. "Expression of Human α-L-Fucosyltransferase Gene Homologs in Monkey Kidney COS Cells and Modification of Potential Fucosyltransferase Acceptor Substrates by an Endogenous Glycosidase," *Glycobiology*, 1999, vol. 9, No. 2, pp. 191-202.

Codelli et al. "Second-Generation Difluorinated Cyclooctynes for Copper-Free Click Chemistry," *J. Am. Chem. Soc.*, 2008, vol. 130, pp. 11486-11493.

Compain et al. "Carbohydrate Mimetics-Based Glycosyltransferase Inhibitors," *Bioorganic & Medicinal Chemistry*, 2001, vol. 9, pp. 3077-3092.

Compain et al. "Design, Synthesis and Biological Evaluation of Iminosugar-Based Glycosyltransferase Inhibitors," *Current Topics in Medicinal Chemistry*, 2003, vol. 3, pp. 541-560.

Derossi et al. "Ablation of Mouse Phosphomannose Isomerase (*Mpi*) Causes Mannose 6-Phosphate Accumulation, Toxicity, and Embryonic Lethality," *The Journal of Biological Chemistry*, 2006, vol. 281, No. 9, pp. 5916-5927.

Ferrara et al. "The Carbohydrate at FcγRIIIa Asn-162—An Element Required for High Affinity Binding to Non-Fucosylated IgG Glycoforms," *The Journal of Biological Chemistry*, 2006, vol. 281, No. 8, pp. 5032-5036.

Fessner et al. "Enzymes in Organic Synthesis, 15 Short Enzymatic Synthesis of L-Fucose Analogs," *Eur. J. Org. Chem.*, 2000, pp. 125-132.

Galan et al. "The design and Synthesis of a Selective Inhibitor of Fucosyltransferase VI," *Org. Biomol. Chem.*, 2004, vol. 2, pp. 1376-1380.

Gamblin et al. "Glycoprotein Synthesis: An Update," *Chem. Rev.*, 2009, vol. 109, pp. 131-163.

Goon et al. "Metabolic Substrate Engineering as a Tool for Glycobiology," *Journal of Carbohydrate Chemistry*, 2002, vol. 21, No. 7, pp. 943-977.

Gosselin et al. "A Continuous Spectrophotometric Assay for Glycosyltransferases," *Analytical Biochemistry*, 1994, vol. 220, pp. 92-97.

Gross et al. "Inhibition of Protein *N*-Glycosylation by 2-Deoxy-2-Fluoro-D-Galactose," *Biochem. J.*, 1992, vol. 285, pp. 821-826.

Grün et al. "Metabolism and Actions of 2-Deoxy-2-Fluoro-D-Galactose in Vivo," *Eur. J. Biochem.*, 1990, vol. 190, pp. 11-19.

Hanson et al. "Probing Glycans With the Copper(I)-Catalyzed [3+2] Azide—Alkyne Cycloaddition," *QSAR Comb. Sci.*, 2007, vol. 26, No. 11-12, pp. 1243-1252.

Hsu, T-L. et al. "Alkynyl sugar analogs for the labeling and visualization of glycoconjugates in cells," *PNAS*, Feb. 20, 2007, vol. 104, No. 8, pp. 2614-2619.

Ichikawa et al. "Chemical-Enzymatic Synthesis and Conformational Analysis of Sialyl Lewis x and Derivatives," *J. Am. Chem. Soc.*, 1992, vol. 114, pp. 9283-9298.

Ihara et al. "Reaction Mechanism and Substrate Specificity for Nucleotide Sugar of Mammalian α1,6-Fucosyltransferase—A Large-Scale Preparation and Characterization of Recombinant Human FUT8," *Glycobiology*, 2006, vol. 16, No. 4, pp. 333-342.

Ihara et al. "Crystal Structure of Mammalian α1,6-fucosyltransferase, FUT8," *Glycobiology*, 2007, vol. 17, No. 5, pp. 455-466.

Iida et al. "Nonfucosylated Therapeutic IgG1 Antibody Can Evade the Inhibitory Effect of Serum Immunoglobulin G on Antibody-Dependent Cellular Cytotoxicity Through Its High Binding to FcγRIIIa," *Clin Cancer Res.*, 2006, vol. 12, No. 9, pp. 2879-2887.

Imai-Nishiya et al. "Double knockdown of α1,6-fucosyltransferase (*FUT8*) and GDP-mannose 4,6-dehydratase (*GMD*) in antibody-producing cells: a new strategy for generating fully non-fucosylated therapeutic antibodies with enhanced ADCC," *BMC Biotechnology*, 2007, vol. 7, p. 84.

International Search Report mailed on Nov. 25, 2009, for International Application No. PCT/US09/42610 filed on May 1, 2009, 4 pages.

Ishiwata et al. "6-[$^{18}$F] Fluoro-L-fucose: A Possible Tracer for Assessing Glycoconjugate Synthesis in Tumors with Positron Emission Tomography," *J. Nucl. Med.*, 1990, vol. 31, pp. 1997-2003.

Jefferis "Glycosylation as a Strategy to Improve Antibody-Based Therapeutics," *Nature Reviews Drug Discovery*, 2009, vol. 8, pp. 227-234.

Jones et al. "Characterization of the Cellular Uptake and Metabolic Conversion of Acetylated N-Acetylmannosamine (ManNAc) Analogues to Sialic Acids," *Biotechnology and Bioengineering*, 2004, vol. 85, No. 4, pp. 394-405.

Kanda et al. "Comparison of Biological Activity Among Nonfucosylated Therapeutic IgG1 Antibodies with Three Different *N*-Linked Fc Oligosaccharides: The High-Mannose, Hybrid, and Complex Types," *Glycobiology*, 2006, vol. 17, No. 1, pp. 104-118.

Kanda et al. "Establishment of a GDP-Mannose 4,6-Dehydratase (*GMD*) Knockout Host Cell Line: A New Strategy for Generating Completely Non-Fucosylated Recombinant Therapeutics," *Journal of Biotechnology*, 2007, vol. 130, pp. 300-310.

Kim et al. "Characterization of the Metabolic Flux and Apoptotic Effects of O-Hydroxyl- and *N*-Acyl-modified *N*-Acetylmannosamine Analogs in Jurkat Cells," *The Journal of Biological Chemistry*, 2004, vol. 279, No. 18, pp. 18342-18352.

Laughlin et al. "Metabolic Labeling of Glycans with Azido Sugars and Subsequent Glycan-Profiling and Visualization via Staudinger Ligation," *Nature Protocols*, 2007, vol. 2, No. 11, pp. 2930-2944.

Laughlin et al. "Imaging the Glycome," *PNAS*, 2009, vol. 106, No. 1, pp. 12-17.

Lee et al. "Analogs of Cell Surface Carbohydrates. Synthesis of D-Galactose Derivatives Having an Ethynyl, Vinyl or Epoxy Residue at C-5," *Carbohydrate Research*, 1988, vol. 176, pp. 59-72.

Lee et al. "A Potent and Highly Selective Inhibitor of Human α-1,3-Fucosyltransferase via Click Chemistry," *J. Am. Chem. Soc.*, 2003, vol. 125, pp. 9588-9589.

Lim et al. "Glycosylation Profiling of a Therapeutic Recombinant Monoclonal Antibody with Two N-Linked Glycosylation Sites Using Liquid Chromatography Coupled to a Hybrid Quadrupole Time-of-Flight Mass Spectrometer," *Analytical Biochemistry*, 2008, vol. 375, pp. 163-172.

Luchansky et al. "Expanding the Diversity of Unnatural Cell-Surface Sialic Acids," *ChemBioChem*, 2004, vol. 5, pp. 371-374.

Maeda et al. "Fret-Based Direct and Continuous Monitoring of Human Fucosyltransferases Activity: An Efficient synthesis of Versatile GDP-L-Fucose Derivatives from Abundant D-Galactose," *Chem. Eur. J.*, 2008, vol. 14, pp. 478-487.

Matsumura et al. "Carbohydrate Binding Specificity of a Fucose-specific Lectin From *Aspergillus oryzae*—A Novel Probe for Core Fucose," *The Journal of Biological Chemistry*, 2007, vol. 282, No. 21, pp. 15700-15708.

May, Jr., et al. "Synthesis and Biological Activity of Potential Antimetabolites of L-Fucose," *Journal of Medicinal Chemistry*, 1979, vol. 22, No. 8, pp. 971-976.

Mori et al. "Engineering Chinese Hamster Ovary Cells to Maximize Effector Function of Produced Antibodies Using FUT8 siRNA," *Biotechnology and Bioengineering*, 2004, vol. 88, No. 7, pp. 901-908.

Mori et al. "Non-Fucosylated Therapeutic Antibodies: The Next Generation of Therapeutic Antibodies," *Cytotechnology*, 2007, vol. 55, pp. 109-114.

Murray et al. "Mechanism of Human α-1,3-Fucosyltransferase V: Glycosidic Cleavage Occurs Prior to Nucleophilic Attack," *Biochemistry*, 1997, vol. 36, pp. 823-831.

Niittymäki "GDP-L-Fucose: Synthesis and Role in Inflammation," Academic Dissertation 2007, Department of Bacteriology and Immunology, Haartman Institute and Biomedicum Helsinki and Division of Biochemistry, Department of Biological and Environmental Sciences, Faculty of Biosciences University of Helsinki and Glycoscience Graduate School.

(56) References Cited

OTHER PUBLICATIONS

Niittymaki et al. "Cloning and Expression of Murine Enzymes Involved in the Salvage Pathway of GDP-L-Fucose L-Fucokinase and GDP-L-Fucose Pyrophosphorylase," *Eur. J. Biochem.*, 2004, vol. 271, pp. 78-86.
Norris et al. "Inhibition Kinetics of Carba- and C-fucosyl Analogues of GDP-Fucose Against Fucosyltransferase v: Implication for the Reaction Mechanism," *Bioorganic & Medicinal Chemistry Letters*, 2004, vol. 14, pp. 571-573.
Omasa et al. "Decrease in Antithrombin III Fucosylation by Expressing GDP-Fucose Transporter siRNA in Chinese Hamster Ovary Cells," *Journal of Bioscience and Bioengineering*, 2008, vol. 106, No. 2, pp. 168-173.
Pan et al. "Castanospermine Inhibits the Processing of the Oligosaccharide Portion of the Influenza Viral Hemagglutinin," *Biochemistry*, 1983, vol. 22, pp. 3975-3984.
Panneerselvam et al. "Human Fibroblasts Prefer Mannose over Glucose as a Source of Mannose for N-Glycosylation," *The Journal of Biological Chemistry*, 1997, vol. 272, No. 37, pp. 23123-23129.
Papac et al. "A High-Throughput Microscale Method to Release N-Linked Oligosaccharides From Glycoproteins for Matrix-Assisted Laser Desorption/Ionization Time-of-Flight Mass Spectrometric Analysis," *Glycobiology*, 1998, vol. 8, No. 5, pp. 445-454.
Park et al. "Characterization and Role of Fucose Mutarotase in Mammalian Cells," *Glycobiology*, 2007, vol. 17, No. 9, pp. 955-962.
Park et al. "Chemical Tools for Functional Studies of Glycans," *Chem. Soc. Rev.*, 2008, vol. 37, pp. 1579-1591.
Peipp et al. "Antibody Fucosylation Differentially Impacts Cytotoxicity Mediated by NK and PMN Effector Cells," wwwbloodjournal.org at University of Washington on Jun. 20, 2008.
Prescher et al., "Chemistry in Living Systems," *Nature Chemical Biology*, 2005, vol. 1, No. 1, pp. 13-21.
Qiao et al. "Synergistic Inhibition of Human α-1,3-Fucosyltransferase V," *J. Am. Chem. Soc.*, 1996, vol. 118, pp. 7653-7662.
Rabuka et al. "A Chemical Reporter Strategy to Probe Glycoprotein Fucosylation," *J. Am. Chem. Soc.*, 2006, vol. 28, pp. 12078-12079.
Sampathkumar et al. "Metabolic Installation of Thiols into Sialic Acid Modulates Adhesion and Stem Cell Biology," *Nature Chemical Biology*, 2006, vol. 2, No. 3, pp. 149-152.
Sawa et al. "Glycoproteomic Probes for Fluorescent Imaging of Fucosylated Glycans in Vivo," *PNAS*, 2006, vol. 103, No. 33, pp. 12371-12376.
Saxon et al. "Investigating Cellular Metabolism of Synthetic Azidosugars with the Staudinger Ligation," *J. Am. Chem. Soc.*, 2002, vol. 124, pp. 14893-14902.
Schuster et al. "Improved Effector Functions of a Therapeutic Monoclonal Lewis Y-Specific Antibody by Glycoform Engineering," *Cancer Res.*, 2005, vol. 65, No. 17, pp. 7934-7941.
Staňková, J. et al., "Fucose-Activated Killer (FAK) Cells: Anomalous Killers With Augmented Cytotoxic Activity," *The Journal of Immunology*, Dec. 6, 1985, vol. 135, No. 6, pp. 3718-3728.
Sturla et al. "Expression, Purification and Characterization of GDP-D-Mannose 4,6-Dehydratase From *Escherichia coli*," *FEBS Letters*, 1997, vol. 412, pp. 126-130.
Sufrin et al. "Halogenated L-Fucose and D-Galactose Analogs: Synthesis and Metabolic Effects," *J. Med. Chem.*, 1980, vol. 23, No. 2, pp. 143-149.
Takahashi et al. "A Sequence Motif Involved in the Donor Substrate Binding by α1,6-fucosyltransferase: the Role of the Conserved Residues," *Glycobiology*, 2000, vol. 10, No. 5, pp. 503-510.
Tanaka et al. "Design and Synthesis of Peptide Mimetics of GDP-Fucose: Targeting Inhibitors of Fucosyltransferases," *Synlett*, 2004, No. 2, pp. 243-246.
Tarling et al. "Identification of the Catalytic Nucleophile of the Family 29 α-L-Fucosidase from *Thermotoga maritima* through Trapping of a Covalent Glycosyl-Enzyme Intermediate and Mutagenesis," *The Journal of Biological Chemistry*, 2003, vol. 278, No. 48, pp. 47394-47399.
Ulgar et al. "New *N*-Alkylsulfonamides and Alkyl Sulfonates Derived From 6-C-Sulfosugars," *Tetrahedron*, 2002, vol. 58, pp. 7967-7973.
Vocadlo et al. "A Chemical Approach for Identifying *O*-GlcNAc-Modified Proteins in Cells," *PNAS*, 2003, vol. 100, No. 16, pp. 9116-9121.
Vogel et al. "Galacturonate aus Acetyl- und Isopropyliden-D-Galactopyranosen," *Journal f. prakt. Chemie. Band*, 1990, vol. 332, No. 1, pp. 28-36, translation of Abstract only.
Vogel et al. "Synthesis of C-Glycosidic Galacturopates Suitable as Glycosyl Acceptors," *Polish J. Chem.*, 2005, vol. 79, pp. 251-265.
Von Ahsen et al. "A Miniaturized High-Throughput Screening Assay for Fucosyltransferase VII," *Analytical Biochemistry*, 2008, vol. 372, pp. 96-105.
Wang et al. "Efficient Glycoengineering of GM3 on Melanoma Cell and Monoclonal Antibody-Mediated Selective Killing of the Glycoengineered Cancer Cell," *Bioorganic & Medicinal Chemistry*, 2007, vol. 15, pp. 7561-7567.
Watt et al. "Site-Specific Glycosylation of an Aglycosylated Human IgG1-Fc Antibody Protein Generates Neoglycoproteins with Enhanced Function," *Chemistry & Biology*, 2003, vol. 10, 807-814.
Wilkinson et al. "Click Chemistry in Carbohydrate Based Drug Development and Glycobiology," In: Drug Design Research Perspectives, Editor: Stanley P. Kaplan, Nova Science Publishers, Inc. 2007, pp. 57-102.
Winterbourne et al. "2-Deoxy-2-Fluoro-L-Fucose and Its Effect on L-[1-$^{14}$C] Fucose Utilization in Mammalian Cells," *Biochemical and Biophysical Research Communications*, 1979, vol. 87, pp. 989-992.
Wright et al. "Effect of Altered $C_H2$-associated Carbohydrate Structure on the Functional Properties and in Vivo Fate of Chimeric Mouse-Human Immunoglobulin G1," *J. Exp. Med.*, 1994, vol. 180, pp. 1087-1096.
Wright et al. "In Vivo Trafficking and Catabolism of IgG1 Antibodies with Fc Associated Carbohydrates of Differing Structure," *Glycobiology*, 2000, vol. 10, No. 12, pp. 1347-1355.
Wrodnigg et al. "Natural and Synthetic Iminosugars as Carbohydrate Processing Enzyme Inhibitors for Cancer Therapy," *Anti-Cancer Agents in Medicinal Chemistry*, 2008, vol. 8, pp. 77-85.
Yamaguchi et al. "Glycoform-Dependent Conformational Alteration of the Fc Region of Human Immunoglobulin G1 as Revealed by NMR Spectroscopy," *Biochimica et Biophysica Acta*, 2006, vol. 1760, pp. 693-700.
Yurchenco et al. "Fucosyl-Glycoprotein and Precursor Pools in HeLa Cells," *Biochemistry*, 1975, vol. 14, No. 14, 3107-3114.
Yurchencol et al. "Equilibration of Fucosyl Glycoprotein Pools in HeLa Cells," *Biochemistry*, 1977, vol. 16, No. 5, pp. 944-953.
Zeng et al. "High-Efficiency Labeling of Sialylated Glycoproteins on Living Cells," *Nature Methods*, 2009, vol. 6, No. 3, pp. 207-209.
Zeng et al. "High-Efficiency Labeling of Sialylated Glycoproteins on Living Cells," *Nature Methods*, 2009, vol. 6, No. 3, pp. 1S-13S.
Zhao et al. "Deletion of Core Fucosylation on α3β1 Integrin Down-Regulates Its Functions," *The Journal of Biological Chemistry*, 2006, vol. 281, No. 50, pp. 38343-38350.
Zhou et al. "Development of a Simple and Rapid Method for Producing Non-Fucosylated Oligomannose Containing Antibodies With Increased Effector Function," *Biotechnology and Bioengineering*, 2008, vol. 99, No. 3, pp. 652-665.

A.

B.

A.

D.

A.

B.

METHODS AND COMPOSITIONS FOR MAKING ANTIBODIES AND ANTIBODY DERIVATIVES WITH REDUCED CORE FUCOSYLATION

CROSS-REFERENCES TO RELATED APPLICATIONS

This application claims the benefit of U.S. Ser. No. 61/050,173 filed May 2, 2008; U.S. Ser. No. 61/092,700 filed Aug. 28, 2008; and U.S. Ser. No. 61/107,289 filed Oct. 21, 2008, the contents of each are incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Recombinant therapeutic proteins are produced by many different methods. One preferred method is production of recombinant proteins from mammalian host cell lines. Cell lines, such as Chinese Hamster Ovary (CHO) cells, are engineered to express the therapeutic protein of interest. Different cell lines have advantages and disadvantages for recombinant protein production, including protein characteristics and productivity. Selection of a cell line for commercial production often balances the need for high productivity with the ability to deliver consistent product quality with the attributes required of a given product. One important class of therapeutic recombinant proteins that require consistent, high quality characteristics and high titer processes are monoclonal antibodies.

Monoclonal antibodies produced in mammalian host cells can have a variety of post-translational modifications, including glycosylation. Monoclonal antibodies, such as IgG1s, have an N-linked glycosylation site at asparagine 297 (Asn297) of each heavy chain (two per intact antibody). The glycans attached to Asn297 on antibodies are typically complex biantennary structures with very low or no bisecting N-acetylglucosamine (bisecting GlcNAc) with low amounts of terminal sialic acid and variable amounts of galactose. The glycans also usually have high levels of core fucosylation. Reduction of core fucosylation in antibodies has been shown to alter Fc effector functions, in particular Fcgamma receptor binding and ADCC activity. This observation has lead to interest in the engineering cell lines so they produce antibodies with reduced core fucosylation.

Methods for engineering cell lines to reduce core fucosylation included gene knock-outs, gene knock-ins and RNA interference (RNAi). In gene knock-outs, the gene encoding FUT8 (alpha 1,6-fucosyltransferase enzyme) is inactivated. FUT8 catalyzes the transfer of a fucosyl residue from GDP-fucose to position 6 of Asn-linked (N-linked) GlcNac of an N-glycan. FUT8 is reported to be the only enzyme responsible for adding fucose to the N-linked biantennary carbohydrate at Asn297. Gene knock-ins add genes encoding enzymes such as GNTIII or a golgi alpha mannosidase II. An increase in the levels of such enzymes in cells diverts mono-clonal antibodies from the fucosylation pathway (leading to decreased core fucosylation), and having increased amount of bisecting N-acetylglucosamines. RNAi typically also targets FUT8 gene expression, leading to decreased mRNA transcript levels or knock out gene expression entirely.

Alternatives to engineering cell lines include the use of small molecule inhibitors that act on enzymes in the glycosylation pathway. Inhibitors such as catanospermine act early in the glycosylation pathway, producing antibodies with immature glycans (e.g., high levels of mannose) and low fucosylation levels. Antibodies produced by such methods generally lack the complex N-linked glycan structure associated with mature antibodies.

In contrast, the present invention provides small molecule fucose analogs for use in producing recombinant antibodies that have complex N-linked glycans, but have reduced core fucosylation.

SUMMARY OF THE INVENTION

The invention provides methods and compositions for preparing antibodies and antibody derivatives with reduced core fucosylation. The methods and compositions are premised in part on the unexpected results presented in the Examples showing that culturing host cells, expressing an antibody or antibody derivative, in the presence of a fucose analog (having formula I, II, III, IV, V or VI) produces an antibody having reduced core fucosylation (i.e., reduced fucosylation of N-acetylglucosamine of the complex N-glycoside-linked sugar chains bound to the Fc region through the N-acetylglucosamine of the reducing terminal of the sugar chains). Such antibodies and antibody derivatives may exhibit increased effector function (ADCC), as compared with antibodies or antibody derivatives produced from such host cells cultured in the absence of the fucose analog.

In another aspect, compositions of antibodies and antibody derivatives are provided. The antibodies and antibody derivatives can be produced by the methods described herein.

In another aspect, fucose analogs are provided. The fucose analogs can be added to mammalian cell culture media to inhibit or reduce core fucosylation. Also provided is cell culture media comprising an effective amount of such a fucose analog(s).

These and other aspects of the present invention may be more fully understood by reference to the following detailed description, non-limiting examples of specific embodiments, and the appended figures.

BRIEF DESCRIPTION OF THE DRAWINGS

FIG. 3A shows binding competition for human Fcγ receptor (CD16)-expressing cells. FIG. 3B shows binding competition for murine Fcγ receptor (CD16)-expressing cells.

FIG. 4A: anti-CD70 antibody. FIG. 4B: anti-CD19 antibody. FIG. 4C: anti-CD30 antibody. FIG. 4D: anti-CD33 antibody.

DETAILED DESCRIPTION OF THE INVENTION

Definitions

Figure 1:
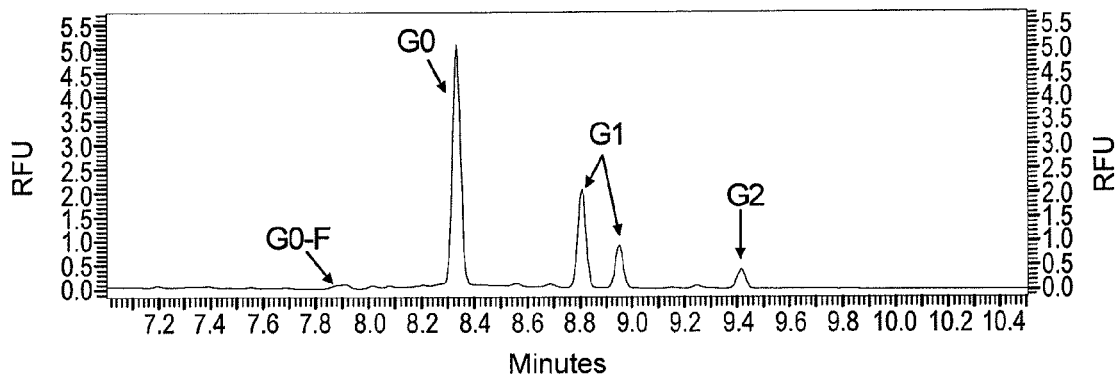
FIG. 1 shows an analysis (electropherograms) of glycans isolated from an anti-CD70 antibody (h1F6) produced from control (A) and alkynyl fucose peracetate (AlkF)-treated host cells (B and C). The panels show the identity and relative distribution of glycans. "G0" refers to the carbohydrate structure where there is no galactose at the two non-reducing termini. "G1" refers to a carbohydrate structure where one of the non-reducing termini has a galactose (a mixture of two isomers). "G2" refers to a carbohydrate structure where both of the non-reducing termini have a galactose. "G0-F" refers to a carbohydrate structure where there is no galactose at either of the two non-reducing termini and there is no core fucosylation. Panel 1A: glycans isolated from control (untreated) h1F6 antibody. Panel 1B: glycans isolated from h1F6 antibodies expressed in the presence of 50 μm alkynyl fucose peracetate. Panel 1C: glycans isolated from h1F6 antibodies expressed in the presence of 50 μm alkynyl fucose peracetate and treated with β-galactosidase to remove galactose from the G1 and G2 glycans.
Figure 1:
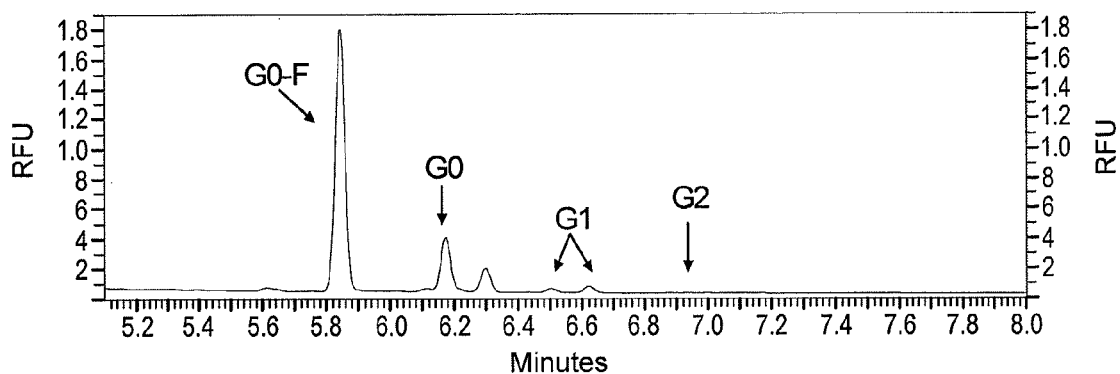
Figure 1:
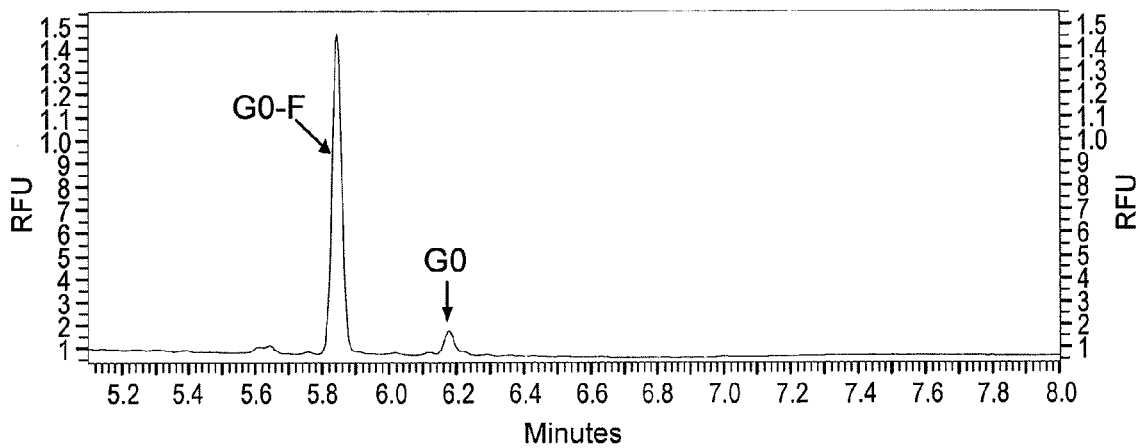

The term "antibody" refers to (a) immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., CD70) and an Fc domain comprising a complex N-glycoside-linked sugar chain(s), or (b) conservatively substituted derivatives of such immunoglobulin polypeptides or fragments that immunospecifically bind to the antigen (e.g., CD70). Antibodies are generally described in, for example, Harlow & Lane, Antibodies: *A Laboratory Manual* (Cold Spring Harbor Laboratory Press, 1988). Unless otherwise apparent from the context, reference to an antibody also includes antibody derivatives as described in more detail below.

An "antibody derivative" means an antibody, as defined above (including an antibody fragment), or Fc domain or region of an antibody comprising a complex N-glycoside linked sugar chain, that is modified by covalent attachment of a heterologous molecule such as, e.g., by attachment of a heterologous polypeptide (e.g., a ligand binding domain of heterologous protein), or by glycosylation (other than core fucosylation), deglycosylation (other than non-core fucosylation), acetylation, phosphorylation or other modification not normally associated with the antibody or Fc domain or region.

The term "monoclonal antibody" refers to an antibody that is derived from a single cell clone, including any eukaryotic or prokaryotic cell clone, or a phage clone, and not the method by which it is produced. Thus, the term "monoclonal antibody" is not limited to antibodies produced through hybridoma technology.

The term "Fc region" refers to the constant region of an antibody, e.g., a $C_H1$-hinge-$C_H2$-$C_H3$ domain, optionally having a $C_H4$ domain, or a conservatively substituted derivative of such an Fc region.

The term "Fc domain" refers to the constant region domain of an antibody, e.g., a $C_H1$, hinge, $C_H2$, $C_H3$ or $C_H4$ domain, or a conservatively substituted derivative of such an Fc domain.

An "antigen" is a molecule to which an antibody specifically binds.

The terms "specific binding" and "specifically binds" mean that the antibody or antibody derivative will bind, in a highly selective manner, with its corresponding target antigen and not with the multitude of other antigens. Typically, the antibody or antibody derivative binds with an affinity of at least about $1 \times 10^{-7}$ M, and preferably $10^{-8}$ M to $10^{-9}$ M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than the predetermined antigen or a closely-related antigen.

The teams "inhibit" or "inhibition of" means to reduce by a measurable amount, or to prevent entirely.

As used herein, "alkynyl fucose peracetate" refers to any or all forms of alkynyl fucose (5-ethynylarabinose) with acetate groups on positions $R^{1-4}$ (see formula I and II, infra), including 6-ethynyl-tetrahydro-2H-pyran-2,3,4,5-tetrayl tetraacetate, including the (2S,3S,4R,5R,6S) and (2R,3S,4R,5R,6S) isomers, and 5-((S)-1-hydroxyprop-2-ynyl)-tetrahydrofuran-2,3,4-triyl tetraacetate, including the (2S,3S,4R,5R) and (2R,3S,4R,5R) isomers, and the aldose form, unless otherwise indicated by context. The terms "alkynyl fucose triacetate", "alkynyl fucose diacetate" and "alkynyl fucose monoacetate" refer to the indicated tri-, di- and mono-acetate forms of alkynyl fucose, respectively.

Unless otherwise indicated by context, the term "alkyl" refers to a substituted or unsubstituted saturated straight or branched hydrocarbon having from 1 to 20 carbon atoms (and all combinations and subcombinations of ranges and specific numbers of carbon atoms therein), with from 1 to 3, 1 to 8 or 1 to 10 carbon atoms being preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, can be optionally substituted with one or more groups, preferably 1 to 3 groups (and any additional substituents selected from halogen), including, but not limited to: halogen, —O—($C_1$-$C_8$ alkyl), —O—($C_2$-$C_8$ alkenyl), —O—($C_2$-$C_8$ alkynyl), aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —NH$_2$, —NH(R'), —N(R')$_2$ and —CN; where each R' is independently selected from —H, —C$_1$-C$_8$ alkyl, —C$_2$-C$_8$ alkenyl, —C$_2$-C$_8$ alkynyl, or aryl. In some embodiments, the —O—(C$_1$-C$_8$ alkyl), —O—(C$_2$-C$_8$ alkenyl), —O—(C$_2$-C$_8$ alkynyl), aryl, and R' groups can be further substituted. Such further substituents include, for example, —C$_1$-C$_8$ alkyl, —C$_2$-C$_8$ alkenyl, —C$_2$-C$_8$ alkynyl, halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —NH$_2$, —NH(R"), —N(R")$_2$ and —CN, where each R" is independently selected from H, —C$_1$-C$_8$ alkyl, —C$_2$-C$_8$ alkenyl, —C$_2$-C$_8$ alkynyl, or aryl wherein said further substituents are preferably unsubstituted. In some embodiments, the —O—(C$_1$-C$_8$ alkyl), —O—(C$_2$-C$_8$ alkenyl), —O—(C$_2$-C$_8$ alkynyl), aryl, and R' groups are not further substituted.

Unless otherwise indicated by context, the terms "alkenyl" and "alkynyl" refer to substituted or unsubstituted straight and branched carbon chains having from 2 to 20 carbon atoms (and all combinations and subcombinations of ranges and specific numbers of carbon atoms therein), with from 2 to 3, 2 to 4, 2 to 8 or 2 to 10 carbon atoms being preferred. An alkenyl chain has at least one double bond in the chain and an alkynyl chain has at least one triple bond in the chain. Examples of alkenyl groups include, but are not limited to, ethylene or vinyl, allyl, -1 butenyl, -2 butenyl, -isobutylenyl, -1 pentenyl, -2 pentenyl, 3-methyl-1-butenyl, -2 methyl 2 butenyl, and -2,3 dimethyl 2 butenyl. Examples of alkynyl groups include, but are not limited to, acetylenic, propargyl, acetylenyl, propynyl, -1 butynyl, -2 butynyl, -1 pentynyl, -2 pentynyl, and -3 methyl 1 butynyl.

Alkenyl and alkynyl groups, whether alone or as part of another group, can be optionally substituted with one or more groups, preferably 1 to 3 groups (and any additional substituents selected from halogen), including but not limited to: halogen, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —NH$_2$, —NH(R'), —N(R')$_2$ and —CN; where each R' is independently selected from H, —C$_1$-C$_8$ alkyl, —C$_2$-C alkenyl, —C$_2$-C$_8$ alkynyl, or aryl. In some embodiments, the —O—(C$_1$-C$_8$ alkyl), —O—(C$_2$-C$_8$ alkenyl), —O—(C$_2$-C$_8$ alkynyl), aryl, and R' groups can be further substituted. Such further substituents include, for example, —C$_1$-C$_8$ alkyl, —C$_2$-C$_8$ alkenyl, —C$_2$-C$_8$ alkynyl, halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —NH$_2$, —NH(R"), —N(R")$_2$ and —CN, where each R" is independently selected from H, —C$_1$-C$_8$ alkyl, —C$_2$-C$_8$ alkenyl, —C$_2$-C$_8$ alkynyl, or aryl, wherein said further substituents are preferably unsubstituted. In some embodiments, the —O—(C$_1$-C$_8$ alkyl), —O—(C$_2$-C$_8$ alkenyl), —O—(C$_2$-C$_8$ alkynyl), -aryl, and R' groups are not further substituted.

Unless otherwise indicated by context, the term "alkylene" refers to a substituted or unsubstituted saturated branched or straight chain hydrocarbon radical having from 1 to 20 carbon atoms (and all combinations and subcombinations of ranges and specific numbers of carbon atoms therein), with from 1 to 8 or 1 to 10 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, ocytylene, nonylene, decalene, 1,4-cyclohexylene, and the like.

Alkylene groups, whether alone or as part of another group, can be optionally substituted with one or more groups, preferably 1 to 3 groups (and any additional substituents selected from halogen), including, but not limited to: halogen, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)2$_R$', —S(O)R', —OH, =O, —NH$_2$, —NH(R'), —N(R')$_2$ and —CN; where each R' is independently selected from H, —C$_1$-C$_8$ alkyl, —C$_2$-C$_8$ alkenyl, —C$_2$-C$_8$ alkynyl, or -aryl. In some embodiments, the —O—(C$_1$-C$_8$ alkyl), —O—(C$_2$-C8 alkenyl), —O—(C$_2$-C$_8$ alkynyl), aryl, and R' groups can be further substituted. Such further substituents include, for example, C$_1$-C$_8$ alkyl, —C$_2$-C$_8$ alkenyl, —C$_2$-C$_8$ alkynyl, halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —NH$_2$, —NH(R"), —N(R")$_2$ and —CN, where each R" is independently selected from H, —C$_1$-C$_8$ alkyl, —C$_2$-C$_8$ alkenyl, —C$_2$-C$_8$ alkynyl, or aryl wherein said further substituents are preferably unsubstituted. In some embodiments, the —O—(C$_1$-C$_8$ alkyl), —O—(C$_2$-C$_8$ alkenyl), —O—(C$_2$-C$_8$ alkynyl), -aryl, and R' groups are not further substituted.

Unless otherwise indicated by context, the term "aryl" refers to a substituted or unsubstituted monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to: halogen, —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NO$_2$, —NH2, —NH(R'), —N(R')$_2$ and —CN; where each R' is independently selected from H, —C$_1$-C$_8$ alkyl, —C$_2$-C$_8$ alkenyl, —C$_2$-C$_8$ alkynyl, or aryl. In some embodiments, the C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), aryl and R' groups can be further substituted. Such further substituents include, for example, —C$_1$-C$_8$ alkyl, —C$_2$-C$_8$ alkenyl, —C$_2$-C$_8$ alkynyl, halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —NH$_2$, —NH(R"), —N(R")$_2$ and —CN, where each R" is independently selected from —H, —C$_1$-C$_8$ alkyl, —C$_2$-C$_8$ alkenyl, —C$_2$-C$_8$ alkynyl, or aryl wherein said further substituents are preferably unsubstituted. In some embodiments, the —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), aryl and R' groups are not further substituted.

Unless otherwise indicated by context, the term "heterocycle" refers to a substituted or unsubstituted monocyclic ring system having from 3 to 7, or 3 to 10, ring atoms (also referred to as ring members) wherein at least one ring atom is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocytic heterocycle preferably has 3 to 7 ring members (e.g., 2 to 6 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 82:5566 (1960).

Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, fucosyl, azirdinyl, azetidinyl, oxiranyl, oxetanyl, and tetrahydrofuranyl.

A heterocycle group, whether alone or as part of another group, can be optionally substituted with one or more groups, preferably 1 to 2 groups, including but not limited to: —$C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, —$NH_2$, —NH(R'), —N(R')$_2$ and —CN; where each R' is independently selected from H, —$C_1$-$C_8$ alkyl, —$C_2$-$C_8$ alkenyl, —$C_2$-$C_8$ alkynyl, or -aryl. In some embodiments, the O—($C_1$-$C_8$ alkyl), —O—($C_2$-$C_8$ alkenyl), —O—($C_2$-$C_8$ alkynyl), —$C_1$-$C_8$ alkyl, —$C_2$-$C_8$ alkenyl, —$C_2$-$C_8$ alkynyl, aryl, and R' groups can be further substituted. Such further substituents include, for example, —$C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R'', —OC(O)R'', —C(O)OR'', —C(O)$NH_2$, —C(O)NHR'', —C(O)N(R'')$_2$, —NHC(O)R'', —SR'', —$SO_3$R'', —S(O)$_2$R'', —S(O)R'', —OH, —$NH_2$, —NH(R''), —N(R'')$_2$ and —CN, where each R'' is independently selected from H, —$C_1$-$C_8$ alkyl, —$C_2$-$C_8$ alkenyl, —$C_2$-$C_8$ alkynyl, or aryl wherein said further substituents are preferably unsubstituted. In some embodiments, the —O—($C_1$-$C_8$ alkyl), —O—($C_2$-$C_8$ alkenyl), —O—($C_2$-$C_8$ alkynyl), —$C_1$-$C_8$ alkyl, —$C_2$-$C_8$ alkenyl, —$C_2$-$C_8$ alkynyl, aryl, and R' groups are not substituted.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine. Exemplary carbon bonded heterocycles can include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; and position 4 of a morpholine. Still more typically, nitrogen bonded heterocycles include 1-aziridyl, 1-azetidyl, 1-pyrrolyl, 1-imidazolyl, 1-pyrazolyl, and 1-piperidinyl.

Unless otherwise noted, the term "carbocycle," refers to a substituted or unsubstituted, saturated or unsaturated non-aromatic monocyclic ring system having from 3 to 6 ring atoms (and all combinations and subcombinations of ranges and specific numbers of carbon atoms therein) wherein all of the ring atoms are carbon atoms.

Carbocycle groups, whether alone or as part of another group, can be optionally substituted with, for example, one or more groups, preferably 1 or 2 groups (and any additional substituents selected from halogen), including, but not limited to: halogen, $C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$NH_2$, —NH(R'), —N(R')$_2$ and —CN; where each R' is independently selected from H, —$C_1$-$C_8$ alkyl, —$C_2$-$C_8$ alkenyl, —$C_2$-$C_8$ alkynyl, or aryl. In some embodiments, the —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl and R' groups can be further substituted. Such further substituents include, for example, —$C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R'', —OC(O)R'', —C(O)OR'', —C(O)$NH_2$, —C(O)NHR'', —C(O)N(R'')$_2$, —NHC(O)R'', —SR'', —$SO_3$R'', —S(O)$_2$R'', —S(O)R'', —OH, —$NH_2$, —NH(R''), —N(R'')$_2$ and —CN, where each R'' is independently selected from H, —$C_1$-$C_8$ alkyl, —$C_2$-$C_8$ alkenyl, —$C_2$-$C_8$ alkynyl, or aryl wherein said further substituents are preferably unsubstituted. In some embodiments, the —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), aryl and R' groups are not substituted.

Examples of monocyclic carbocylic substituents include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, cyclooctyl, -1,3-cyclohexadienyl, -1,4-cyclohexadienyl, -1,3-cycloheptadienyl, -1,3,5-cycloheptatrienyl, and -cyclooctadienyl.

When any variable occurs more than one time in any constituent or in any formula, its definition in each occurrence is independent of its definition at every other. Combinations of substituents and/or variables are permissible only if such combinations result in stable compounds.

Unless otherwise indicated by context, a hyphen (-) designates the point of attachment to the pendant molecule. Accordingly, the term "—($C_1$-$C_{10}$ alkylene)aryl" or "—$C_1$-$C_{10}$ alkylene(aryl)" refers to a $C_1$-$C_{10}$ alkylene radical as defined herein wherein the alkylene radical is attached to the pendant molecule at any of the carbon atoms of the alkylene radical and one of the hydrogen atom bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "pharmaceutically acceptable" means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which the antibody or antibody derivative is administered.

The term "biologically acceptable" means suitable for use in the culture of cell lines for the manufacture of antibodies. Exemplary biologically acceptable salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene bis-(2 hydroxy 3-naphthoate)) salts. A biologically acceptable salt may involve the inclusion of another molecule such as an acetate ion, a succinate ion or other counterion. The counterion may be any organic or inorganic moiety that stabilizes the charge on the parent compound. Furthermore, a biologically acceptable salt may have more than one charged atom in its structure. Instances where multiple charged atoms are part of the biologically acceptable salt can have multiple counter ions. Hence, a biologically salt can have one or more charged atoms and/or one or more counterion.

A "biologically acceptable solvate" or "solvate" refer to an association of one or more solvent molecules and a fucose analog. Examples of solvents that form biologically acceptable solvates include, but are not limited to, water, isopropanol, ethanol, methanol, DMSO, ethyl acetate, acetic acid, and ethanolamine.

"Small electron-withdrawing groups" refers to any substituent that has greater electronegativity at the site of substituent attachment than, e.g., a hydrogen atom or hydroxy group or relative to the substituent present in fucose at that site. Generally, the small electron-withdrawing group has 10 or fewer atoms (other than hydrogen) and includes groups such as nitro; cyano and cyanoalkyl (e.g., —CH$_2$CH$_2$CN); halogen; acetylene or other alkynes or halo alkynes (e.g., —C≡CCF$_3$); alkenes or halo alkenes; allenes; carboxylic acids, ester, amides and halo substituted forms thereof; sulfonic and phosphonic acids, esters and amides, and halo substituted forms thereof; haloalkyl groups (e.g., —CF$_3$, —CHF$_2$, —CH$_2$CF$_3$), acyl and haloacyl groups (e.g., —C(O)CH$_3$ and —C(O)CF$_3$); alkylsulfonyl and haloalkylsulfonyl (e.g., —S(O)$_2$alkyl and —S(O)$_2$haloalkyl); aryloxy (e.g, phenoxy and substituted phenoxy); aralkyloxy (e.g, benzyloxy and substituted benzyloxy); and oxiranes. Preferred small electron-withdrawing groups are those having 8, 7 or 6 or fewer atoms (other than hydrogen).

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90% or about 95% w/w purity. Using conventional protein purification techniques, homogeneous peptides of at least 99% w/w can be obtained.

General

The invention provides compositions and methods for preparing antibodies and antibody derivatives with reduced core fucosylation. The methods are premised in part on the unexpected results presented in the Examples showing that culturing host cells, expressing an antibody or antibody derivative of interest, in culture media comprising a fucose analog produces an antibody or antibody derivative having reduced core fucosylation. As used herein, "core fucosylation" refers to addition of fucose ("fucosylation") to N-acetylglucosamine ("GlcNAc") at the reducing terminal of an N-linked glycan. Also provided are antibodies and antibody derivatives produced by such methods. In other aspects, fucose analogs and culture media comprising an effective amount of a fucose analog(s) are provided.

In some embodiments, fucosylation of complex N-glycoside-linked sugar chains bound to the Fc region (or domain) is reduced. As used herein, a "complex N-glycoside-linked sugar chain" is typically bound to asparagine 297 (according to the number of Kabat), although a complex N-glycoside linked sugar chain can also be linked to other asparagine residues. As used herein, the complex N-glycoside-linked sugar chain has a bianntennary composite sugar chain, mainly having the following structure:

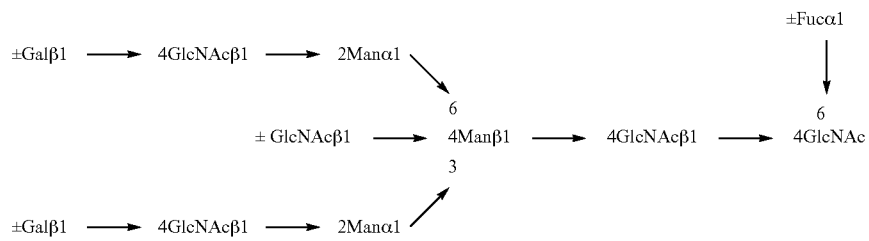

where ± indicates the sugar molecule can be present or absent, and the numbers indicate the position of linkages between the sugar molecules. In the above structure, the sugar chain terminal which binds to asparagine is called a reducing terminal (at right), and the opposite side is called a non-reducing terminal. Fucose is usually bound to N-acetylglucosamine ("GlcNAc") of the reducing terminal, typically by an α1,6 bond (the 6-position of GlcNAc is linked to the 1-position of fucose). "Gal" refers to galactose, and "Man" refers to mannose.

A "complex N-glycoside-linked sugar chain" excludes a high mannose type of sugar chain, in which only mannose is incorporated at the non-reducing terminal of the core structure, but includes 1) a complex type, in which the non-reducing terminal side of the core structure has one or more branches of galactose-N-acetylglucosamine (also referred to as "gal-GlcNAc") and the non-reducing terminal side of Gal-GlcNAc optionally has a sialic acid, bisecting N-acetylglucosamine or the like; or 2) a hybrid type, in which the non-reducing terminal side of the core structure has both branches of the high mannose N-glycoside-linked sugar chain and complex N-glycoside-linked sugar chain.

In some embodiments, the "complex N-glycoside-linked sugar chain" includes a complex type in which the non-reducing terminal side of the core structure has zero, one or more branches of galactose-N-acetylglucosamine (also referred to as "gal-GlcNAc") and the non-reducing terminal side of Gal-GlcNAc optionally further has a structure such as a sialic acid, bisecting N-acetylglucosamine or the like.

According to the present methods, typically only a minor amount of fucose is incorporated into the complex N-glycoside-linked sugar chain(s). For example, in various embodiments, less than about 60%, less than about 50%, less than about 40%, less than about 30%, less than about 20%, less than about 15%, less than about 10%, less than about 5%, or less than about 1% of the antibody or antibody derivative has core fucosylation by fucose. In some embodiments, substantially none (i.e., less than 0.5%) of the antibody or antibody derivative has core fucosylation by fucose.

In certain embodiments, only a minor amount of a fucose analog (or a metabolite or product of the fucose analog) is incorporated into the complex N-glycoside-linked sugar chain(s). For example, in various embodiments, less than about 40%, less than about 30%, less than about 20%, less than about 15%, less than about 10%, less than about 5%, or less than about 1% of the antibody or antibody derivative has core fucosylation by a fucose analog or a metabolite or product of the fucose analog. In some embodiments, substantially none (i.e., less than 0.5%) of the antibody or antibody derivative has core fucosylation by a fucose analog or a metabolite or product of the fucose analog.

Fucose Analogs

In one aspect, fucose analogs are described that reduce the incorporation of fucose into complex N-glycoside-linked sugar chains of antibodies or antibody derivatives produced by host cells. Suitable fucose analogs (identified below as Formula I, II, III, IV, V and VI) are those that can be added to the host cell culture media and that inhibit core fucosylation of complex N-glycoside-linked sugar chains of antibodies or antibody derivatives. The fucose analog is typically taken up by host cells (e.g., by active transport or passive diffusion).

In some embodiments, a fucose analog (or an intracellular metabolite or product of the fucose analog) inhibits an enzyme(s) in the fucose salvage pathway. (As used herein, an intracellular metabolite can be, for example, a GDP-modified analog or a fully or partially de-esterified analog. A product can be, for example, a fully or partially de-esterified analog.) For example, a fucose analog (or an intracellular metabolite or product of the fucose analog) can inhibit the activity of fucokinase, or GDP-fucose-pyrophosphorylase. In some embodiments, a fucose analog (or an intracellular metabolite or product of the fucose analog) inhibits fucosyltransferase (preferably a 1,6-fucosyltransferase, e.g., the FUT8 protein). In some embodiments, a fucose analog (or an intracellular metabolite or product of the fucose analog) can inhibit the activity of an enzyme in the de novo synthetic pathway for fucose. For example, a fucose analog (or an intracellular metabolite or product of the fucose analog) can inhibit the activity of GDP-mannose 4,6-dehydratase or/or GDP-fucose synthetase. In some embodiments, the fucose analog (or an intracellular metabolite or product of the fucose analog) can inhibit a fucose transporter (e.g., GDP-fucose transporter).

In some embodiments, the fucose analog has the following formula (I) or (II):

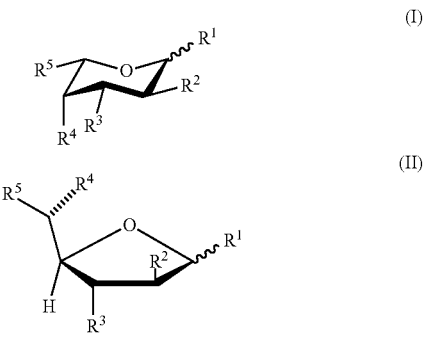

or a biologically acceptable salt or solvate of the analog, wherein each of formula (I) or (II) can be the alpha or beta anomer or the corresponding aldose form. In the above formulae, each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, —OC(O)$C_2$-$C_{10}$ alkynylene heterocycle, —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-$C_1$-$C_3$ alkyl silyl, —OC$_1$-$C_{10}$ alkyl, —OCH$_2$OC(O) alkyl, —OCH$_2$OC(O) alkenyl, —OCH$_2$OC(O) alkynyl, —OCH$_2$OC(O) aryl, —OCH$_2$OC(O) heterocycle, —OCH$_2$OC(O)O alkyl, —OCH$_2$OC(O)O alkenyl, —OCH$_2$OC(O)O alkynyl, —OCH$_2$OC(O)O aryl and —OCH$_2$OC(O)O heterocycle, wherein each n is an integer independently selected from 0-5; and $R^5$ is selected from the group consisting of —C≡CH, —C≡CCH$_3$, —CH$_2$C≡CH, —C(O)OCH$_3$, —CH(OAc)CH$_3$, —CN, —CH$_2$CN, —CH$_2$X (wherein X is Br, Cl or I), and methoxiran.

In some embodiments, the fucose analog has formula (I) or (II), wherein:
each of $R^1$-$R^4$ is independently selected from the group consisting of —OH, —OC(O)H, —OC(O)$C_1$-$C_{10}$ alkyl, —OC(O)aryl, —OC(O)heterocycle, —OC(O)$C_1$-$C_{10}$ alkylene aryl, —OC(O)$C_1$-$C_{10}$ alkylene heterocycle, —OC(O)CH$_2$O (CH$_2$CH$_2$O)$_n$CH$_3$, —OC(O)CH$_2$CH$_2$O(CH$_2$CH$_2$O)$_n$CH$_3$, —O-tri-$C_1$-$C_3$ silyl, —OC$_1$-$C_{10}$ alkyl, —OCH$_2$OC(O) alkyl, —OCH$_2$OC(O)O alkyl, —OCH$_2$OC(O) aryl, and —OCH$_2$OC(O)O aryl, wherein each n is an integer independently selected from 0-5; and $R^5$ is selected from the group consisting of —C≡CH, —C≡CCH$_3$, —CH$_2$C≡CH, —C(O)OCH$_3$, —CH(OAc)CH$_3$, —CN, —CH$_2$CN, —CH$_2$X (wherein X is Br, Cl or I), and methoxiran.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡CCH$_3$, —CH$_2$C≡CH, —C(O)OCH$_3$, —CH(OAc)CH$_3$, —CN, —CH$_2$CN, —CH$_2$X (wherein X is Br, Cl or I), and methoxiran.

In some embodiments, the fucose analog has formula (I) or (II), wherein each of $R^1$-$R^4$ is independently selected from the group consisting of —O-tri-$C_1$-$C_3$ silyl and —O$C_1$-$C_{10}$ alkyl; and $R^5$ is selected from the group consisting of —C≡CH, —C≡CCH$_3$, —CH$_2$C≡CH, —C(O)OCH$_3$, —CH(OAc)CH$_3$, —CN, —CH$_2$CN, —CH$_2$X (wherein X is Br, Cl or I), and methoxiran.

In some embodiments, the fucose analog has formula (I) or (II), wherein each of $R^1$-$R^4$ is independently selected from the group consisting of —OCH$_2$OC(O) alkyl, —OCH$_2$OC(O) alkenyl, —OCH$_2$OC(O) alkynyl, —OCH$_2$OC(O) aryl, —OCH$_2$OC(O) heterocycle, —OCH$_2$OC(O)O alkyl, —OCH$_2$OC(O)O alkenyl, —OCH$_2$OC(O)O alkynyl, —OCH$_2$OC(O)O aryl, and —OCH$_2$OC(O)O heterocycle; and $R^5$ is selected from the group consisting of —C≡CH, —C≡CCH$_3$, —CH$_2$C≡CH, —C(O)OCH$_3$, —CH(OAc)CH$_3$, —CN, —CH$_2$CN, —CH$_2$X (wherein X is Br, Cl or I), and methoxiran.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡CCH$_3$, —CH$_2$C≡CH, —C(O)OCH$_3$, —CH(OAc)CH$_3$, —CN, —CH$_2$CN, and methoxiran.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —CH$_2$I, —CH$_2$Br, and —CH$_2$Cl.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡CCH$_3$ and —CH$_2$C≡CH.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡CCH$_3$, —(CH$_2$)$_n$(CN) (where n=0 or 1) and —CO(O)CH$_3$.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡CCH$_3$, —CH$_2$CN and —CO(O)CH$_3$.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡CCH$_3$, —CH(OAc)CH$_3$, —CH$_2$CN, and —CO(O)CH$_3$.

In some embodiments, the fucose analog has formula (I) or (II), wherein $R^5$ is as defined herein, and each of $R^1$-$R^4$ is other than hydroxyl.

In some embodiments, the fucose analog has formula (I) or (II), wherein each of $R^1$-$R^4$ is independently selected from the group consisting of —OH, and —OAc; and $R^5$ is selected from the group consisting of —C≡CH, —C≡CCH$_3$, —CH(OAc)CH$_3$, —CH$_2$CN, and —CO(O)CH$_3$.

In some embodiments, the fucose analog has formula (I) or (II), wherein each of $R^1$-$R^4$ is —OH or an ester selected from the group consisting of —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_1$-$C_{10}$ alkylene heterocycle, —OC(O)$C_2$-$C_{10}$ alkenylene heterocycle, —OC(O)$C_2$-$C_{10}$ alkynylene heterocycle, —OC(O)CH$_2$O(CH$_2$CH$_2$O)$_n$CH$_3$ (where n is 0-5), and —OC(O)CH$_2$CH$_2$O(CH$_2$CH$_2$O)$_n$CH$_3$ (where n is 0-5); and $R^5$ is selected from the group consisting of —C≡CH, —C≡CCH$_3$, —CH$_2$C≡CH, —C(O)OCH$_3$, —CH(OAc)CH$_3$, —CN, —CH$_2$CN, —CH$_2$X (wherein X is Br, Cl or I), and methoxiran.

In some embodiments, the fucose analog has a molecular weight of less than 2000 daltons. In some embodiments, the fucose analog has a molecular weight of less than 1000 daltons.

In some embodiments, $R^5$ is not substituted.

In some embodiments, each of $R^1$-$R^4$ is not substituted.

In some embodiments, $R^5$ is not a ketone (—C(O)alkyl).

In some embodiments, $R^5$ is not —CHCH$_3$OAc.

In some embodiments, $R^5$ is not —CHCH$_3$OAc, when each of $R^1$-$R^4$ is —OAc.

In some embodiments, $R^5$ is not —C≡CH$_3$.

In some embodiments, $R^5$ is not —C≡CH$_3$, when any of $R^1$-$R^4$ is —OAc.

In some embodiments, $R^5$ is not —C≡CH$_3$, when any of $R^1$-$R^4$ is —OC(O)alkyl.

In some embodiments, $R^5$ is not —C≡CH$_3$, when each of $R^1$-$R^4$ is —OC(O)alkyl.

In some embodiments, $R^5$ is not —C≡CH$_3$, when each of $R^1$-$R^4$ is OH.

In some embodiments, the fucose analog is alkynyl fucose peracetate. In some embodiments, the fucose analog is alkynyl fucose triacetate. In some embodiments, the fucose analog is alkynyl fucose diacetate. In some embodiments, the fucose analog is mixture of alkynyl fucose peracetate, alkynyl fucose triacetate and alkynyl fucose diacetate.

In some embodiments, the fucose analog is mixture of alkynyl fucose peracetate, alkynyl fucose triacetate, alkynyl fucose diacetate and alkynyl fucose monoacetate.

In any of the various embodiments, the fucose analog is not fucose. In some embodiments, the fucose analog is not alkynyl fucose peracetate. In some embodiments, the fucose analog is not galactose or L-galactose.

In another group of embodiments, the fucose analog has the following formula (III) or (IV):

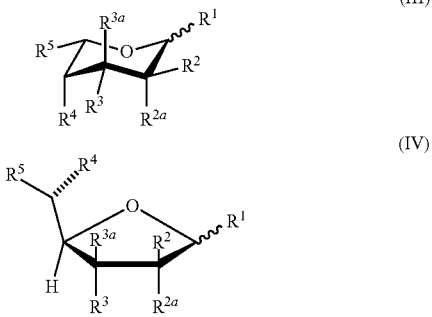

or a biologically acceptable salt or solvate thereof, wherein each of formula (III) or (IV) can be the alpha or beta anomer or the corresponding aldose form; and wherein, each of $R^1$-$R^4$ is independently selected from the group consisting of fluoro, chloro, —OH, —OC(O)H, —OC(O)C$_1$-C$_{10}$ alkyl, —OC(O)C$_2$-C$_{10}$ alkenyl, —OC(O)C$_2$-C$_{10}$ alkynyl, —OC(O)aryl, —OC(O)heterocycle, —OC(O)C$_1$-C$_{10}$ alkylene(aryl), —OC(O)C$_2$-C$_{10}$ alkylene(aryl), —OC(O)C$_2$-C$_{10}$ alkynyl(aryl), —OC(O)C$_1$-C$_{10}$ alkylene heterocycle, —OC(O)C$_2$-C$_{10}$ alkenylene(heterocycle), —OC(O)C$_2$-C$_{10}$ alkynyl heterocycle, —OCH$_2$OC(O) alkyl, —OCH$_2$OC(O)O alkyl; —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-C$_1$-C$_3$ alkylsilyl and —OC$_1$-C$_{10}$ alkyl, wherein each n is an integer independently selected from 0-5; and each of $R^{2a}$ and $R^{3a}$ is independently selected from the group consisting of H, F and Cl;

$R^5$ is selected from the group consisting of —CH$_3$, —CHF$_2$, —CH=C=CH$_2$, —C≡CH, —C≡CCH$_3$, —CH$_2$C≡CH, —C(O)OCH$_3$, —CH(OAc)CH$_3$, —CN, —CH$_2$CN, —CH$_2$X (wherein X is Br, Cl or I), and methoxiran;

wherein when $R^5$ is other than —CH=C=CH$_2$ or —CHF$_2$, at least one of $R^1$, $R^2$, $R^3$, $R^{2a}$ and $R^{3a}$ is fluoro or chloro.

In some embodiments of formulae (III) or (IV), $R^1$ is F.
In some embodiments of formulae (III) or (IV), $R^2$ is F.
In some embodiments of formulae (III) or (IV), $R^3$ is F.
In some embodiments of formulae (III) or (IV), $R^1$ and $R^2$ are each F.
In some embodiments of formulae (III) or (IV), $R^2$ and $R^{2a}$ are each F.

In some embodiments of formulae (III) or (IV), $R^1$, $R^3$ and $R^4$ are each independently selected from —OH and —OAc; $R^2$ is F; and $R^5$ is —CH$_3$.

In some embodiments of formulae (III) or (IV), $R^1$, $R^3$ and $R^4$ are each independently selected from —OH and —OAc; $R^2$ is F; $R^{2a}$ and $R^{3a}$ are each H; and $R^5$ is —CH$_3$.

In another group of embodiments, the fucose analog has the following formula (V) or (VI):

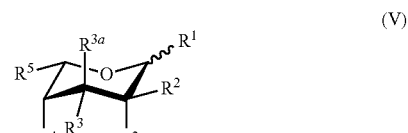

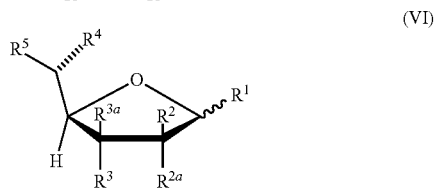

or a biologically acceptable salt or solvate thereof, wherein each of formula (V) or (VI) can be the alpha or beta anomer or the corresponding aldose form; and wherein, each of $R^1$, $R^2$, $R^{2a}$, $R^3$, $R^{3a}$ and $R^4$ is independently selected from the group consisting of —OH, —OC(O)H, —OC(O)C$_1$-C$_{10}$ alkyl, —OC(O)C$_2$-C$_{10}$ alkenyl, —OC(O)C$_2$-C$_{10}$ alkynyl, —OC(O)aryl, —OC(O)heterocycle, —OC(O)C$_1$-C$_{10}$ alkylene(aryl), —OC(O)C$_2$-C$_{10}$ alkylene(aryl), —OC(O)C$_2$-C$_{10}$ alkynyl(aryl), —OC(O)C$_1$-C$_{10}$ alkylene heterocycle, —OC(O)C$_2$-C$_{10}$ alkenylene(heterocycle), —OC(O)C$_2$-C$_{10}$ alkynyl heterocycle, —OCH$_2$OC(O) alkyl, —OCH$_2$OC(O)O alkyl, —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-C$_1$-C$_3$ alkylsilyl, —OC$_1$-C$_{10}$ alkyl, and a small electron withdrawing group, wherein each n is an integer independently selected from 0-5;

$R^5$ is a member selected from the group consisting of —CH$_3$, —CH$_2$X, —CH(X')—C$_1$-C$_4$ alkyl unsubstituted or substituted with halogen, —CH(X')—C$_2$-C$_4$ alkene unsubstituted or substituted with halogen, —CH(X')—C$_2$-C$_4$ alkyne unsubstituted or substituted with halogen, —CH=C(R$^{10}$)(R$^{11}$), —C(CH$_3$)=C(R$^{12}$)(R$^{13}$), —C(R$^{14}$)=C=C(R$^{15}$)(R$^{16}$), —C$_3$ carbocycle unsubstituted or substituted with methyl or halogen, —CH(X')—C$_3$ carbocycle unsubstituted or substituted with methyl or halogen, C$_3$ heterocyle unsubstituted or substituted with methyl or halogen, —CH(X')—C$_3$ heterocycle unsubstituted or substituted with methyl or halogen, —CH$_2$N$_3$, —CH$_2$CH$_2$N$_3$, and benzyloxymethyl, or $R^5$ is a small electron withdrawing group;

wherein $R^{10}$ is hydrogen or C$_1$-C$_3$ alkyl unsubstituted or substituted with halogen; $R^{11}$ is C$_1$-C$_3$ alkyl unsubstituted or substituted with halogen; $R^{12}$ is hydrogen, halogen or C$_1$-C$_3$ alkyl unsubstituted or substituted with halogen; $R^{13}$ is hydrogen, or C$_1$-C$_3$ alkyl unsubstituted or substituted with halogen; $R^{14}$ is hydrogen or methyl; $R^{15}$ and $R^{16}$ are independently selected from hydrogen, methyl and halogen; X is halogen; X' is halogen or hydrogen; and additionally, each of $R^1$, $R^2$, $R^{2a}$, $R^3$ and $R^{3a}$ are optionally hydrogen; optionally two $R^1$, $R^2$, $R^{2a}$, $R^3$ and $R^{3a}$ on adjacent carbon atoms are combined to form a double bond between said adjacent carbon atoms; and provided that at least one of $R^1$, $R^2$, $R^{2a}$, $R^3$, $R^{3a}$, $R^4$ and $R^5$ is a small electron withdrawing group, or $R^5$ comprises a halogen, site of unsaturation, carbocycle, heterocycle or azide, except when (i) $R^2$ and $R^{2a}$ are both hydrogen, (ii) $R^3$ and $R^{3a}$ are both hydrogen, (iii) $R^1$ is hydrogen, (iv) a double bond is present between said adjacent carbon atoms, or (v) $R^5$ is benzyloxymethyl; and
wherein the antibody or antibody derivative has reduced core fucosylation compared to the antibody or antibody derivative from the host cell cultured in the absence of the fucose analog.

In some embodiments of formulae (V) and (VI), $R^{2a}$ and $R^{3a}$ are each hydrogen.

In some embodiments of formulae (V) and (VI), $R^5$ is selected from the group consisting of —$CH_3$, —$CH_2CH_3$, —$CH_2C\equiv CH$, —$CH=CHCH_3$, -cyclopropyl, -oxirane, -oxirane substituted with methyl, —$CH_2F$, —$CH_2Cl$, —$CH_2Br$, —$CH_2I$, —$CH=C=CH_2$, —$CH_2N_3$ and —$CH_2CH_2N_3$.

In some embodiments of formulae (V) and (VI), the small electron withdrawing group is selected from fluoro, chloro, bromo, —$CHF_2$, —$CH=C=CH_2$, —$C\equiv CH$, —$C\equiv CCH_3$, —$CH_2C\equiv CH$, —$CO_2H$, —$C(O)OC_1$-$C_4$ alkyl, —$CH(OAc)CH_3$, —$CN$, —$CH_2CN$, —$CH_2X$ (wherein X is Br, Cl or I), and methoxiran.

In some embodiments of formulae (V) and (VI), at least two of $R^1$, $R^2$, $R^{2a}$, $R^3$, $R^{3a}$ and $R^4$ are independently selected small electron withdrawing groups.

In some embodiments of formulae (V) and (VI), the fucose analog is selected from compounds of Tables 1, 2 or 3.

While the present inventive methods and cell cultures can include the fucose analogs provided in formulae I, II, III, IV, V and VI above, the present invention further provides compounds of each of the above formulae that can be prepared using methodology provided herein. In some embodiments, the compounds of the invention are other than compounds identified in the Examples as 6, 7, 9, 10, 22, 24, 26, 54, 56-58, 61-62, 65 and 66, as well as 2-fluoro-2-deoxyfucose.

Antibodies and Antibody Derivatives

Antibodies that can be produced by the instant methods can be monoclonal, chimeric, humanized (including veneered), or human antibodies. Suitable antibodies also include antibody fragments, such as single chain antibodies, or the like that have a Fc region or domain having a complex N-glycoside-linked sugar chain (e.g., a human IgG1 Fc region or domain). The Fc region or domain can include an Fcgamma receptor binding site. Typically, the antibodies are human or humanized. In some embodiments, the antibodies can be rodent (e.g., mouse and rat), donkey, sheep, rabbit, goat, guinea pig, camelid, horse, or chicken.

The antibodies can be mono-specific, bi-specific, tri-specific, or of greater multi-specificity. Multi-specific antibodies maybe specific for different epitopes of different target antigens or may be specific for different epitopes on the same target antigen. (See, e.g., WO 93/17715; WO 92/08802; WO 91/00360; WO 92/05793; Tutt et al., 1991, *J. Immunol.* 147: 60-69; U.S. Pat. Nos. 4,474,893; 4,714,681; 4,925,648; 5,573,920; and 5,601,819; Kostelny et al., 1992, *J. Immunol.* 148:1547-1553.)

The antibodies can also be described in terms of their binding affinity to a target antigen of $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In some embodiments, the antibody is a chimeric antibody. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. (See, e.g., Morrison, *Science,* 1985, 229:1202; Oi et al., 1986, *BioTechniques* 4:214; Gillies et al., 1989, *J. Immunol. Methods* 125:191-202; U.S. Pat. Nos. 5,807,715; 4,816,567; and 4,816,397.)

In some embodiments, the antibody can be a humanized antibody, including a veneered antibody. Humanized antibodies are antibody molecules that bind the desired antigen and have one or more complementarity determining regions (CDRs) from a non-human species, and framework and constant regions from a human immunoglobulin molecule. Often, framework residues in the human framework regions will be substituted with the corresponding residue from the CDR donor antibody to alter, or preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riecbmann et al., 1988, *Nature* 332:323.) Antibodies can be humanized using a variety of techniques known in the art such as CDR-grafting (EP 0 239 400; WO 91/09967; U.S. Pat. Nos. 5,225,539; 5,530,101; and 5,585,089), veneering or resurfacing (EP 0 592 106; EP 0 519 596; Padlan, 1991, *Molecular Immunology,* 28(4/5):489-498; Studnicka et al., 1994, *Protein Engineering* 7(6):805-814; Roguska et al., 1994, *Proc. Natl. Acad. Sci. USA* 91:969-973), and chain shuffling (U.S. Pat. No. 5,565,332) (all of these references are incorporated by reference herein).

The antibody can also be a human antibody. Human antibodies can be made by a variety of methods known in the art such as phage display methods using antibody libraries derived from human immunoglobulin sequences. See e.g., U.S. Pat. Nos. 4,444,887 and 4,716,111; WO 98/46645, WO 98/50433, WO 98/24893, WO 98/16654, WO 96/34096, WO 96/33735, and WO 91/10741. In addition, a human antibody recognizing a selected epitope can be generated using a technique referred to as "guided selection," in which a selected non-human monoclonal antibody, e.g., a mouse antibody, is used to guide the selection of a completely human antibody recognizing the same epitope (see, e.g., Jespers et al., 1994, *Biotechnology* 12:899-903). Human antibodies can also be produced using transgenic mice that express human immunoglobulin genes. Monoclonal antibodies directed against the antigen can be obtained from the immunized, transgenic mice using conventional hybridoma technology. For an overview of the technology for producing human antibodies, see Lonberg and Huszar, 1995, *Int. Rev. Immunol.* 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598,877; U.S. Pat. Nos. 5,413,923; 5,625,126; 5,633,425; 5,569,825; 5,661,016; 5,545,806; 5,814,318; 5,885,793; 5,916,771; and 5,939,598.

Examples of antibodies include HERCEPTIN® (trastuzumab; Genentech), RITUXAN® (rituximab; Genentech), lintuzumab (Seattle Genetics, Inc.), Palivizumab (Medimmune), Alemtuzumab (BTG) and Epratuzumab (Immunomedics).

In exemplary embodiments, an antibody or antibody derivative specifically binds to CD19, CD20, CD21, CD22, CD30, CD33, CD38, CD40, CD70, CD133, CD138, or CD276. In other embodiments, the antibody or antibody derivative specifically binds to BMPR1B, LAT1 (SLC7A5), STEAP1, MUC16, megakaryocyte potentiating factor (MPF), Napi3b, Sema 5b, PSCA hlg, ETBR (Endothelin type B receptor), STEAP2, TrpM4, CRIPTO, CD21, CD79a, CD79b, FcRH2, HER2, HER3, HER4, NCA, MDP, IL20Rα, Brevican, Ephb2R, ASLG659, PSCA, PSMA, GEDA, BAFF-R, CXCR5, HLA-DOB, P2X5, CD72, LY64, FCRH1, or IRTA2.

Antibodies can be assayed for specific binding to a target antigen by conventional methods, such as for example, competitive and non-competitive immunoassay systems using techniques such as Western blots, radioimmunoassays, ELISA (enzyme linked immunosorbent assay), "sandwich" immunoassays, immunoprecipitation assays, immunoradiometric assays, fluorescent immunoassays, and protein A immunoassays. (See, e.g., Ausubel et al., eds., *Short Protocols in Molecular Biology* (John Wiley & Sons, Inc., New York, 4th ed. 1999); Harlow & Lane, *Using Antibodies: A Laboratory Manual* (Cold Spring Harbor Laboratory Press, Cold Spring Harbor, N.Y., 1999.)

Further, the binding affinity of an antibody to a target antigen and the off-rate of an antibody-antigen interaction can be determined by surface plasmon resonance, competition FACS using labeled antibodies or other competitive binding assays. One example of a competitive binding assay is a radioimmunoassay comprising the incubation of labeled antigen (e.g., $^3$H or $^{125}$I) with the antibody of interest in the presence of increasing amounts of unlabeled antibody, and the detection of the antibody bound to the labeled antigen. The affinity of the antibody and the binding off-rates can then be determined from the data by Scatchard plot analysis. Competition with a second antibody can also be determined using radioimmunoassays. In this case, the antigen is incubated with the antibody of interest conjugated to a labeled compound (e.g., $^3$H or $^{125}$I) in the presence of increasing amounts of an unlabeled second antibody. Alternatively, the binding affinity of an antibody and the on- and off-rates of an antibody-antigen interaction can be determined by surface plasmon resonance.

Antibodies can be made from antigen-containing fragments of the target antigen by standard procedures according to the type of antibody (see, e.g., Kohler, et al., *Nature,* 256: 495, (1975); Harlow & Lane, *Antibodies, A Laboratory Manual* (C.S.H.P., NY, 1988); Queen et al., *Proc. Natl. Acad. Sci. USA* 86:10029-10033 (1989) and WO 90/07861; Dower et al., WO 91/17271 and McCafferty et al., WO 92/01047 (each of which is incorporated by reference for all purposes). As an example, monoclonal antibodies can be prepared using a wide variety of techniques including, e.g., the use of hybridoma, recombinant, and phage display technologies, or a combination thereof. Hybridoma techniques are generally discussed in, e.g., Harlow et al., supra, and Hammerling, et al., *In Monoclonal Antibodies and T-Cell Hybridomas*, pp. 563-681 (Elsevier, N.Y., 1981). Examples of phage display methods that can be used to make antibodies include, e.g., those disclosed in Briinnan et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187:9-18; Burton et al., 1994, *Advances in Immunology* 57:191-280; PCT Application No. PCT/GB91/01 134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

Examples of techniques that can be used to produce single-chain Fvs and antibodies include those described in U.S. Pat. Nos. 4,946,778 and 5,258,498; Huston et al., 1991, *Methods in Enzymology* 203:46-88; Shu et al., 1993, *Proc. Natl. Acad. Sci. USA* 90:7995-7999; and Skerra et al., 1988, *Science* 240:1038-1040.

Examples of antibody derivatives include binding domain-Ig fusions, wherein the binding domain may be, for example, a ligand, an extracellular domain of a receptor, a peptide, a non-naturally occurring peptide or the like. Exemplary fusions with immunoglobulin or Fc regions include: etanercept which is a fusion protein of sTNFRII with the Fc region (U.S. Pat. No. 5,605,690), alefacept which is a fusion protein of LFA-3 expressed on antigen presenting cells with the Fc region (U.S. Pat. No. 5,914,111), a fusion protein of Cytotoxic T Lymphocyte-associated antigen-4 (CTLA-4) with the Fc region (*J. Exp. Med.* 181:1869 (1995)), a fusion protein of interleukin 15 with the Fc region (*J. Immunol.* 160:5742 (1998)), a fusion protein of factor VII with the Fc region (*Proc. Natl. Acad. Sci. USA* 98:12180 (2001)), a fusion protein of interleukin 10 with the Fc region (*J. Immunol.* 154: 5590 (1995)), a fusion protein of interleukin 2 with the Fc region (*J. Immunol.* 146:915 (1991)), a fusion protein of CD40 with the Fc region (*Surgery* 132:149 (2002)), a fusion protein of Flt-3 (fms-like tyrosine kinase) with the antibody Fc region (*Acta. Haemato.* 95:218 (1996)), a fusion protein of OX40 with the antibody Fc region (*J. Leu. Biol.* 72:522 (2002)), and fusion proteins with other CD molecules (e.g., CD2, CD30 (TNFRSF8), CD95 (Fas), CD106 (VCAM-1), CD137), adhesion molecules (e.g., ALCAM (activated leukocyte cell adhesion molecule), cadherins, ICAM (intercellular adhesion molecule)-1, ICAM-2, ICAM-3) cytokine receptors (e.g., interleukin-4R, interleukin-5R, interleukin-6R, interleukin-9R, interleukin-10R, interleukin-12R, interleukin-13Ralpha1, interleukin-13Ralpha2, interleukin-15R, interleukin-21Ralpha), chemokines, cell death-inducing signal molecules (e.g., B7-H1, DR6 (Death receptor 6), PD-1 (Programmed death-1), TRAIL R1), costimulating molecules (e.g., B7-1, B7-2, B7-H2, ICOS (inducible co-stimulator)), growth factors (e.g., ErbB2, ErbB3, ErbB4, HGFR), differentiation-inducing factors (e.g., B7-H3), activating factors (e.g., NKG2D), signal transfer molecules (e.g., gp130), BCMA, and TACI.

Methods of Making Non-Core Fucosylated Antibodies and Antibody Derivatives

Antibodies and derivatives thereof that are useful in the present methods can be produced by recombinant expression techniques, from hybridomas, from myelomas or from other antibody expressing mammalian cells. Recombinant expression of an antibody or derivative thereof that binds to a target antigen typically involves construction of an expression vector containing a nucleic acid that encodes the antibody or derivative thereof. Once a nucleic acid encoding such a protein has been obtained, the vector for the production of the protein molecule may be produced by recombinant DNA technology using techniques well known in the art. Standard techniques such as those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); Ausubel et al., *Short Protocols in Molecular Biology* (John Wiley & Sons, New York, 4th ed., 1999); and Glick & Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of antibody, an expression vector may encode a heavy or light chain thereof, or a heavy or light chain variable domain, operably linked to a promoter. An expression vector may include, e.g., the nucleotide sequence encoding the constant region of the antibody molecule (see, e.g., WO 86/05807; WO 89/01036; and U.S. Pat. No. 5,122,464), and the variable domain of the antibody may be cloned into such a vector for expression of the entire heavy or light chain. The expression vector is transferred to a host cell by techniques known in the art, and the transfected cells are then cultured by techniques known in the art in the presence of a fucose analog to produce the antibody. Typically, for the expression of double-chained antibodies, vectors encoding both the heavy and light chains can be co-expressed in the host cell for expression of the entire immunoglobulin molecule.

A variety of mammalian cells and cell lines can be utilized to express an antibody or derivative thereof. For example, mammalian cells such as Chinese hamster ovary cells (CHO) (e.g., DG44, Dxb11, CHO-K, CHO-K1 and CHO-S) can be used. In some embodiments, human cell lines are used. Suitable myeloma cell lines include SP2/0 and IR983F and human myeloma cell lines such as Namalwa. Other suitable cells include human embryonic kidney cells (e.g., HEK293), monkey kidney cells (e.g., COS), human epithelial cells (e.g., HeLa), PERC6, Wil-2, Jurkat, Vero, Molt-4, BHK, and K6H6. Other suitable host cells include YB2/0 cells. In other embodiments, the host cells are not YB2/0 cells.

In some embodiments, the host cells are from a hybridoma. In some embodiments, the host cells are not a hybridoma produced by a fusion generated with NS0 myeloma cells. In other embodiments, the host cells are not from a hybridoma.

In some embodiments, the host cells do not contain a fucose transporter gene knockout. In some embodiments, the host cells do not contain a fucosyltransferase (e.g., FUT8) gene knockout. In some embodiments, the host cells do not contain a knock-in of a GnTIII encoding nucleic acid. In some embodiments, the host cells do not contain a knock-in of a golgi alpha mannosidase II encoding nucleic acid.

A variety of mammalian host-expression vector systems can be utilized to express an antibody or derivative thereof. For example, mammalian cells such as Chinese hamster ovary cells (CHO) (e.g., DG44, Dxb11, CHO-K1 and CHO-S) in conjunction with a vector such as the major intermediate early gene promoter element from human cytomegalovirus or the Chinese hamster ovary EF-1α promoter, is an effective expression system for the production of antibodies and derivatives thereof (see, e.g., Foecking et al., 1986, *Gene* 45:101; Cockett et al., 1990, *Bio/Technology* 8:2; Allison, U.S. Pat. No. 5,888,809).

The cell lines are cultured in the appropriate culture medium. Suitable culture media include those containing, for example, salts, carbon source (e.g., sugars), nitrogen source, amino acids, trace elements, antibiotics, selection agents, and the like, as required for growth. For example, commercially available media such as Ham's F10 (Sigma), Minimal Essential Medium (MEM, Sigma), RPMI-1640 (Sigma), Dulbecco's Modified Eagle's Medium ((DMEM, Sigma), Power-CHO™ cell culture media (Lonza Group Ltd.) Hybridoma Serum-Free Medium (HSFM) (GIBCO) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, can be those previously used with the host cell selected for expression, and will be apparent to the ordinarily skilled artisan.

The culture media preferably is not supplemented with fucose. In some embodiments, the culture media is a serum-free media. In some embodiments, the culture media is an animal-derived protein free (i.e., animal protein free) media.

An effective amount of a fucose analog is added to the culture media. In this context, an "effective amount" refers to an amount of the analog that is sufficient to decrease fucose incorporation into a complex N-glycoside-linked sugar chain of an antibody or antibody derivative by at least 10%, at least 20%, at least 30%, at least 40% or at least 50%. In some embodiments, the effective amount of the fucose analog is sufficient to reduce fucose incorporation into a complex N-glycoside-linked sugar chain of an antibody or antibody derivative by at least 60%, at least 70%, at least 80% or at least 90%.

The cells expressing the antibody or antibody derivative can be cultured by growing the host cell in any suitable volume of culture media supplemented with the fucose analog. The cells may be cultured in any suitable culture system and according to any method known in the art, including T-flasks, spinner and shaker flasks, WaveBag® bags, roller bottles, bioreactors and stirred-tank bioreactors. Anchorage-dependent cells can also be cultivated on microcarrier, e.g., polymeric spheres, that are maintained in suspension in stirred-tank bioreactors. Alternatively, cells can be grown in single-cell suspension. Culture medium may be added in a batch process, e.g., where culture medium is added once to the cells in a single batch, or in a fed batch process in which small batches of culture medium are periodically added. Medium can be harvested at the end of culture or several times during culture. Continuously perfused production processes are also known in the art, and involve continuous feeding of fresh medium into the culture, while the same volume is continuously withdrawn from the reactor. Perfused cultures generally achieve higher cell densities than batch cultures and can be maintained for weeks or months with repeated harvests.

For cells grown in batch culture, the volume of culture medium is typically at least 750 mL, 1 liter, 2 liters, 3 liters, 4 liters, 5 liters, 10 liters, 15 liters, 20 liters or more. For industrial applications, the volume of the culture medium can be at least 100 liters, at least 200 liters, at least 250 liters, at least 500 liters, at least 750 liters, at least 1000 liters, at least 2000 liters, at least 5000 liters or at least 10,000 liters. The fucose analog may be added to the seed train, to the initial batch culture medium, after a rapid growth phase, or continuously with culture medium (e.g., during continuous feeding). For example, the fucose analog may be added to an early seed train or feedstock at a 10× or 100× concentration, such that subsequent additions of culture media change the concentration of fucose analog to a level that is still effective in achieving non-core fucosylation of the antibody or antibody derivative. Alternatively, the fucose analog is added directly to the culture media, obviating the need for dilution. In any case, the fucose analog is typically added relatively early in the cell culturing process and an effective concentration is maintained throughout the culturing process in order to optimize production of the desired antibody or antibody derivative.

In some embodiments, antibodies or antibody derivatives produced by the instant methods comprise at least 10%, at least 20%, at least 30%, at least 40% or at least 50% non-core fucosylated protein (e.g., lacking core fucosylation), as compared with antibodies or antibody derivatives produced from the host cells cultured in the absence of a fucose analog. In some embodiments, antibodies or antibody derivatives produced by the instant methods comprise at least 60%, at least 70%, at least 75%, at least 80%, at least 85%, at least 90% or at least 95% non-core fucosylated antibody or antibody derivative, as compared with antibody or derivative produced from the host cells cultured in the absence of a fucose analog. In some embodiments, a composition of antibodies or antibody derivatives produced by the instant methods comprises less than 100% non-core fucosylated antibodies and/or antibody derivatives.

The amount of the fucose analog (of any of Formulae I, II, III, IV, V and VI) that is effective can be determined by standard cell culture methodologies. For example, cell culture assays may be employed to help identify optimal dosing ranges. The precise amount to be employed also depends on the time of administration, the host cell line, the cell density and the like. Effective doses may be extrapolated from dose-response curves derived from in vitro model test systems.

In some embodiments, the fucose analog is present in the culture medium at a concentration of 10 nM to 50 mM. In some embodiments, the fucose analog is present in the culture medium at a concentration of 10 nM to 10 mM. In some embodiments, the fucose analog is present in the culture medium at a concentration of 100 nM to 5 mM. In some embodiments, the fucose analog is present in the culture medium at a concentration of 100 nM to 3 mM. In some embodiments, the fucose analog is present in the culture medium at a concentration of 100 nM to 2 mM. In some embodiments, the fucose analog is present in the culture medium at a concentration of 100 nM to 1 mM. In some embodiments, the fucose analog is present in the culture medium at a concentration of 1 µM to 1 mM. In some embodiments, the fucose analog is present in the culture medium at a concentration of 10 nM to 1 mM. In some embodiments, the fucose analog is present in the culture medium at a concentration of 10 nM to 500 µM. In some embodiments, the fucose analog is present in the culture medium at a concentration of 1 µM to 500 µM. In some embodiments, the fucose analog is present in the culture medium at a concentration of 1 µM to 250 µM. In some embodiments, the fucose analog is present in the culture medium at a concentration of 10 µM to 100 µM. In some embodiments, the fucose analog is soluble in the culture medium (at the appropriate temperature for host cell maintenance/growth) at a concentration of at least 10 nM. In some embodiments, the fucose analog is soluble in the culture medium (at the appropriate temperature for host cell maintenance/growth) at a concentration of at least 100 nM.

The content (e.g., the ratio) of sugar chains in which fucose is not bound to N-acetylglucosamine in the reducing end of the sugar chain versus sugar chains in which fucose is bound to N-acetylglucosamine in the reducing end of the sugar chain can be determined, for example, as described in the Examples. Other methods include hydrazinolysis or enzyme digestion (see, e.g., *Biochemical Experimentation Methods 23: Method for Studying Glycoprotein Sugar Chain* (Japan Scientific Societies Press), edited by Reiko Takahashi (1989)), fluorescence labeling or radioisotope labeling of the released sugar chain and then separating the labeled sugar chain by chromatography. Also, the compositions of the released sugar chains can be determined by analyzing the chains by the HPAEC-PAD method (see, e.g., *J. Liq Chromatogr.* 6:1557 (1983)). (See generally U.S. Patent Application Publication No. 2004-0110282.)

In some embodiments, the antibodies or antibody derivatives produce by the instant methods have higher effector function (e.g., ADCC activity) than the antibodies or antibody derivatives produced in the absence of a fucose analog. The effector function activity may be modulated by altering the concentration of the fucose analog in the culture medium and/or the duration of exposure to the fucose analog. ADCC activity may be measured using assays known in the art and in exemplary embodiments increases by at least 10%, 20%, 30%, 40%, 50%, 60%, 70%, 80%, 90%, 2-fold, 3-fold, 4-fold, 5-fold, 6-fold, 7-fold, 8-fold, 9-fold, 10-fold, 15-fold or 20-fold, as compared to the core fucosylated parent antibody. The cytotoxic activity against an antigen-positive cultured cell line can be evaluated by measuring effector function (e.g., as described in *Cancer Immunol. Immunother.* 36:373 (1993)).

Antibodies and antibody derivative can be purified using, for example, hydroxylapatite chromatography, gel electrophoresis, dialysis, and affinity chromatography, with affinity chromatography being a preferred purification technique. The suitability of protein A as an affinity ligand depends on the species and isotype of any immunoglobulin Fc domain that is present in the antibody or antibody derivative. Protein A can be used to purify antibodies or antibody derivatives that are based on human IgG1, 2, or 4 heavy chains.

Protein G can be used for mouse isotypes and for some human antibodies and antibody derivatives. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody or antibody derivative comprises a $C_H3$ domain, the Bakerbond ABX™ resin (J. T. Baker, Phillipsburg, N.J.) is useful for purification. Other techniques for protein purification such as fractionation on an ion-exchange column (cationic or anionic exchange), ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody or antibody derivative to be recovered.

Following any purification step(s), the mixture comprising the antibody or antibody derivative of interest and contaminants may be subjected to low pH hydrophobic interaction chromatography (e.g., using an elution buffer at a pH between about 2.5-4.5, preferably performed at low salt concentrations (e.g., from about 0-0.25M salt)).

Uses of the Antibodies and Antibody Derivatives

Antibodies and antibody derivatives prepared according to the present methods can be used for a variety of therapeutic and non-therapeutic applications. For example, the antibodies can be used as therapeutic antibodies. Antibody derivatives (e.g., a receptor-Fc fusion) can be used as a therapeutic molecule. In some embodiments, the antibody or antibody derivative is not conjugated to another molecule. In some embodiments, the antibody is conjugated to a suitable drug (e.g., an antibody drug conjugate) or other active agent. The antibodies and antibody derivatives can also be used for non-therapeutic purposes, such as diagnostic assays, prognostic assays, release assays and the like.

Pharmaceutical Compositions.

Antibodies and antibody derivatives prepared according to the present methods can be formulated for therapeutic and non-therapeutic applications. The antibodies and derivatives can be formulated as pharmaceutical compositions comprising a therapeutically or prophylactically effective amount of the antibody or derivative and one or more pharmaceutically compatible (acceptable) ingredients. For example, a pharmaceutical or non-pharmaceutical composition typically includes one or more carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable excipients include, for example, amino acids, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin. Such compositions will typically contain a therapeutically effective amount of the protein, typically in purified form, together with a suitable amount of carrier so as to provide the faun for proper administration to the patient. The formulations correspond to the mode of administration.

Typically, compositions for intravenous administration are solutions in sterile isotonic aqueous buffer. When necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. When the pharmaceutical is to be administered by infusion, it can be dispensed with an infusion bottle containing sterile pharmaceutical grade water or saline. When the pharmaceutical is administered by injection, an ampoule of sterile water for injection or saline can be provided so that the ingredients can be mixed prior to administration.

The invention is further described in the following examples, which are not intended to limit the scope of the invention.

EXAMPLES

Example 1

Synthesis of Alkynyl Fucose Peracetate and General Procedure for Synthesis of Fucose Analogs The preparation of alkynyl fucose peracetate (also referred to as peracetyl alkynyl fucose and alkynyl peracetyl fucose) (Compound 7) was described by Sawa et al., 2006, *Proc. Natl. Acad. Sci. USA* 103:12371-12376 and Hsu et al., 2007, *Proc. Natl. Acad. Sci. USA* 104:2614-2619, with the following modification. A Corey-Fuchs homologation sequence was employed to install the alkynyl group, as described by Pelphrey et al., 2007, *J. Med. Chem.* 50:940-950.

General methods for other fucose analogs: Common reagents and solvents were purchased from either Fisher or Sigma-Aldrich except as follows: L-galactono-1,4-lactone was purchased from Carbosynth Limited. $^1$H-NMR spectra were recorded on a Varian Mercury spectrometer at 400 MHz. LC/MS data were obtained on a Waters Micromass instrument using an HP 1100 HPLC with a PDA detector. The column used was a Phenomenex SynergiMax RP-C12 column (2 mm×150 mm) eluting with a MeCN-water gradient containing 0.05% formic acid. Flash column chromatography (FCC) was performed using 230-400 mesh ASTM silica gel from EM Science or using a Chromatotron. Analtech silica gel GHLF plates were used for thinlayer chromatography and TLC plates were stained with vanillin or iodine. HPLC was performed using a Waters Alliance system with a PDA detector.

Example 2

Antibody Expression in the Presence of Alkynyl Fucose Peracetate

To determine the effect of alkynyl fucose peracetate on glycosylation of antibodies, a CHO DG44 cell line expressing a humanized IgG1 anti-CD70 monoclonal antibody, h1F6 (see International Patent Publication WO 06/113909) was cultured at $3.0 \times 10^5$ cells per mL in 30 mLs of CHO culture media at 37°, 5% $CO_2$, by shaking at 100 RPM in 125 mL shake flasks. The CHO culture media was supplemented with insulin like growth factor (IGF), penicillin, streptomycin and either 50 or 100 µM alkynyl fucose peracetate (prepared as described in Example 1). Cultures were fed on day 3 with 2% volume of feed media containing 2.5 or 5 mM alkynyl fucose peracetate for the 50 and 100 µM alkynyl fucose peracetate cultures, respectively. On day four, each culture was split 1:4 into fresh culture media. Cultures were fed with a 6% volume of feed media containing 833 µM or 1.66 mM alkynyl fucose peracetate on days 5, 7, 9 and 10. Conditioned media was collected on day 13 by passing the media through a 0.2 µm filter.

Antibody purification was performed by applying the conditioned media to a protein A column pre-equilibrated with 1× phosphate buffered saline (PBS), pH 7.4. After washing the column with 20 column volumes of 1×PBS, antibodies were eluted with 5 column volumes of Immunopure IgG elution buffer (Pierce Biotechnology, Rockford, Ill.). A 10% volume of 1M tris pH 8.0 was added to eluted fraction. The sample was dialyzed overnight into 1×PBS.

Example 3

LC-MS (Q-Tof) Analysis of Antibodies Produced by Expression in the Presence of Alkynyl Fucose Peracetate To identify the glycosylation pattern present on purified h1F6 antibodies from Example 2, antibody interchain disulfide bonds were reduced by adding 10 µL of 100 mM DTT to 90 µL of 1 mg/mL antibody in PBS and incubation at 37° C. for 15 min. This solution (20 µL) was injected onto a PLRP-S HPLC column (Polymer Laboratories; Amherst, Mass.) running the following gradient: solvent A, 0.05% TFA in water; solvent B, 0.035% TFA in acetonitrile; a linear gradient of 70 to 50% A from 0 to 12.5 min. The HPLC effluent was analyzed with an electrospray ionization Q-T of mass spectrometer (Waters, Milford, Mass.) with a cone voltage of 35 V collecting from m/z 500 to 4000. Data for the heavy chain were deconvoluted using the MaxEnt1 function in MassLynx 4.0.

Surprisingly, the heavy chains of antibodies from cells grown in the presence of alkynyl fucose peracetate showed a decrease by about 146 Da, as compared to control antibodies (i.e., heavy chains of antibodies from cells grown in the absence of alkynyl fucose peracetate). This observation suggested that addition of alkynyl fucose peracetate to the culture did not grossly alter the glycosylation pattern of the antibodies. Instead, addition of alkynyl fucose peracetate caused a minor but detectable change in glycosylation. The change in mass is consistent with the absence of fucose in the antibodies.

Example 4

Capillary Electrophoresis of Oligosaccharides

To further characterize the glycans on the h1F6 antibodies from Example 3, capillary electrophoresis was performed. Samples of the antibodies were buffer-exchanged into water. 300 μg of each sample was treated with PNGaseF overnight at 37° C. to release oligosaccharides. The protein component of the sample was removed by addition of cold methanol (−20° C.) and centrifuged for 10 minutes at 14,000 rpm. The supernatant was dried and oligosaccharides were labeled using APTS (8-aminopyrene-1,3,6-trisulfonic acid, trisodium salt) in 1M sodium cyanoborohydride/THF at 22° C. overnight. Labeled oligosaccharides were diluted with water and analyzed by capillary electrophoresis using a Beckman Coulter PA-800 in a N—CHO coated capillary (Beckman Coulter). For FIG. 1A, the samples were run in N-linked gel buffer (Beckman Coulter, Fullerton, Calif., USA). For FIGS. 1B and 1C, the samples were run in 40 mM EACA, 0.2% HPMC at pH 4.5. Samples were injected for 8 seconds at 0.5 psi and separated at 30 kV for 15 minutes. Labeled oligosaccharides were detected using laser induced fluorescence (LFI) with an excitation wavelength of 488λ. Emission fluorescence was detected at 520λ.

Samples of the antibodies were also treated with β-galactosidase to remove galactose. The antibody samples were buffer exchanged into water. 300 μg of each sample was treated with PNGaseF overnight at 37° C. to release oligosaccharides. The protein component of the sample was removed by addition of cold methanol (−20° C.) and centrifugation for 10 minutes at 14,000 rpm. The supernatants were dried, resuspended in water and treated with β-galactosidase. Oligosaccharides were dried and then labeled using APTS in 1M sodium cyanoborohydride/THF at 22° C. overnight. Labeled oligosaccharides were diluted with water and analyzed by capillary electrophoresis using a Beckman Coulter PA-800, in a N—CHO coated capillary (Beckman Coulter) running in 40 mM EACA, 0.2% HPMC at pH 4.5. Samples were injected for 8 seconds at 0.5 psi and separated at 30 kV for 15 minutes. Labeled oligosaccharides were detected using laser induced fluorescence (LFI) with an excitation wavelength of 488λ. Emission fluorescence was detected at 520λ.

An analysis of the data from the capillary electrophoresis is shown in FIG. 1. Referring to FIG. 1A, the electropherogram of glycans from the control h1F6 antibody are shown. FIG. 1B shows an electropherogram of glycans from the h1F6 antibody produced from a host cell grown in the presence of alkynyl fucose peracetate. A comparison of FIGS. 1A and 1B reveals increased amounts of non-core fucosylated G0-F (and a corresponding decrease in core fucosylated G0 and G1 levels). Because the non-core fucosylated G1 peak co-migrated with the core fucosylated G0, it was difficult to determine the relative distribution of the different glycans. To de-convolute the data, separate antibody samples were treated with β-galactosidase. Referring to FIG. 1C, removing the galactose effectively collapsed the electropherogram to two peaks, G0 and G0-F (lacking fucose). In this β-galactosidase treated sample, approximately 85% of the oligosaccharide is non-core fucosylated and 6% is core fucosylated. The remainder consists of minor species.

Example 5

Antibody Dependent Cellular Cytotoxicity (ADCC) Assay

To confirm that some of the h1F6 antibody produced in Example 2 was not core fucosylated (as compared to the parent antibody), the activity of the antibody was determined by an ADCC assay. The ADCC activity assay was a standard $^{51}$Cr release assay, as described previously (see McEarchern et al., *Blood* 109:1185 (2007)). Briefly, 786-O cell line target tumor cells were labeled with 100 μCi Na[$^{51}$Cr]O$_4$ and then washed. Effector (NK) cells were prepared from non-adherent peripheral blood mononuclear cells (PBMCs) obtained from normal FcγRIIIA 158V donors (Lifeblood, Memphis, Tenn.). The cell fraction was enriched for CD16$^+$ NK cells following centrifugation over a Ficoll-Paque density gradient by removal of T, B, and monocyte subsets and negative depletion of CD4, CD8, CD20, and CD14+ cells using immunomagnetic beads (EasySep, StemCell Technologies, Vancouver, BC, Canada). Na$_2$[$^{51}$Cr]O$_4$-labeled 786-O target tumor cells were mixed with mAb and the CD16+ effector cells at an effector:target cell ratio of 10:1.

After a 4 h incubation at 37° C., the radioactivity ($^{51}$Cr) released into the culture supernatant was measured and the percent specific cell lysis calculated as (test sample cpm−spontaneous cpm)/(total cpm−spontaneous cpm)×100. Spontaneous and total cpm were determined from the supernatants of target cells incubated in medium alone and from target cells lysed with 1% triton-X100, respectively.

Figure 2:
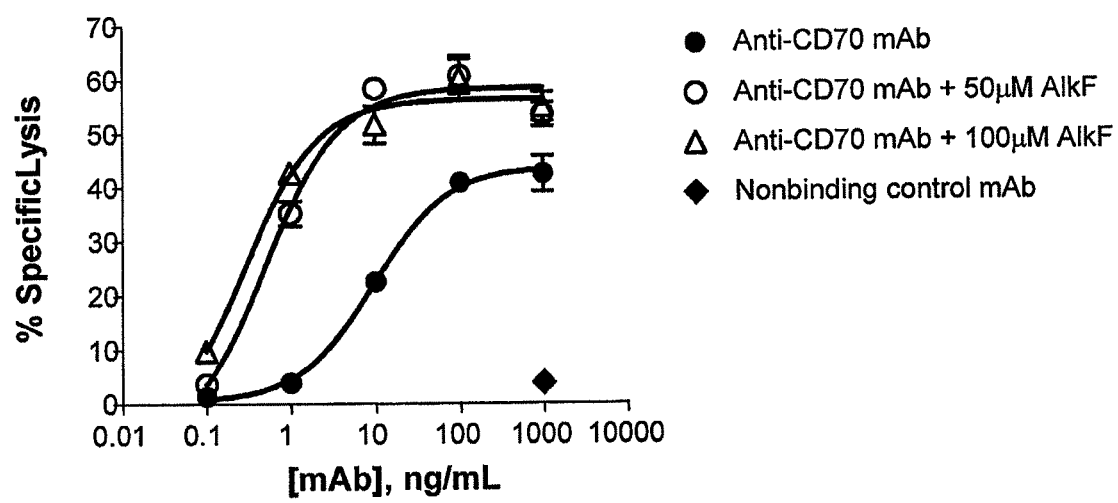
FIG. 2 shows the results of effector function assays (ADCC) with antibodies produced from host cells cultured in the presence of alkynyl fucose peracetate (AlkF). Specific lysis of control anti-CD70 antibody (shaded circles), anti-CD70 antibody from host cells cultured in the presence of 50 μM and 100 μM AlkF (open circles and triangles, respectively) and nonbinding control IgG (shaded diamonds) was determined by $^{51}$Cr release assay. CD70+ 786-O target cells were mixed with NK-enriched PBMCs at an effector to target ratio of 10:1.

Referring to FIG. 2, in the ADCC assay using PBMC as a source of natural killer (NK) cells (having the 158V phenotype), control anti-CD70 mAb (shaded circles) lysed CD70+ target cells in a dose dependent fashion, while no lysis was observed with nonbinding control human IgG (shaded diamonds). In contrast, anti-CD70 antibody isolated from host cells grown in the presence of alkynyl fucose peracetate ("AlkF") has enhanced ADCC activity (open circles and triangles). The half maximal lysis (EC$_{50}$) of control anti-CD70 antibody was about 9 ng/mL while the EC$_{50}$ concentrations of mAb produced in the presence of 50 μM and 100 μM AlkF were 0.5 and 0.3 ng/mL, respectively. The latter antibodies also gave rise to higher maximal specific lysis (53.3±3.8 and 54.8±4.7 percent) compared to that achieved with control anti-CD70 mAb (42.5±5.8 percent).

Example 6

FcγR Binding Assays

Fcγ receptor binding assays were performed to compare the binding of control CD70 antibody with the non-core fucosylated antibodies of Example 2. Briefly, stable CHO DG-44 cell lines expressing human FcγRIIIA V158 or murine FcγRIV were combined with 50 nmol/L or 200 nmol/L Alexa Fluor 488 labeled anti-CD70 IgG1, respectively, in the presence of serial dilutions of each of the following anti-CD70 antibodies in PBS, 0.1% BSA (w/v) buffer: control h1F6 antibody, and h1F6 antibody from host cells cultured with alkynyl fucose peracetate. The mixtures were incubated for 60 minutes on ice in the dark. Labeled cells were detected using an LSRII FACS analyzer and data were analyzed by a nonlinear least squares fit to a 4-parameter logistic equation using Prism v5.01 to estimate $EC_{50}$ values.

Figure 3:
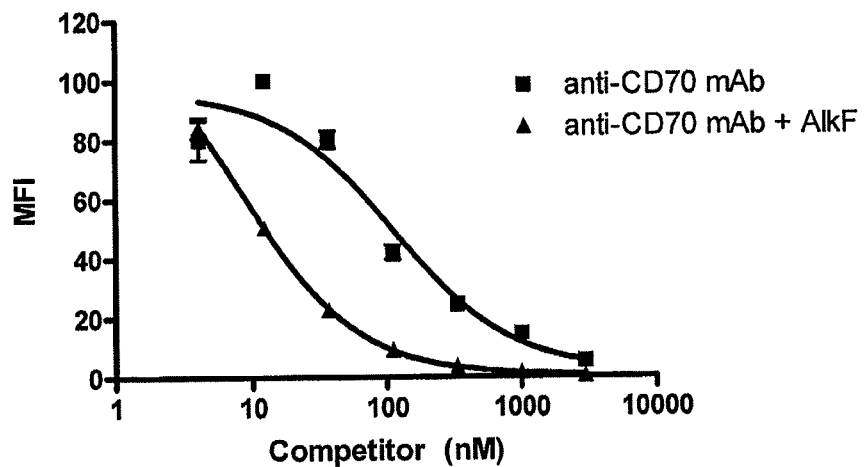
FIG. 3 shows the results of Fcγ receptor binding assays with control anti-CD70 antibody and antibody from host cells cultured in the presence of 50 μM alkynyl fucose peracetate (AlkF). The relative affinity for each receptor was determined by a competition binding assay between labeled parent antibody and increasing concentrations of unlabeled parent (shaded squares) or non-core fucosylated (shaded triangles) anti-CD70 mAb.
Figure 3:
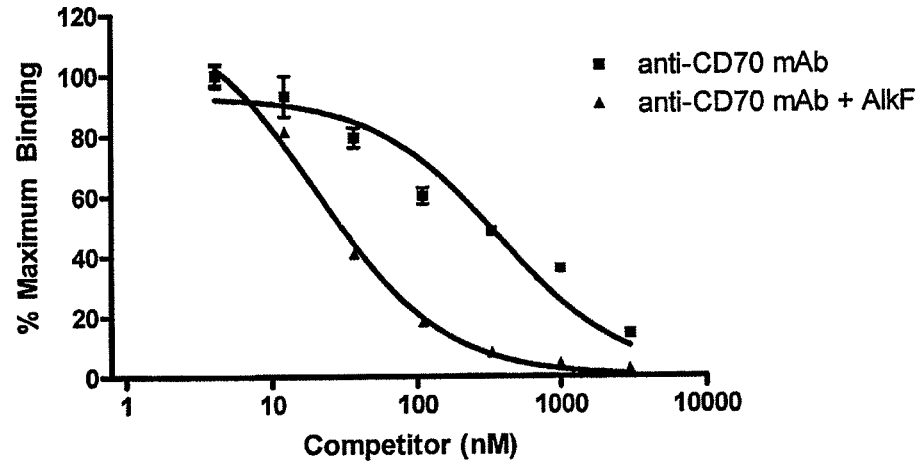

Non-core fucosylated anti-CD70 antibodies (triangles) competed for binding to huFcγ receptors (FIG. 3A) and muFcγ receptors (FIG. 3B) with fluorescently-labeled anti-CD70 parent antibody (squares). The non-core fucosylated anti-CD70 out-competed the parent (control) anti-CD70 antibody for binding to the murine receptor, muFcγRIV, with $EC_{50}$ values of 20.8 nM and 368.9 nM, respectively (an 18 fold difference). Non-core fucosylated anti-CD70 also out-competed the parent antibody in binding to the human receptor, huFcγRIIIA V158, with $EC_{50}$ values of 7.99 nM and 112.9 nM, respectively (a 14-fold difference).

Example 7

Expression of Other Antibodies in the Presence of Alkynyl Fucose Peracetate

To confirm the effect of alkynyl fucose peracetate on glycosylation of additional antibodies, antibodies were expressed from the following cell lines: CD70 Ab h1F6 in DG44 cells; CD19 Ab hBU12 in DG44 cells (see U.S. Provisional Application No. 61/080,169, filed Jul. 11, 2008); CD30 Ab cAC10 in DG44 cells; and CD33 Ab HuM195 in SP2/0 and CHO-K1 cell (see also U.S. Ser. No. 12/253,895, filed Oct. 17, 2008). Briefly, the cell lines were initially cultured at $3.0 \times 10^5$ cells per mL in 30 mLs of CHO selection media at 37° C., 5% $CO_2$ and shaking at 100 RPM. The media was supplemented with insulin like growth factor (IGF), penicillin, streptomycin and 50 μM alkynyl fucose peracetate, as described. The cultures were fed on day 3 with 2% volume of feed media containing 2.5 mM alkynyl fucose peracetate. On day four, the cultures were split 1:4 into fresh culture media. Cultures were fed with a 6% volume of feed media containing 833 μM alkynyl fucose peracetate on days 5, 7, 9 and 10. Conditioned media was collected on day 13 by passing the culture through a 0.2 μm filter.

Antibody purification was performed by applying the conditioned media to a protein A column—pre-equilibrated with 1× phosphate buffered saline (PBS), pH 7.4. Antibodies were eluted with 5 column volumes of Immunopure IgG elution buffer (Pierce Biotechnology, Rockford, Ill.). A 10% volume of 1M tris pH 8.0 was added to the eluted fraction. The sample was dialyzed overnight into 1×PBS.

Figure 4:
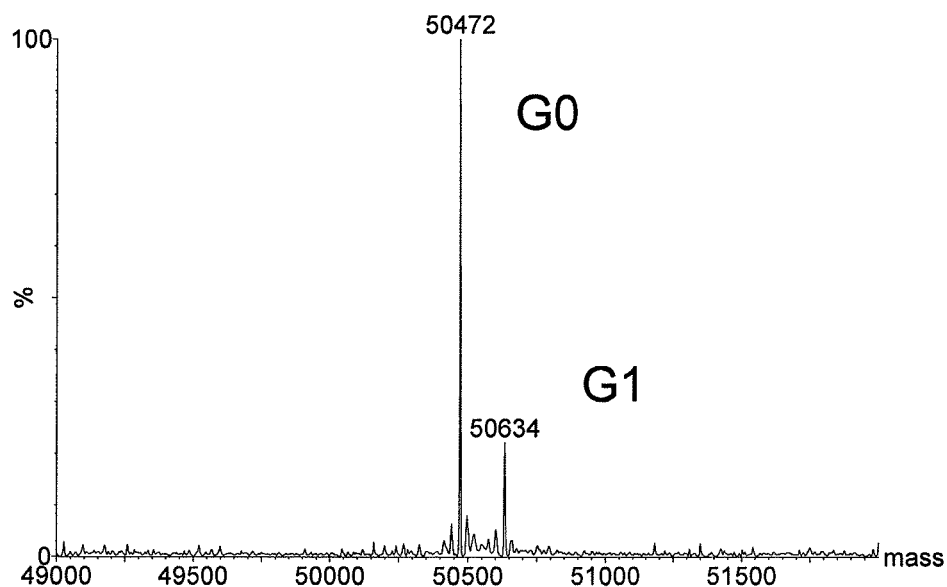
FIG. 4 shows the results of LC-MS (Q-T of) analysis of four antibodies cultured in the absence or presence of alkynyl fucose peracetate (upper and lower portions, respectively, of each pair of panels). G0, G1 and G0-F are as indicated supra. "G1-F" refers to the carbohydrate structure where one of the non-reducing termini has a galactose and there is no core fucosylation (a mixture of two isomers).
Figure 4:
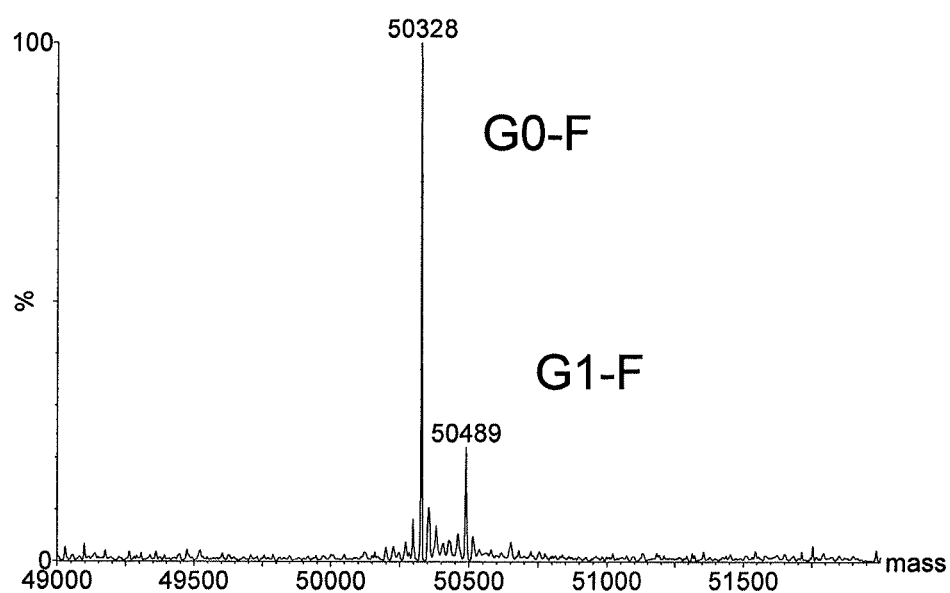
Figure 4:
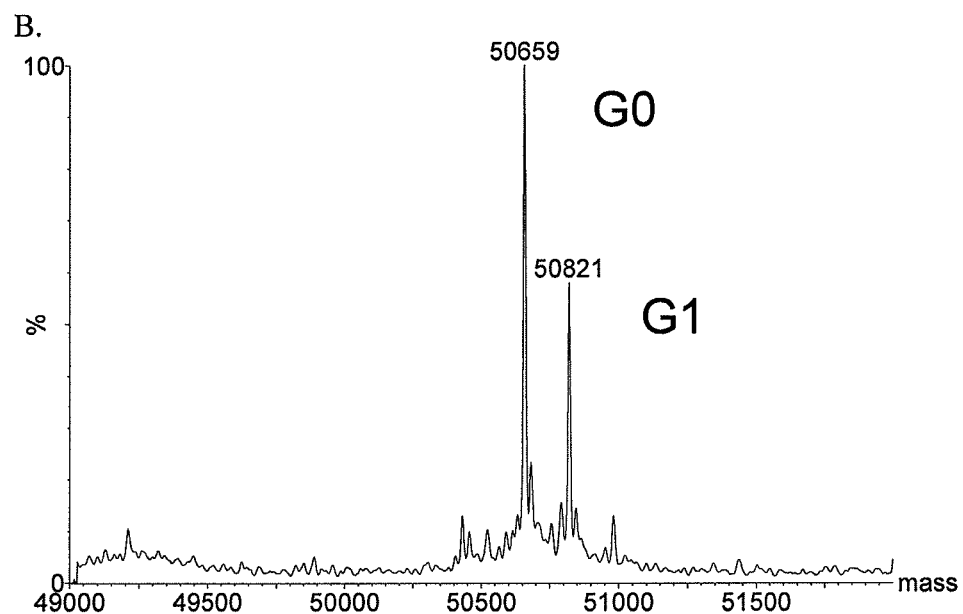
Figure 4:
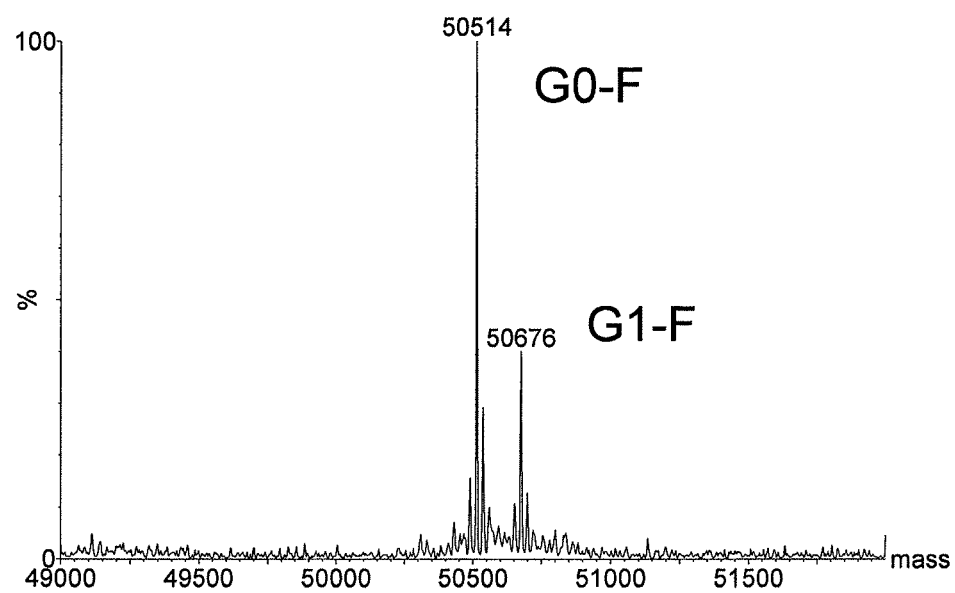
Figure 4:
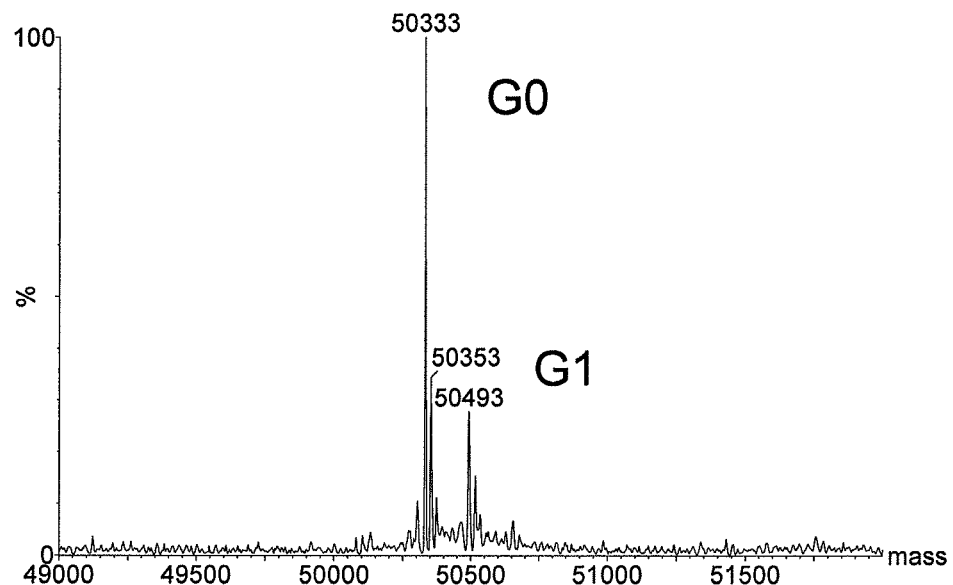
Figure 4:
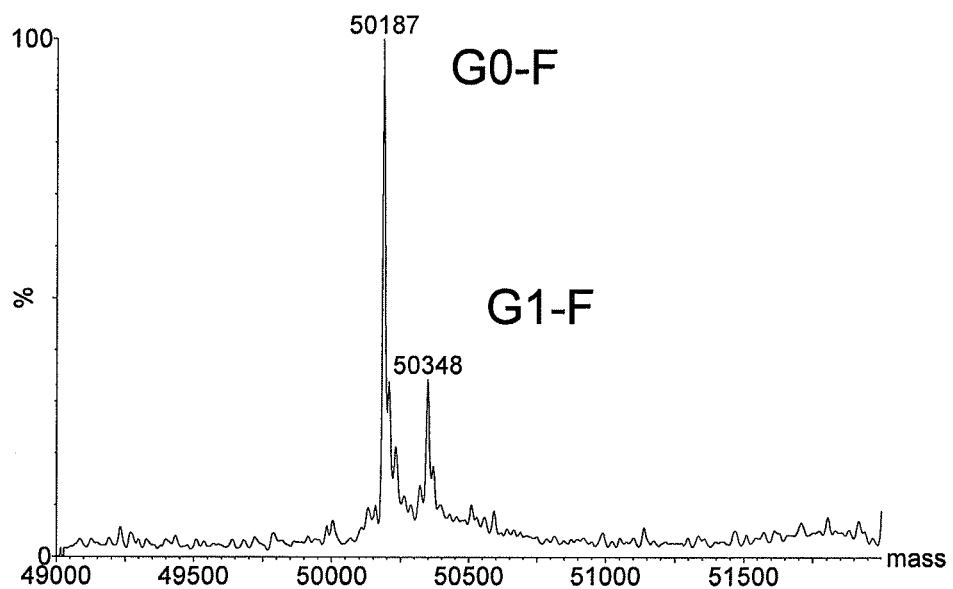
Figure 4:
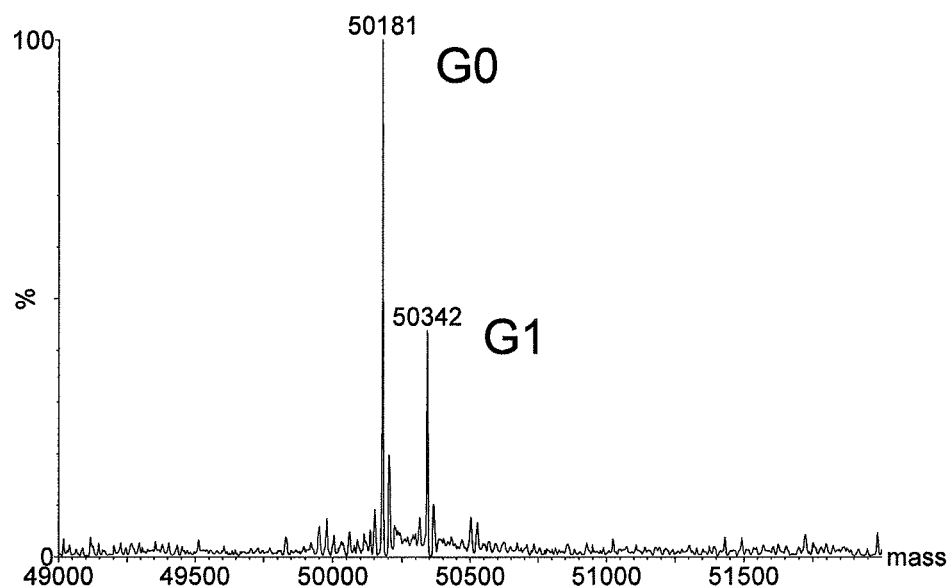
Figure 4:
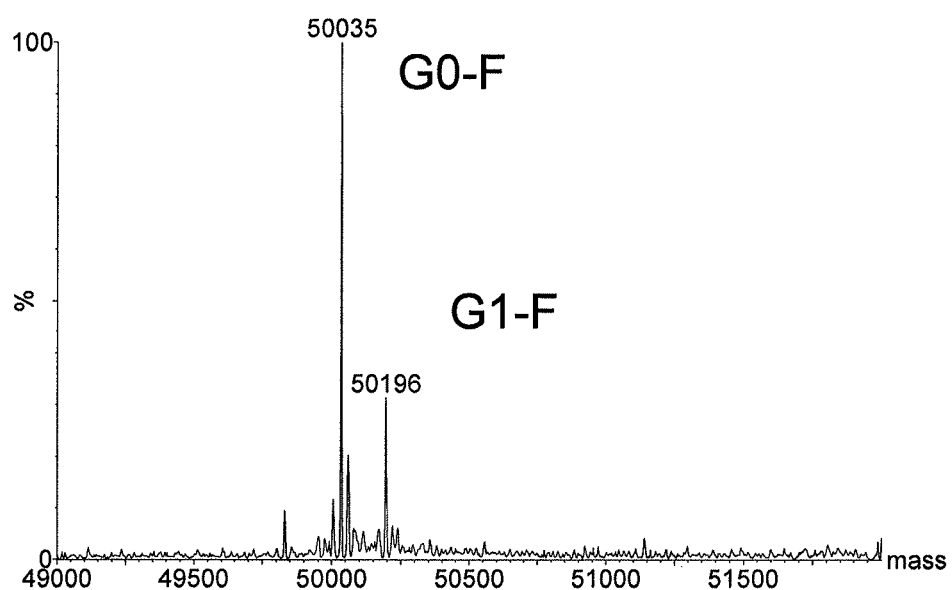

Qtof analysis of the antibodies revealed similar results to those of Example 3. Relative to heavy chains of antibodies produced from host cells grown in the absence of alkynyl fucose peracetate, heavy chains of antibodies from cells grown in the presence of alkynyl fucose peracetate were observed to decrease by about 146 Da, consistent with the absence of fucose. Referring to FIG. 4, for the G0 peak (no galactose) for each antibody, the observed shift in mass between heavy chain from cells grown in the absence and presence of alkynyl fucose peracetate (upper and lower portions of each panel) was a decrease of 144 Da (anti-CD70 antibody, FIG. 4A), 145 Da (anti-CD19 antibody, FIG. 4B), 146 Da (anti-CD30 antibody, FIG. 4C), and 146 Da (anti-CD33 antibody, FIG. 4D). These decreases in molecular weight are inconsistent with loss of any other sugar found in antibody carbohydrate other than fucose: mannose and galactose, 162 Da, N-acetylglucosamine, 203 Da, and sialic acid, 291 Da.

Example 8

Effector Function Assays

The effector functions, ADCC and ACCP, of a non-core fucosylated, humanized CD19 antibody, hBU12, was determined. ADCC activity was generally measured as described in Example 5 using Ramos cells. NK cells were isolated from individuals with 158V and 158F FcγRIIIa phenotypes.

Antibody-dependent cellular phagocytosis (ADCP) was assessed using a previously described method (see McEachern et al., Blood 109:1185 (2007)). Briefly, target Ramos cells were incubated with the fluorescent dye PKH26 (Sigma, St. Louis, Mo.) prior to addition of the antibody and primary human macrophages. Macrophages were generated from normal human PBMCs cultured for 10 to 14 days with 500 U/ml human G-MCSF (PeproTech, Rocky Hill, N.J.). After a 1 h incubation at 37° C., the macrophages were labeled with a FITC-conjugated CD11b antibody (BD Pharmingen). Uptake of the target cells by the macrophages (phagocytosis) was assessed by flow cytometry and visualized by immunofluorescence using a Carl Zeiss Axiovert 200M microscope. Specific phagocytosis was determined by correcting for the hIgG1 background values.

Figure 5:
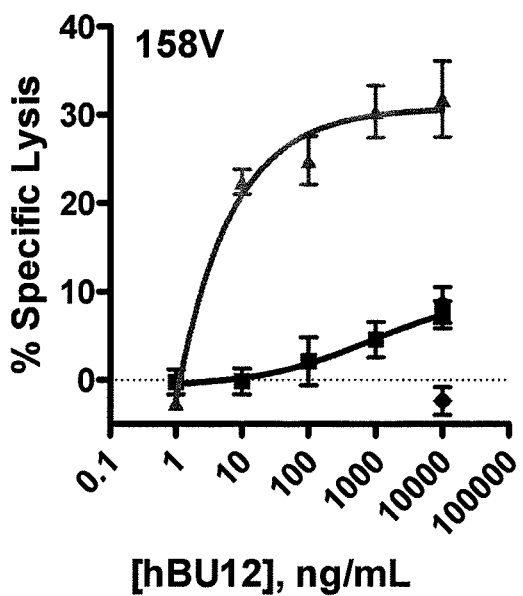
FIG. 5 shows the results of effector function (ADCC) assays of a humanized CD19 antibody cultured in the absence or presence of alkynyl fucose peracetate (core fucosylated (squares) or non-core fucosylated (triangles), respectively) on NK cells having the 158V and 158F phenotypes (panels A and B, respectively).
Figure 5:
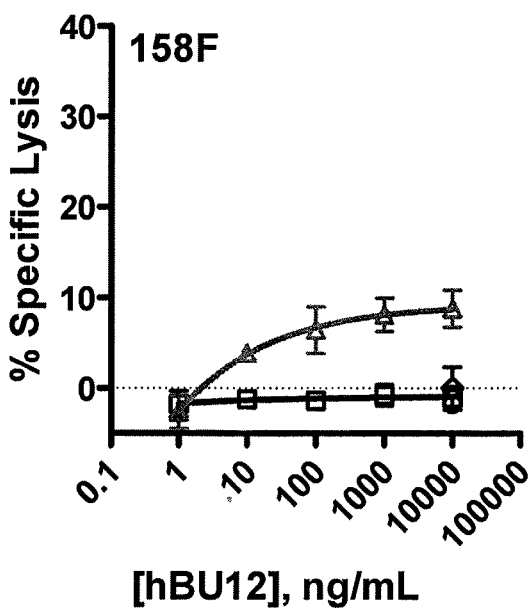

Referring to FIGS. 5A and 5B, the non-core fucosylated CD19 antibody (closed triangles) exhibited an approximately 100-fold increase in $EC_{50}$ in the 158 V background, with a 3.5-fold increase in maximum target cell lysis, as compared with the control (core fucosylated) antibody (closed squares). In the 158F background, the non-core fucosylated CD19 antibody (open triangles) had a 100 fold increase in $EC_{50}$ and a 10-fold increase in maximum target cell lysis, as compared with the control (core fucosylated) antibody. In contrast, no change in ACDP activity was observed between the non-core fucosylated and control antibody (data not shown).

Example 9

Expression of Antibodies from Hybridomas

Three antibody expressing hybridoma lines were tested to determine the effect of alkynyl fucose peracetate on antibody core fucosylation from these cell lines. These hybridomas were: 1) a BALB/C mouse spleen cell and a P2X63-AG 8.653 mouse myeloma cell fusion expressing the chimeric anti-ley antigen antibody BR96; 2) a BALB/C mouse spleen cell and a NS0 mouse myeloma cell fusion expressing a murine anti-Liv1 antibody; and 3) a BALB/C mouse spleen cell and a SP2/0 mouse myeloma cell fusion expressing a murine anti-Liv-1 antibody. These hybridomas were cultured at $3.0 \times 10^5$ cells per mL in 30 mLs of Hybridoma Serum Free Media (Invitrogen, Carlsbad Calif.) supplemented with 50 μM alkynyl fucose peracetate at 37° C., 5% $CO_2$ and shaking at 100 RPM in a 125 mL shake flask. Cultures were fed on day 3 with 2% volume of a feed media. On day four, the culture was split 1:4 into fresh culture media. Cultures were fed with a 6% volume of feed media on days 5, 7, 9 and 10. Conditioned media was collected when the viability of the culture dropped below 60% or on day 13 by passing culture through a 0.2 μm filter.

Antibody purification was performed by applying the conditioned media to a protein A column pre-equilibrated with 1× phosphate buffered saline (PBS), pH 7.4. After washing column with 20 column volumes of 1×PBS, antibodies were eluted with 5 column volumes of Immunopure IgG elution buffer (Pierce Biotechnology, Rockford, Ill.). A 10% volume of 1M tris pH 8.0 was added to eluted fraction. The sample was dialyzed overnight into 1×PBS.

At the concentration of alkyl fucose peracetate tested, core fucosylation was inhibited in the hybridoma from the BALB/C-SP2/0 fusion, but not the BALB/C/P2X63-AG 8.653 and NS0 fusions.

Example 10

Synthesis of 5-Ethynylarabinose Tetraacetate (7)

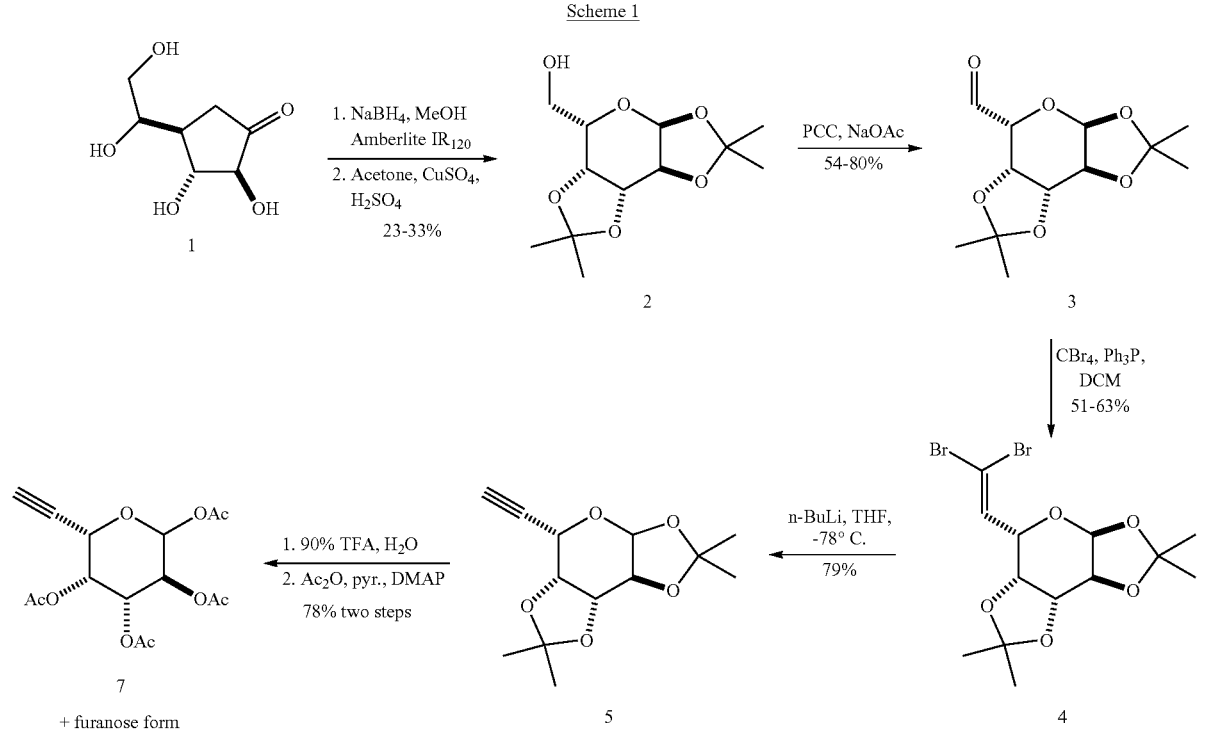

Scheme 1

1,2:3,4-Di-O-isopropylidene-α-L-galactose (2)

The compounds in Scheme 1 were generally prepared as described by Hsu et al., *Proc. Natl. Acad. Sci. USA* 104:2614-19 (2004). Briefly, L-galactono-1,4-lactone (1) (10 g, 56.1 mmol) in $CH_3OH$ (60 ml) was combined with water (250.0 ml) at 0° C. and Amberlite IR 120 (H+) resin (10 g). $NaBH_4$ (1.0 equiv. 2.22 g, 56 mmol) was added portion wise over the course of 1 h (6 additions) with slow stirring. After $NaBH_4$ addition was complete, the reaction mixture was slowly stirred for 1 h at 0° C. and then stirred vigorously at 0° C. for 15 min to promote the decomposition of the remaining $NaBH_4$. The liquid was decanted, the resin washed with methanol (2×25 mL) and the solution concentrated under reduced pressure and then under high vacuum overnight resulting in the formation of a glass. To the resulting solid was added acetone (220.0 ml), $CuSO_4$ (22 g) and $H_2SO_4$ (2 ml) and the solution was stirred vigorously at room temperature for at least 24 h. After 24 h, inspection by TLC (50% ethyl acetate in hexanes) showed product formation by staining with vanillin dip stain and heat ($R_f$~0.5). The reaction mixture was neutralized with $Ca(OH)_2$ or $Cu(OH)_2$ (~15 g) and vacuum filtered. The residue was purified by flash radial chromatography with a gradient elution from 10% to 50% ethyl acetate in hexanes. Clean fractions were combined to afford 3.3 g; (23%): $^1H$ NMR ($CD_3OD$, 400 MHz) δ: 5.48 (d, J=4.5 Hz, 1H), 4.62 (dd, J=7.8, 2.3 Hz, 1H), 4.24 (dd, J=4.9, 2.3 Hz), 4.27 (dd, J=8.0, 1.8 Hz), 3.85 (m, 1H), 3.64 (m, 2H), 1.51 (s, 3H), 1.39 (s, 3H), 1.32 (s, 6H).

1,2:3,4-di-O-isopropylidene-α-L-galactal pyranoside (3)

A suspension of pyridinium chlorochromate (PCC) (8.2 g, 38 mmol), sodium acetate (6.2 g, 76 mmol) and 4-Å molecular sieves (16 g) in dry methylene chloride (114 ml) was stirred for 1 h. To this mixture was added a solution of the alcohol (Compound 2) (3.3 g, 12.7 mmol) in dry methylene chloride (57 ml) drop-wise, and the mixture was stirred at room temperature for 2 h. The reaction mixture was diluted with hexane/ether (1:1, 300 ml), and the solution was filtered through a bed of silica gel. The filter pad was washed with ethyl acetate (200 mL). The filtrate was concentrated under reduced pressure and high vacuum overnight to give 2.9 g (88%): $^1H$ NMR($C_6D_6$; 400 MHz) δ 9.61 (s, 1H), 5.44 (d, J=5.1 Hz, 1H), 4.27 (dd, J=2.3 Hz, 1H), 4.24 (dd, J=2.3 Hz, 1H), 4.13 (d, J=2.3 Hz, 1H), 4.04 (dd, J=2.3 Hz, 1H), 1.32 (s, 3H), 1.2 (s, 3H), 0.98 (s, 3H), 0.93 (s, 3H).

Dibromo-olefin (4)

To a flame-dried 25 mL round-bottom flask was added $CBr_4$ (2.38 g, 7.14 mmol) and methylene chloride (50 mL). The solution was cooled to 0° C. and $Ph_3P$ (3.71 g, 14.3 mmol) was added. The mixture was stirred for 15 min, and the aldehyde (Compound 3) (0.62 g, 2.38 mmol) was added as a solution in methylene chloride (5 mL). The reaction was monitored by TLC. After 5 min., the reaction was complete. The mixture was concentrated under reduced pressure to approximately 5 mL and this was directly purified by flash column chromatography with 10% followed by 25% ethyl acetate in hexanes. The product-containing fractions (stains dark purple with vanillin stain ($R_f$=0.5 in 25% ethyl acetate in hexanes)) were combined and concentrated to give 495 mg. (51%): $^1$H NMR (CDCl$_3$; 400 MHz) δ: 6.86 (d, J=8.2 Hz, 1H), 5.39 (d, J=4.9 Hz, 1H), 4.62 (dd, J=8.0, 1.8 Hz, 1H), 4.37 (dd, J=7.8, 2.3 Hz), 4.03 (dd, J=5.1, 2.5 Hz, 1H), 3.90 (dd, J=5.8, 2.0 Hz, 1H), 1.1 (s, 3H), 1.0 (s, 3H), 0.67 (s, 3H), 0.63 (s, 3H).

6,7-Deoxy-1,2:3,4-di-O-isopropylidene-α-L-galacto-hept-6-ynopyranoside (5)

To the dibromo olefin (Compound 4) (500 mg, 1.2 mmol) in THF (15 mL) at −78° C. was added n-BuLi (3.0 mL of a 1.6M solution in hexanes; 4.87 mmol) and the reaction was stirred for 1 h before being treated with a solution of ammonium chloride. The layers were separated and the aqueous was extracted with hexanes (3×50 mL). The combined extracts were washed with brine and dried over Na$_2$SO$_4$, filtered and concentrated. The resulting residue was purified via radial chromatography to give 483 mg (79%): $^1$H NMR (CDCl$_3$; 400 MHz) δ: 5.39 (d, J=5.0 Hz, 1H), 4.69 (t, J=2.3 Hz, 1H), 4.36 (dd, J=7.6, 2.5 Hz), 4.01 (dd, J=5.0, 2.5 Hz, 1H), 3.94 (dd, J=7.6, 2.0 Hz, 1H), 2.01 (d, J=2.3 Hz, 1H), 1.50 (s, 3H), 1.23 (s, 3H), 1.11 (s, 3H), 0.92 (s, 3H).

5-ethynylarabinose (6)

To a flask containing the alkyne (Compound 5) (0.483 g, 1.9 mmol), TFA solution (10 ml, 90% TFA in H$_2$O) was slowly added at 0° C. The reaction was stirred on ice for 1 h and concentrated in vacuo.

5-ethynylarabinose tetraacetate (7)

(General Procedure) The resulting residue of 5-ethynylarabinose (Compound 6) was treated with pyridine (10 ml), N,N,-dimethylaminopyridine (5.0 mg), and acetic anhydride (10 ml), stirred overnight, concentrated to a residue and diluted with dichloromethane. The mixture was aspirated onto a 4 mm radial chromatotron plate and eluted with 25% followed by 50% ethyl acetate in hexanes. The product was isolate as an inseparable mixture of pyranose and furnanose α and β-anomers. Yield: 495 mg (76%): LRMS (ESI$^+$) m/z 365 (M+Na)$^+$, 283 (M-OAc)$^+$

Example 11

Synthesis of 6-Methyl-L-galactose pentaacetate

Scheme 2

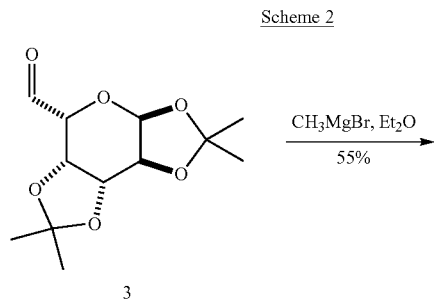

3

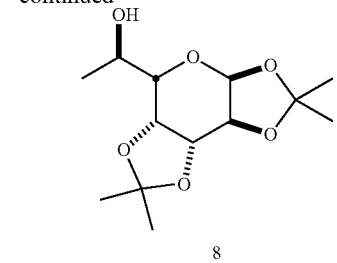

8

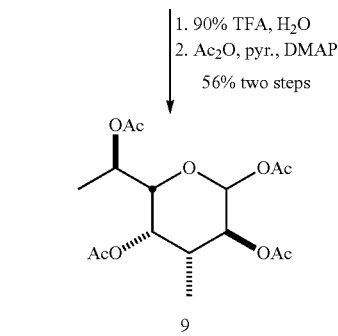

9

1,2:3,4-di-O-isopropylidene-α-L-6-methylgalactopyranoside (8)

Referring to Scheme 2, to a flame-dried flask was added ether (2 mL) and CH$_3$MgBr (258 μL of a 3M solution). This was followed by the addition of the aldehyde (Compound 3) (100 mg) in ether (2 mL), added drop-wise. The reaction mixture was stirred at room temperature for several hours and was monitored by TLC. The reaction mixture was quenched with saturated aqueous ammonium chloride and the mixture was extracted with ether (3×50 mL). The combined extracts were washed with water and brine and dried over MgSO$_4$. Filtration and concentration gave a residue that was analyzed by $^1$H NMR revealing a diastereomeric mixture. The residue was purified via radial chromatography on a 1 mm plate eluting with 10% to 25% ethyl acetate in hexanes ($R_f$=0.2; 25% ethyl acetate in hexanes). The yield was 59 mg (55%): $^1$H NMR-major isomer (CDCl$_3$; 400 MHz) δ: 5.61 (d, 1H), 4.62 (dd, 1H), 4.38 (d, 1H), 4.73 (dd, 1H), 4.04 (m, 1H), 1.56 (s, 3H), 1.50 (s, 3H), 1.37 (s, 3H), 1.28 (d, 3H).

6-Methyl-L-galactose pentaacetate (9)

Compound 9 was prepared from Compound 8 by following the general procedure for acetonide hydrolysis and peracetylation in Example 10. LRMS (ESI$^+$) m/z 345 (M-OAc)$^+$.

Example 12

Synthesis of L-galactose pentaacetate

Scheme 3

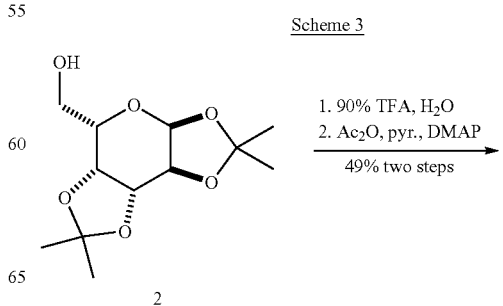

2

-continued

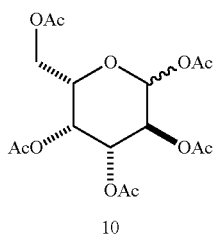

L-galactose pentaacetate (10)

Compound 10 was synthesized from Compound 2 following the general procedure for acetonide hydrolysis and peracetylation in Example 10. (49% overall): LRMS (ESI$^+$) m/z 331 (M-OAc)$^+$.

Example 13

Synthesis of 5-vinylarabinose tetraacetate

Scheme 4

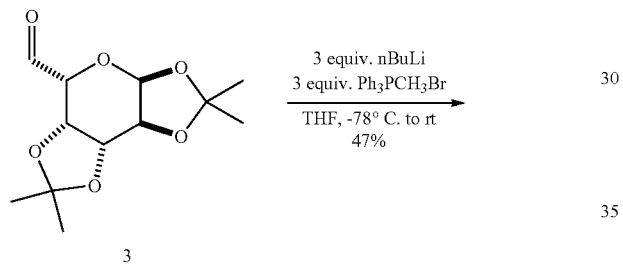

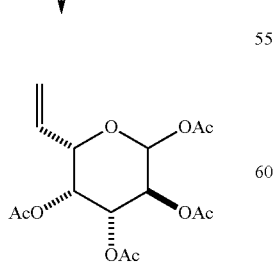

6,7-Deoxy-1,2:3,4-di-O-isopropylidene-α-L-galacto-hept-6-enopyranoside (11)

Referring to Scheme 4, to a −78° C. solution of Ph$_3$PCH$_3$Br (192 mg, 0.54 mmol) in THF (2 mL) was added n-BuLi (0.34 mL of a 1.6M solution in THF; 0.54 mmol). The mixture was stirred at −78° C. for 15 min, followed by the addition of aldehyde (Compound 3) (46.3 mg, 0.18 mmol). The mixture was allowed to warm to an ambient temperature over 1.5 h before being diluted with diethyl ether (25 mL) and quenched with saturated aqueous ammonium chloride (25 mL). The organic layer was washed with brine, dried over magnesium sulfate, filtered and concentrated under reduced pressure. The resulting residue was purified on silica gel (10% ethyl acetate in hexane; TLC R$_f$=0.56 25% ethyl acetate in hexanes) to give 22.8 mg (49%): $^1$H NMR (CDCl$_3$; 400 mHz) δ: 5.93 (ddd, 1H), 5.59 (d, 1H), 5.37 (dt, 1H), 5.28 (dt, 1H), 4.62 (dd, 1H), 4.31 (m, 2H), 4.23 (dd, 1H), 1.54 (s, 3H), 1.47 (s, 3H), 1.35 (s, 3H).

5-vinylarabinose tetraacetate (12)

Compound 12 was prepared from Compound 11 following the general procedure for acetonide hydrolysis and peracetylation of Example 10. Yield: 62% overall.

Example 14

Synthesis of 5-(1-propynyl)-arabinose tetraacetate

Scheme 5

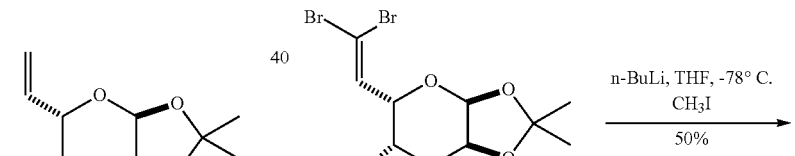

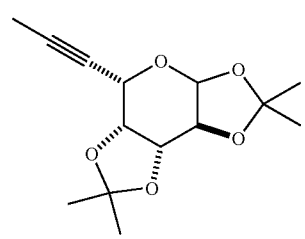

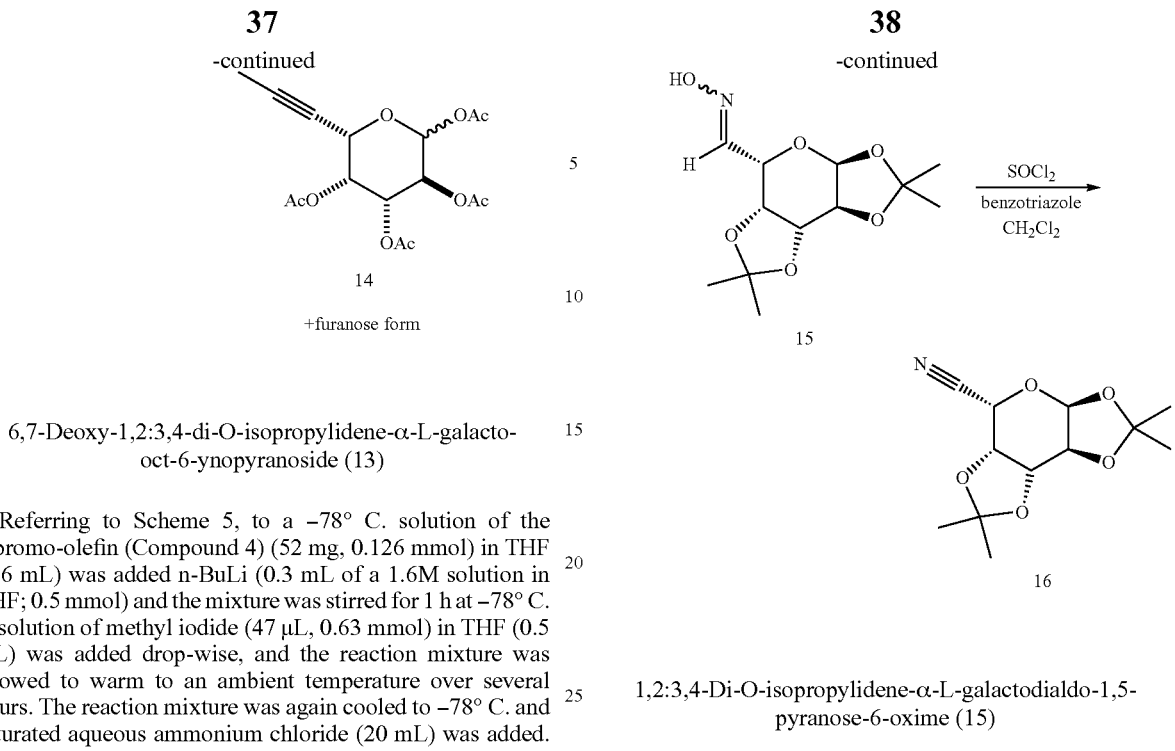

6,7-Deoxy-1,2:3,4-di-O-isopropylidene-α-L-galacto-oct-6-ynopyranoside (13)

Referring to Scheme 5, to a −78° C. solution of the dibromo-olefin (Compound 4) (52 mg, 0.126 mmol) in THF (1.6 mL) was added n-BuLi (0.3 mL of a 1.6M solution in THF; 0.5 mmol) and the mixture was stirred for 1 h at −78° C. A solution of methyl iodide (47 μL, 0.63 mmol) in THF (0.5 mL) was added drop-wise, and the reaction mixture was allowed to warm to an ambient temperature over several hours. The reaction mixture was again cooled to −78° C. and saturated aqueous ammonium chloride (20 mL) was added. The resulting mixture was extracted with ethyl acetate (3×20 mL) and the combined organics were washed with saturated aqueous sodium chloride, dried of magnesium sulfate, filtered and concentrated under reduced pressure. The resulting residue was purified on silica gel eluting with 10% ethyl acetate in hexanes to give 16.9 mg (50%) of product as an oil.

5-(1-propynyl)-arabinose-1,2,3,4-tetraacetate (14)

Compound 14 was prepared from Compound 13 following the general procedure for acetonide hydrolysis and peracetylation in Example 10. Yield: 58% overall.

Example 15

Synthesis of 5-cyano-arabinopyranose-1,2,3,4-tetraacetate and 5-cyano-arabinofuranose-1,2,3,5-tetraacetate Scheme 6

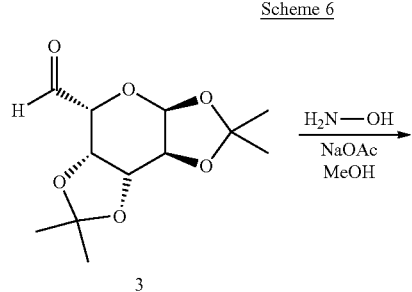

1,2:3,4-Di-O-isopropylidene-α-L-galactodialdo-1,5-pyranose-6-oxime (15)

Compound 15 was generally prepared as described by Streicher and Wunsch, *Carbohydr Res.* 338(22):2375-85 (2003). Referring to Scheme 6, the aldehyde (Compound 3) (200 mg, 0.77 mmol), hydroxylamine hydrochloride (161 mg, 2.32 mmol, 3.0 eq.), and NaOAc (127 mg, 1.55 mmol, 2.0 eq.) were diluted in MeOH (10 mL, 0.1 M) followed by the addition of water (1 mL, 10% v/v). The reaction stood for 20 h. The mixture was concentrated down to the aqueous layer to which it was extracted with ether (2×). The combined organics were extracted with NaOH (1×), and the aqueous layer acidified to pH 4-5 with 1 M HCl. The aqueous phase was extracted with ether (3×). The $Et_2O$ layer was dried ($MgSO_4$) and concentrated in vacuo to provide the product as a white crystalline solid. Yield: (164 mg, 78%). LRMS ($ESI^+$) m/z 274.1 $(M+H)^+$. $^1H$-NMR ($CDCl_3$) δ: 1:1 mixture of (E):(Z) oxime isomers was detected. 1.33 (s, 12H), 1.46 (s, 6H), 1.54 (s, 3H), 1.55 (s, 3H), 4.29 (dd, J=2.0 Hz, 8.0 Hz, 1H), 4.34-4.36 (m, 2H), 4.43 (dd, J=2.0 Hz, 6.4 Hz, 1H), 4.62-4.63 (m, 3H), 5.00 (d, J=4.0 Hz, 1H), 5.55 (d, J=4.8 Hz, 2H), 6.80 (d, J=4.4 Hz, 1H), 7.46 (d, J=6.0 Hz, 1H).

5-cyano-fucose diacetonide (16)

Compound 16 was generally prepared as described by Telvekar, *Synthetic Communications* 34(13):2331-2336 (2004). The oxime isomers (Compound 15) (160 mg, 0.5 mmol) were dissolved in $CH_2Cl_2$ (2 mL, 0.4 M). To this was added a solution of benzotriazole (70 mg, 0.5 mmol) and thionyl chloride (43 μL, 0.5 mmol) in 0.5 mL of $CH_2Cl_2$. The reaction was complete by TLC analysis in 5 min. The contents were filtered and the filtrate washed with sat. $NaHCO_3$ and water. The organic phase was dried ($Na_2SO_4$), filtered and evaporated. The crude product was purified by FCC eluting with 4:1 hexanes-EtOAc. Yield: 120 mg (81%). LRMS ($ESI^+$) m/z 256.1 $(M+H)^+$. $^1H$-NMR ($CDCl_3$) δ: 1.35 (s, 3H), 1.39 (s, 3H), 1.54 (s, 3H), 1.55 (s, 3H), 4.34 (dd, J=2.0 Hz, 7.6 Hz, 1H), 4.38 (dd, J=2.8 Hz, 4.8 Hz, 1H), 4.66 (m, 2H), 5.54 (d, J=5.2 Hz, 1H).

5-Cyano-arabinopyranose-1,2,3,4-tetraacetate (19) and 5-cyano-arabinofuranose-1,2,3,5-tetraacetate (20)

Compounds 19 and 20 were prepared from Compound 16 following the general procedure for acetonide hydrolysis and peracetylation of Example 10. The resulting pyranose and furanose forms were separable by FCC (elution gradient—4:1 to 3:2 hexanes-EtOAc). Sequence of elution by TLC: pyranose (Rf 0.34), furanose (Rf. 27) in 3:2 hexane-EtOAc. Yield: 59 mg (pyranose), 52 mg (furanose) (98% combined overall yield). LRMS (ESI$^+$) m/z 0.284.1 (M-OAc)$^+$, 366.0 (M+Na)$^+$. $^1$H-NMR assignments were analogous to the alkynyl fucose reported by Hsu et al. (Hsu, Hanson et al., 2007; supra). $^1$H-NMR summary of pyranose forms (CDCl$_3$) δ: 5.89 (d, J=4.0 Hz, 1H, β-pyr), 6.42 (d, J=2.8 Hz, 1H, α-pyr). $^1$H-NMR summary of furanose forms (CDCl$_3$) δ: 6.27 (s, 1H, α-fur), 6.38 (d, J=4.8 Hz, 1H, β-fur).

Example 16

Synthesis of Chloro-, Bromo- and Iodo-Fucose Tetraacetates

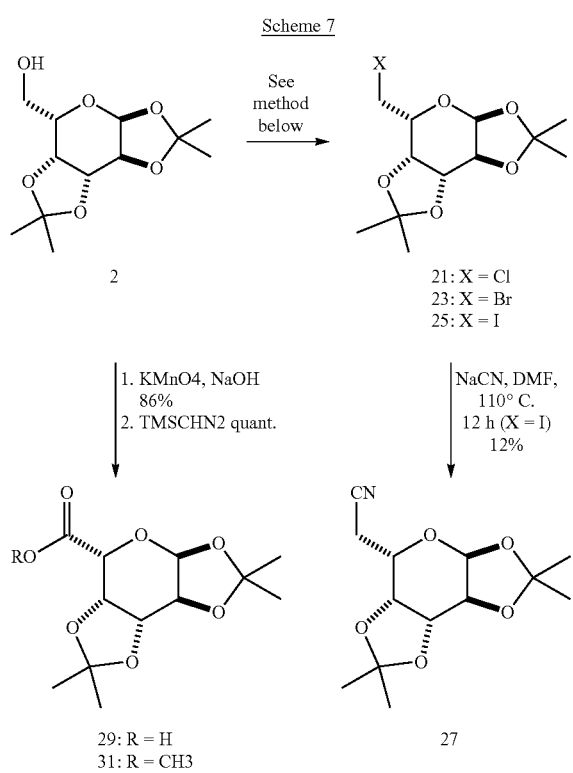

Scheme 7

6-Chloro-fucose diacetonide (21)

Referring to Scheme 7, the alcohol (Compound 2) (100 mg, 0.384 mmol), CCl$_4$ (1 mL, 10 mmol), and PPh$_3$ (300 mg, 1.15 mmol, 3 eq.) were dissolved in CHCl$_2$ (2 mL). The contents were stirred for 24 h following by concentration. The residue was purified by FCC (9:1 hexanes-EtOAc) to afford the product as a pale yellow gel. Yield: 107 mg (55%). LRMS (ESI$^+$) m/z 279 (M+H)$^+$. $^1$H-NMR (CDCl$_3$) δ: 1.34 (s, 3H), 1.36 (s, 3H), 1.45 (s, 3H), 1.54 (s, 3H), 3.58 (dd, J=6.8 Hz, 10.8 Hz, 1H), 3.68 (dd, J=6.8 Hz, 10.8 Hz, 1H), 4.65 (dd, J=2.4 Hz, 7.6 Hz, 1H), 5.54 (d, J=5.2 Hz).

6-Chloro-fucose tetraacetate (22)

Compound 22 was prepared from Compound 21 following the general procedure for acetonide hydrolysis and peracetylation of Example 10. Yield: 29 mg (38% overall). LRMS (ESI$^+$) m/z 307.1 (M-OAc)$^+$, 389.0 (M+Na)$^+$.

6-Bromo-fucose diacetonide (23)

Referring to Scheme 7, the alcohol (Compound 2) (150 mg, 0.58 mmol) was dissolved in DMF (2 mL) followed by addition of PPh$_3$ (0.61 g, 2.3 mmol, 4 eq.). N-bromosuccinimide (0.41 g, 2.3 mmol, 4 eq.) in DMF (1 mL) was added over 5 min via syringe. The mixture was heated to 110° C. for 2 h. The reaction was cooled and quenched with MeOH and stirred for 10 min. Ether and sat. NaHCO$_3$ were added and the layers separated. The aqueous layer was further washed with ether and the combined organic extracts were washed with water and dried (Na$_2$SO$_4$). The solvent was evaporated and the residue purified by FCC (9:1 hexanes-EtOAc) to afford the product as a sticky solid. Yield: 123 mg (66%). LRMS (ESI$^+$) m/z 323 (M+H)$^+$. $^1$H-NMR (CDCl$_3$) δ: 1.34 (s, 3H), 1.36 (s, 3H), 1.45 (s, 3H), 1.55 (s, 3H), 3.43 (dd, J=6.8 Hz, 10 Hz, 1H), 3.52 (dd, J=6.8 Hz, 10.4 Hz, 1H), 3.98 (dt, J=2.0 Hz, 6.8 Hz, 1H), 4.33 (dd, J=2.4 Hz, 5.2 Hz, 1H), 4.38 (dd, J=2.0 Hz, 8.0 Hz, 1H), 4.64 (dd, J=2.4 Hz, 8.0 Hz, 1H), 5.55 (d, J=5.2 Hz).

6-Bromo-fucose tetraacetate (24)

Compound 24 was prepared from Compound 23 following the general procedure for acetonide hydrolysis and peracetylation of Example 10. Yield: 129 mg (86% overall). LRMS (ESI$^+$) m/z 351.0 (M-OAc)$^+$, 432.9 (M+Na)$^+$.

6-Indo-fucose diacetonide (25)

Referring to Scheme 7, the protected sugar (Compound 2) (0.44 g, 1.7 mmol), PPh$_3$ (0.99 g, 3.7 mmol, 2.2 eq.), iodine (0.87 g, 3.4 mmol, 2.0 eq.), and imidazole (0.51 g, 7.4 mmol, 4.4 eq.) were dissolved in toluene/EtOAc (4 mL/2 mL). The mixture was heated to 90° C. for 6 h while stirring. The mixture was cooled in an ice bath, diluted with CHCl$_3$ and extracted with sat. NaHCO$_3$. The organic layer was dried (Na$_2$SO$_4$), filtered and concentrated to an oil. The residue was purified by FCC eluting with hexanes-EtOAc (95:5 to 90:10 gradient). The product was isolated as a clear oil. Yield: 0.27 g (43%). LRMS (ESI$^+$) m/z 371.1 (M+H)$^+$. $^1$H-NMR (CDCl$_3$) δ: 1.32 (s, 3H), 1.34 (s, 3H), 1.44 (s, 3H), 1.53 (s, 3H), 3.20 (dd, J=7.2 Hz, 9.6 Hz, 1H), 3.31 (dd, J=7.2 Hz, 9.6 Hz, 1H), 3.94 (dt, J=1.6 Hz, 7.2 Hz, 1H), 4.29 (dd, J=2.4 Hz, 5.0 Hz, 1H), 4.40 (dd, J=2.0 Hz, 8.0 Hz, 1H), 4.60 (dd, J=2.4 Hz, 7.8 Hz, 1H), 5.53 (d, J=4.8 Hz).

6-Iodo-fucose tetraacetate (26)

Compound 26 was prepared from Compound 25 following the general procedure for acetonide hydrolysis and peracetylation of Example 10. Yield: 30.5 mg (75% overall). LRMS (ESI$^+$) m/z 399.0 (M-OAc)$^+$.

Example 17

Synthesis of 6-cyano-fucose tetraacetate

6-Cyano-fucose diacetonide (27)

Compound 27 was prepared following a procedure by Streicher and Wunsch (*Carbohydr. Res.* 338(22): 2375-85 (2003)). Referring to Scheme 7, iodo-galactose (120 mg, 0.32 mmol) and NaCN (51 mg, 1 M) were heated to 110° C. in DMF for 12 h. The mixture was cooled, partitioned with $CH_2Cl_2$-water and the layers separated. The aqueous layer was further washed with $CH_2Cl_2$ (2×) and the combined organics washed with brine, dried ($Na_2SO_4$), filtered and concentrated to a brown oil. FCC purification (9:1 to 4:1 hexanes-EtOAc gradient) led to the pure product. Yield: 10 mg (12%). $^1$H-NMR ($CDCl_3$) δ: 1.33 (s, 3H), 1.35 (s, 3H), 1.45 (s, 3H), 1.54 (s, 3H), 2.65 (dd, J=6.8 Hz, 16 Hz, 1H), 2.70 (dd, J=6.8 Hz, 16 Hz, 1H), 4.05 (dt, J=2.0 Hz, 7.2 Hz, 1H), 4.24 (dd, J=2.0 Hz, 8.0 Hz, 1H), 4.34 (dd, J=2.8 Hz, 4.8 Hz, 1H), 4.65 (dd, J=2.8 Hz, 8.0 Hz, 1H), 5.50 (d, J=5.2 Hz).

6-Cyano-arabinose tetraacetate (28)

Compound 28 was prepared from Compound 27 following the general procedure for acetonide hydrolysis and peracetylation of Example 10. Yield: 13 mg (98% overall). LRMS ($ESI^+$) m/z 298.0 $(M-OAc)^+$, 380.1 $(M+Na)^+$.

Example 18

Synthesis of Carboxyfucose Tetraacetate

Carboxyarabinose diacetonide (29)

Following a procedure for the epimer (Bentama, El Hadrami et al., *Amino Acids* 24(4):423-6 (2003)), the alcohol (Compound 2) (3.44 g, 13.22 mmol) was diluted in 0.5 M NaOH (80 mL, 40 mmol, 3 eq.). After 15 min, $KMnO_4$ (5.22 g, 33.04, 2.5 eq.), dissolved in 106 mL of water, was added. The reaction stirred for 18 h and the solid filtered off. The filtrate was extracted with EtOAc (3×) and organic layers discarded. The aqueous layer was acidified with 1M HCl to pH 2 and extracted with EtOAc (3×). The combined organic layers were dried ($MgSO_4$), filtered, and concentrated to give a white solid that needed no further purification. Yield: 3.1 g (86%). LRMS ($ESI^-$) m/z 273.2 $(M-H)^-$. $^1$H-NMR ($CDCl_3$) δ: 1.36 (s, 6H), 1.46 (s, 3H), 1.54 (s, 3H), 4.40 (dd, J=2.4 Hz, 4.8 Hz, 1H), 4.70 (d, J=2.0 Hz, 1H), 4.64 (dd, J=2.4 Hz, 8.0 Hz, 1H), 5.50 (d, J=4.8 Hz).

Carboxyarabinose tetraacetate (30)

Compound 30 was prepared from Compound 29 following the general procedure for acetonide hydrolysis and peracetylation of Example 10.

Example 19

Synthesis of Carboxymethylarabinose Tetraacetate

Carboxymethylarabinose diacetonide (31)

The acid (Compound 29) (100 mg, 0.365 mmol) was dissolved in MeOH (3.65 mL, 0.1 M) and cooled to 0° C. After 15 min, 1 M $TMSCHN_2$ in ether (1.82 mL, 5 eq.) was added dropwise via syringe over 15 min. No starting material was detected after 30 min. The reaction was quenched with 5% HOAc/MeOH and the contents evaporated to dryness. Yield: Quant. LRMS ($ESI^+$) m/z 289.1 $(M+H)^+$. $^1$H-NMR ($CDCl_3$) δ: 1.34 (s, 6H), 1.46 (s, 3H), 1.53 (s, 3H), 3.83 (s, 3H), 4.39 (dd, J=2.4 Hz, 5.2 Hz, 1H), 4.59 (dd, J=2.4 Hz, 7.6 Hz, 1H), 4.67 (dd, J=2.4 Hz, 7.6 Hz, 1H), 5.67 (d, J=5.2 Hz).

Carboxymethyl-arabinose tetraacetate (32)

Compound 32 was prepared from Compound 31 following the general procedure for acetonide hydrolysis and peracetylation of Example 10. Yield: 105 mg (77% overall). LRMS ($ESI^+$) m/z 0.317.0 $(M-OAc)^+$, 398.9 $(M+Na)^+$.

Example 20

Synthesis of 5-methyl-oxiran-arabinose tetraacetate ((3S,4R,5S,6R)-6-((S)-2-methyloxiran-2-yl)-tetrahydro-2H-pyran-2,3,4,5-tetrayl tetraacetate) (36)

Scheme 8

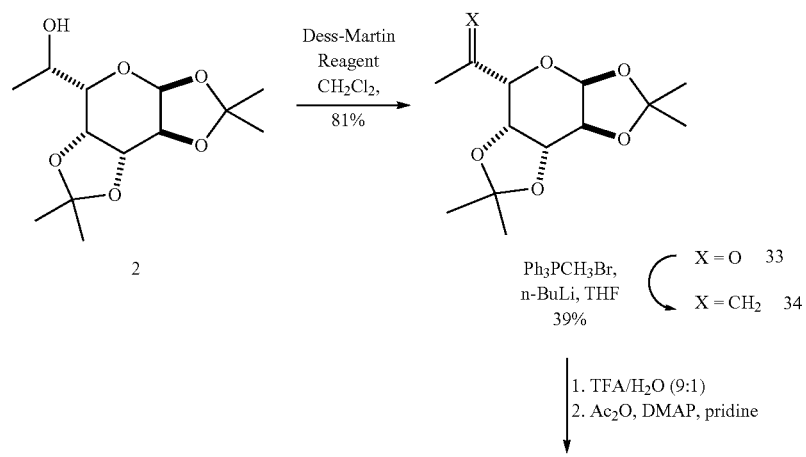

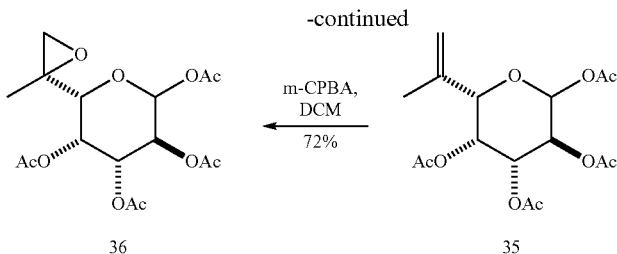

1-((3aS,5R,5aS,8aR,8bS)-2,2,7,7-tetramethyltetrahydro-3aH-bis[1,3]dioxolo[4,5-b:4',5'-d]pyran-5-yl)ethanone (33)

Referring to Scheme 8, to a mixture of the alcohol (Compound 2) (236 mg, 0.86 mmol) in DCM (10 mL) was added Dess-Martin periodinane (DMP; 438 mg, 1.03 mmol)). After several hours an additional portion DMP (100 mg, 0.23 mmol) was added, and the mixture was stirred for an additional 1 h. The mixture was directly aspirated onto a 1 mm radial chromatotron plate and eluted with 25% ethyl acetate in hexanes. The first major material off the plate was desired product (Rf=0.6; 25% ethyl acetate in hexanes). Yield: 190 mg (81%): LRMS (ESP) m/z 272; $^1$H-NMR (CDCl$_3$) δ: 5.64 (d, J=5.1 Hz, 1H), 4.63 (dd, J=7.8, 2.6 Hz, 1H), 4.55 (dd, J=7.8, 2.3 Hz), 4.35 (dd, J=5.1, 2.5 Hz), 4.17 (d, J=2.0 Hz, 1H), 2.26 (s, 3H), 1.5 (2, 3H), 1.44 (s, 3H), 1.34 (s, 3H), 1.31 (s, 3H).

(3aS,5S,5aR,8aR,8bS)-2,2,7,7-tetramethyl-5-(prop-1-en-2-yl)tetrahydro-3aH-bis[1,3]dioxolo[4,5-b:4',5'-d]pyran (34)

Referring again to Scheme 8, Compound 34 was prepared from Compound 33 (50 mg, 0.18 mmol) in a fashion similar to that used in preparation of Compound 11, to give 19 mg (39%): $^1$H-NMR (CDCl$_3$) δ: 5.61 (d, J=5.1 Hz, 1H), 5.10 (d, J=2.1 Hz, 1H), 4.99 (dd, J=3.1, 1.6 Hz, 1H), 4.34 (m, 2H), 4.19 (s, 1H), 1.82 (s, 3H), 1.52 (s, 3H), 1.45 (s, 3H), 1.34 (s, 6H).

(3S,4R,5R,6S)-6-(prop-1-en-2-yl)-tetrahydro-2H-pyran-2,3,4,5-tetrayl tetraacetate (35)

Referring again to Scheme 8, Compound 35 was prepared from Compound 34 (11 mg, 0.04 mmol) following the general procedure for acetonide hydrolysis and peracetylation of Example 10. Yield 81% (11.7 mg, 0.033 mmol)

(3S,4R,5S,6R)-6-((S)-2-methyloxiran-2-yl)-tetrahydro-2H-pyran-2,3,4,5-tetrayl tetraacetate (36)

Referring to Scheme 8, to a mixture of the peracetate (Compound 35) (6 mg, 0.017 mmol) in DCM (1 mL) was added m-CPBA (12 mg, 0.052 mmol) and the mixture was stirred at an ambient temperature for 16 hours. The reaction mixture was aspirated onto 1 mm radial chromatotron plate and eluted with 25% ethyl acetate in hexanes to give 4.6 mg (72%) of the epoxide. LRMS (ESI+) m/z 397 (M+Na)+.

Example 21

Synthesis of propargyl fucose tetraacetate ((3S,4R,5R,6S)-6-(prop-2-ynyl)-tetrahydro-2H-pyran-2,3,4,5-tetrayl tetraacetate) (37)

At −40° C., trifluoromethanesulfonic anhydride (166 μL, 0.98 mmol, 1.5 eq.) was added over 2 min via syringe to a solution of the protected galactose (Compound 2) (170 mg, 0.65 mmol) and 2,6-lutidine (96 μL, 0.82 mmol, 1.25 eq.) in methylene chloride (3 mL). The starting material was consumed in 1 h, and the reaction was quenched with sat. NaHCO$_3$. The mixture was extracted with ether (3×) and the combined organic layers dried (MgSO$_4$), filtered, and concentrated. The crude product was purified by flash chromatography (eluting with 9:1 hexanes-EtOAc) to afford the product as a clear oil. The triflate was immediately used in the next step.

nBuLi (0.70 mL, 1.74 mmol, 2.6 M, 3.8 eq.) was added dropwise to a solution of trimethylsilylacetylene (0.23 mL, 1.61 mmol, 3.5 eq.) and HMPA (85 μL) in THF (1.5 mL) at −60° C. After 15 min of stirring, the triflate (180 mg, 0.46 mmol) was added and the contents stirred while warming to room temperature. After stirring overnight, the reaction was quenched with saturated NH$_4$Cl and the mixture extracted with ether (2×). The combined organic layers were dried and concentrated. By LC/MS partial TMS cleavage occurred. Purification was performed using flash chromatography (eluting with 95:5 to 9:1 hexanes-EtOAc) and both products were collected and concentrated to a clear oil. Overall yield: 61 mg (TMS protected), 68 mg (deprotected), 58% yield. TMS protected data: LRMS (ESI+) m/z 341.1 (M+H)+, 363.1 (M+Na)+. $^1$H-NMR (CDCl$_3$) δ: 0.15 (s, 9H), 1.34 (s, 3H), 1.36 (s, 3H), 1.45 (s, 3H), 1.56 (s, 3H), 2.52 (dd, J=6.4 Hz, 16.8 Hz, 1H), 2.63 (dd, J=8.4 Hz, 16.4 Hz, 1H), 3.91 (dt, J=1.6 Hz, 6.0 Hz, 1H), 4.30 (dd, J=2.4 Hz, 4.8 Hz, 1H), 4.32 (dd, J=2.0 Hz, 8.0 Hz, 1H), 4.62 (dd, J=2.4 Hz, 8.0 Hz, 1H), 5.50 (d, J=5.2 Hz, 1H).

The combined alkynes were deprotected using TFA (1 mL) and water (100 μL) for 2 h. The mixture was concentrated under high vacuum and peracetylated with acetic anhydride (1 mL), pyridine (1 mL), and DMAP (3 mg), for 3 days. The mixture was concentrated and purified by flash chromatography (eluting with 4:1 to 3:2 hexanes-EtOAc). The desired fractions were pooled and concentrated to give the product as a clear sticky solid. Overall yield: 32 mg (51%). LRMS (ESI+) m/z 297.1 (M-OAc)+, 379.0 (M+Na)+.

Example 22

Synthesis of alkynyl fucose tetrapropanoate ((3S,4R,5R)-5-((S)-1-(propionyloxy)prop-2-ynyl)-tetrahydro-furan-2,3,4-triyl tripropionate mixture) (38)

To a mixture of Compound 6 (25 mg, 0.143 mmol) in pyridine was added acid chloride (1 mL, propionyl chloride). The reaction mixture solidified and DCM (2 mL), and DMAP (5 mg) was added and the mixture was stirred overnight at an ambient temperature. The reaction mixture was treated with saturated aqueous sodium bicarbonate with stirring for ~10 min. The reaction mixture was poured into water and extracted with ethyl acetate (3×25 mL). The combined extracts were washed with 1N HCl (20 mL), saturated aqueous sodium bicarbonate (20 mL) and brine before being dried over MgSO$_4$, filtered and concentrated. The resulting residue was purified via radial chromatography on a 1 mm plate eluting with 25% ethyl acetate in hexanes to give a heterogeneous mixture of α and β-pyranose and furanose isomers. Yield: 26.8 mg (47%). LRMS (ESI$^+$) m/z 421 (M+Na+), 325 (M-propionate)$^+$.

Example 23

Synthesis of alkynyl fucose tetra-n-hexanoates (3S, 4R,5R)-5-(S)-1-(hexanoyloxy)prop-2-ynyl)-tetrahydrofuran-2,3,4-triyl trihexanoate and (2S,3S,4R,5R, 6S)-6-ethynyl-tetrahydro-2H-pyran-2,3,4,5-tetrayl tetrahexanoate mixture (39 and 40, respectively); and (2R,3S,4R,5R,6S)-6-ethynyl-tetrahydro-2H-pyran-2, 3,4,5-tetrayl tetrahexanoate (41)

Referring to Scheme 9, to a mixture of Compound 6 (25 mg, 0.143 mmol) in pyridine (1 mL) was added DMAP (~5 mg) and hexanoic anhydride (1 mL). The mixture was stirred overnight at an ambient temperature. The reaction mixture was treated with saturated aqueous sodium bicarbonate with stirring for ~10 min., and the reaction mixture was poured into water and extracted with ethyl acetate (3×25 mL). The combined extracts were washed with 1N HCl (20 mL), saturated aqueous sodium bicarbonate (20 mL) and brine before being dried over MgSO$_4$, filtered and concentrated. The resulting residue was purified via radial chromatography on a 1 mm plate eluting with 25% ethyl acetate hexanes to give to products shown in Scheme 9. (3S,4R,5R)-5-((S)-1-(hexanoyloxy)prop-2-ynyl)-tetrahydrofuran-2,3,4-triyl trihexanoate and (2S,3S,4R,5R,6S)-6-ethynyl-tetrahydro-2H-pyran-2,3, 4,5-tetrayl tetrahexanoate mixture: LRMS (ESI$^+$) m/z 589 (M+Na$^+$). (2R,3S,4R,5R,6S)-6-ethynyl-tetrahydro-2H-pyran-2,3,4,5-tetrayl tetrahexanoate: $^1$H-NMR (CDCl$_3$) δ 5.70 (d, J=8.4 Hz, 1H), 5.52 (dd, J=3.5, 1.2 Hz, 1H), 5.35 (t, J=8.2 Hz, 1H), 5.1 (dd, J=8.2, 3.4 Hz, 1H), 4.60 (dd, J=2.4, 0.6 Hz, 1H), 2.50-1.90 (m, 11H), 1.70-1.50 (m, 9H), 1.19-1.10 (m, 20H), 0.95-0.83 (m, 15H); LRMS (ESI$_+$) m/z 589 (M+Na$_+$).

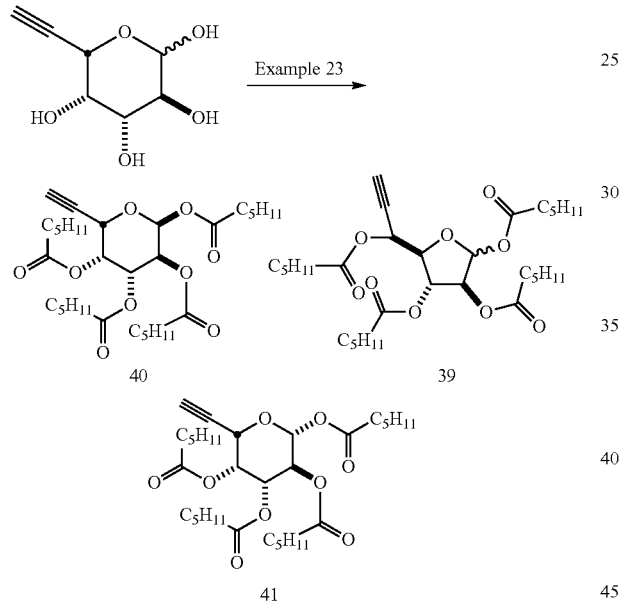

Scheme 9

Example 24

Synthesis of alkynyl fucose tetrakis(trimethylacetate) ((2S,3S,4R,5R)-5-((S)-1-(pentanoyloxy)prop-2-ynyl)-tetrahydrofuran-2,3,4-triyl tripentanoate (42) and (2R,3S,4R,5R)-5-(S)-1-(pentanoyloxy)prop-2-ynyl)-tetrahydrofuran-2,3,4-triyl tripentanoate (43)); alkynyl fucose tris(trimethylacetate) (3S,4R,5R,6S)-6-ethynyl-5-hydroxy-tetrahydro-2H-pyran-2,3,4-triyl tripentanoate mixture (44); and alkynyl fucose bis (trimethylacetate (2R,3S,4R,5R,6S)-6-ethynyl-3,5-dihydroxy-tetrahydro-2H-pyran-2,4-diyl dipentanoate (45))

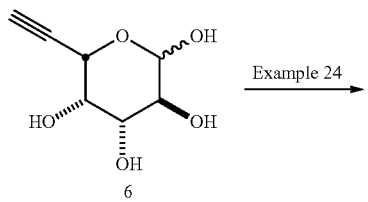

Scheme 10

6

-continued

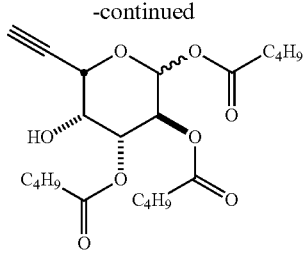

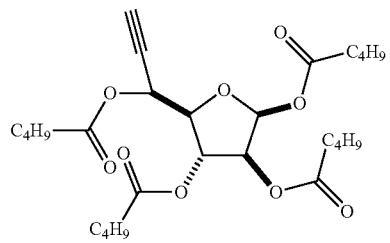

42

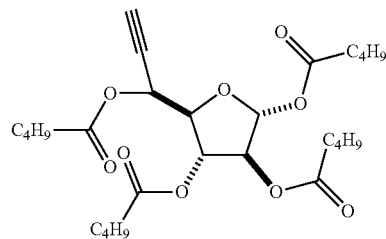

43

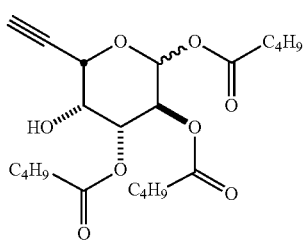

44

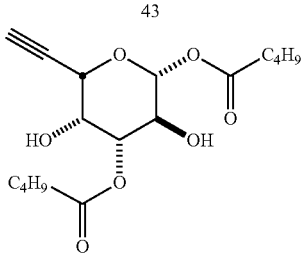

45

To a mixture of Compound 6 (see Example 10: 25 mg, 0.143 mmol) in pyridine (1 mL) was added DMAP (~5 mg) and trimethyl acetic anhydride (1 mL). The mixture was stirred overnight at an ambient temperature. The reaction mixture was treated with saturated aqueous sodium bicarbonate with stirring for ~10 min., and the reaction mixture was poured into water and extracted with ethyl acetate (3×25 mL). The combined extracts were washed with 1N HCl (20 mL), saturated aqueous sodium bicarbonate (20 mL) and brine before being dried over MgSO$_4$, filtered and concentrated. The resulting residue was purified via radial chromatography on a 1 mm plate eluting with 25% ethyl acetate hexanes to give to products shown in Scheme 10.

(2S,3S,4R,5R)-5-((S)-1-(pentanoyloxy)prop-2-ynyl)-tetrahydrofuran-2,3,4-triyltripentanoate: $^1$H-NMR (CDCl$_3$) δ 6.31 (d, J=6.5 Hz, 1H), 5.68 (dd, J=7.0, 5.8 Hz, 1H), 5.54 (dd, J=9.2, 2.4 Hz, 1H), 5.38 (dd, J=7.0, 4.7 Hz, 1H), 4.29 (dd, J=9.2, 5.6 Hz, 1H), 2.4 (d, J=2.3 Hz, 1H), 1.24 (s, 9H), 1.21 (s, 9H), 1.20 (s, 9H), 1.19 (s, 9H); LRMS (ESI$_+$) m/z 533 (M+Na$_+$), 409.

(2R,3S,4R,5R)-5-((S)-1-(pentanoyloxy)prop-2-ynyl)-tetrahydrofuran-2,3,4-triyl tripentanoate: $^1$H-NMR (CDCl$_3$) δ 6.12 (d, J=0.4 Hz, 1H), 5.59 (dd, J=6.8, 2.2 Hz, 1H), 5.35 (dt, J=4.1, 1.5 Hz, 1H), 5.03 (dd, J=1.0, 0.4 Hz, 1H), 2.46 (d, J=2.3 Hz, 1H), 1.24 (s, 9H), 1.24 (s, 9H), 1.23 (s, 9H), 1.22 (s, 3H); LRMS (ESI$^+$) m/z 533 (M+Na$^+$), 409.

(3S,4R,5R,6S)-6-ethynyl-5-hydroxy-tetrahydro-2H-pyran-2,3,4-triyl tripentanoate mixture: LRMS (ESI$^+$) m/z 449 (M+Na$^+$).

(2R,3S,4R,5R,6S)-6-ethynyl-3,5-dihydroxy-tetrahydro-2H-pyran-2,4-diyl dipentanoate: $^1$H-NMR (CDCl$_3$) δ 5.54 (d, J=8.2 Hz, 1H), 4.84 (dd, J=10.0, 3.2 Hz, 1H), 4.52 (dd, J=2.1, 1.1 Hz, 1H), 4.15 (dd, J=3.2, 1.2 Hz, 1H), 4.08 (dd, J=10.0, 8.1 Hz, 1H), 2.58 (d, J=2.2 Hz, 1H), 1.26 (s, 9H), 1.25 (s, 9H); LRMS (ESI$^+$) m/z 365 (M+Na$^+$).

Example 25

Synthesis of (3S,4R,5R,6S)-6-ethynyl-tetrahydro-2H-pyran-2,3,4,5-tetrayl tetrakis(2-methylpropanoate) (46)

Scheme 11

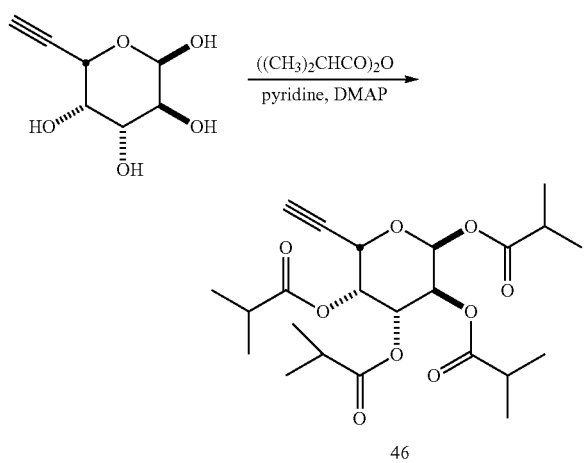

(Followed procedure 2) To a mixture of the tetra-ol (5 mg, 0.028 mmol) in pyridine (0.2 mL) was added DMAP (~1 mg)

and the anhydride (0.2 mL or 200 mg). The mixture was stirred overnight at an ambient temperature and was treated with saturated aqueous sodium bicarbonated with stirring for 10 min. The mixture was poured into water and extracted with ethyl acetate (3×25 mL). The combined extracts were washed with 1N HCl (20 mL), saturated aqueous sodium bicarbonate (20 mL) and brine before being dried over MgSO₄, filtered and concentrated. The resulting residue was purified via radial chromatography on a 1 mm plate eluting with 25% ethyl acetate hexanes to give the product in the α-pyranose form: ¹H-NMR (CDCl₃) δ 6.42 (d, J=3 Hz, 1H), 5.6 (s, 1H), 5.4 (m, 1H), 2.8-2.57 (m, 2H), 2.50-2.38 (m, 3H), 1.30-1.07 (m, 13H), 1.06-1.02 (m, 1H). LRMS (ESI⁺) m/z 477.1 (M+Na⁺).

Example 26

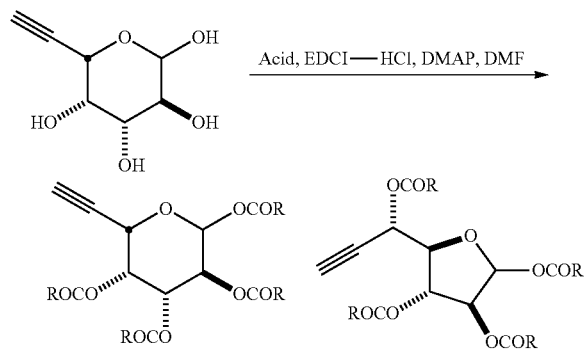

Procedure 3:

To a solution of the tetra-ol (5 mg, 0.028 mmol) in DMF (100 uL) was added nicotinic acid (70 mg, 0.57 mmol), DMAP (0.5 mg) and EDCI-HCl (55 mg, 0.28 mmol). The reaction mixture was stirred at an ambient temperate for 16 h. The mixture was treated with saturated aqueous sodium bicarbonate (5 mL) with stirring for 5 min. The resulting mixture was extracted with ethyl acetate (3×3 mL). The combined extracts were washed with water and brine, dried over MgSO₄, filtered and concentrated under reduced pressure. The mixture was purified via radial chromotography on a 1 mm plate eluting with 5% methanol in methylene chloride. A single major band was collected and concentrated to give the perester.

The following were prepared utilizing the procedure above:

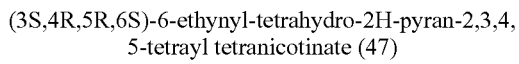

Yield 12.1 mg (72%), LRMS (ESI+) m/z 594.85 (M+H).

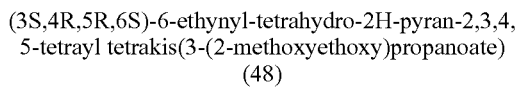

Yield 18.5 mg (95%), LRMS (ESI+) m/z 717 (M+Na)+.

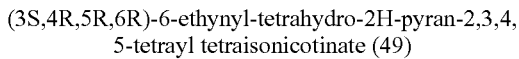

Yield 13.0 mg (78%), LRMS (ESI+) m/z 594 (M+H)+.

Example 27

Preparation of (3S,4R,5R,6S)-6-(benzyloxymethyl) tetrahydro-2H-pyran-2,3,4,5-tetrayl tetraacetate

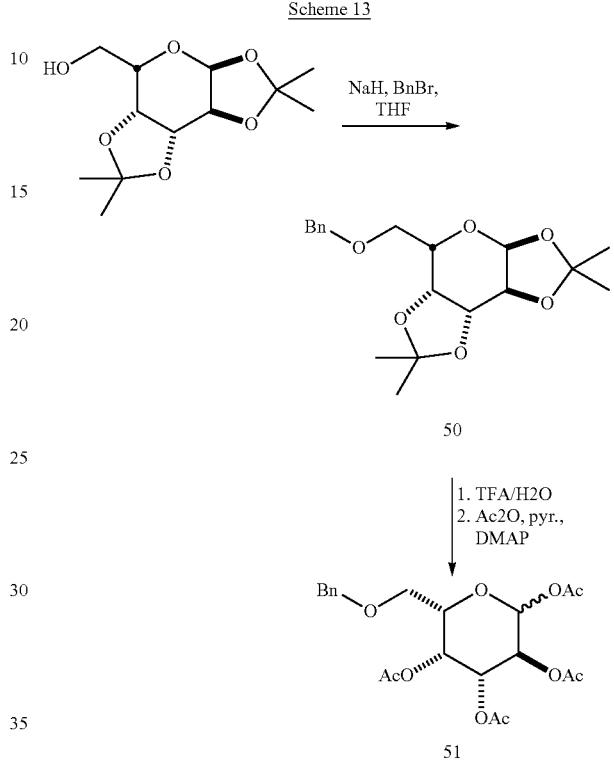

(3aS,5S,5aR,8aR,8bS)-5-(benzyloxymethyl)-2,2,7,7-tetramethyltetrahydro-3aH-bis[1,3]dioxolo[4,5-b:4', 5'-d]pyran (50)

To a mixture of the alcohol (100 mg, 0.38 mmol) and benzyl bromide (83 μL, 0.72 mmol) in THF (2 mL) was added NaH (50 mg of a 60% dispersion in mineral oil) and the reaction mixture was stirred overnight at an ambient temperature. To the mixture was added sat. aq. NH₄Cl (10 mL) and the mixture was extracted with ethyl acetate (3×25 mL). The combined extracts were washed with water and brine and were dried over MgSO₄. Filteration and concentration gave a residue that was purified via radial chromatography on a 1 mm plate, eluting with 10% ethyl acetate in hexanes to give 63 mg (47%): ¹H-NMR (CDCl₃) δ 7.37-7.22 (m, 5H), 5.55 (d, J=4.9 Hz, 1H), 4.64-4.53 (m, 3H), 4.32 (dd, J=5.1, 2.3 Hz, 1H), 4.27 (dd, J=7.8, 2.4 Hz, 1H), 4.01 (dt, J=6.4, 1.9 Hz, 1H), 3.72-3.61 (m, 2H), 1.54 (s, 3H), 1.44 (s, 3H), 1.33 (s, 6H).

(3S,4R,5R,6S)-6-(benzyloxymethyl)tetrahydro-2H-pyran-2,3,4,5-tetrayl tetraacetate (51)

To a round-bottom flask charged with the benzyl ether (63 mg, 0.18 mmol) and cooled to 0° C. was added ice-cold TFA/H2O (9:1, 5 mL). The mixture was stirred for 1 h and was concentrated under reduced pressure. The residue was then treated with pyridine (3 mL), DMAP (5 mg) and acetic anhydride (3 mL). The mixture was stirred 16 h at an ambient temperature and was concentrated under reduced pressure. The residue was purified via radial chromatography on a 2 mm plate eluting with 25% ethyl acetate in hexanes to give the a mixture of pyranose and furanose benzy ether peracetates, 97 mg (0.22 mmol, 122%): LRMS (ESI+) m/z 378.9 (M-OAc)+.

Example 28

Preparation of (2R,3R,4S)-2-((S)-1-acetoxyprop-2-ynyl)-5-methoxy-tetrahydrofuran-3,4-diyl diacetate (52)

Scheme 14

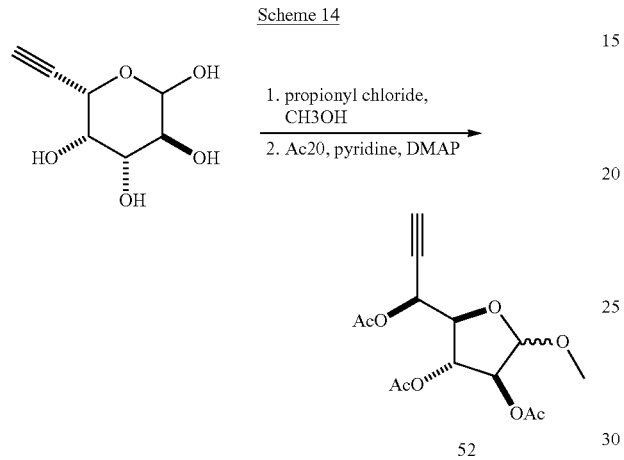

(2R,3R,4S)-2-((S)-1-acetoxyprop-2-ynyl)-5-methoxy-tetrahydrofuran-3,4-diyl diacetate (52):

A round-bottom flask was charged with $CH_3OH$ (2 mL) and propionyl chloride (20 μL) was added. After 5 min, the tetra-ol (~5 mg, 0.028 mmol) was added and the mixture was stirred overnight at an ambient temperature. The mixture was concentrated under reduced pressure, the residue was treated with pyridine (1 mL), DMAP (0.5 mg) and acetic anhydride (1 mL), stirred for ~2 h and concentrated under reduced pressure. The resulting residue was purified by radial chromatography to give a mixture of the two furanose triacetates as an inseparable mixture, 6.1 mg (69%): LRMS (ESI+) m/z 336.95 (M+Na)+.

Example 29

(3S,4R,5S,6R)-6-(difluoromethyl)tetrahydro-2H-pyran-2,3,4,5-tetrayl tetraacetate Scheme 15

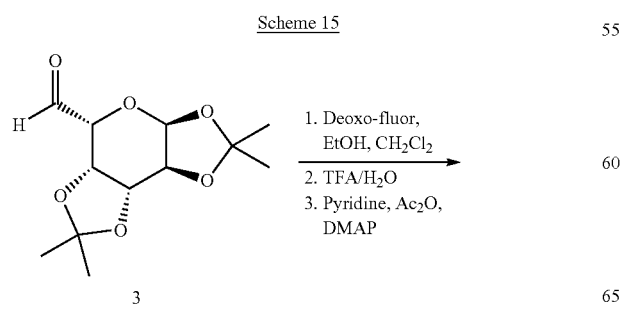

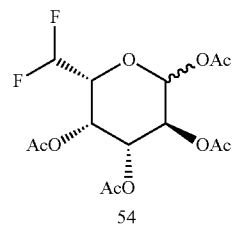

(3aS,5R,5aS,8aR,8bS)-5-(difluoromethyl)-2,2,7,7-tetramethyltetrahydro-3aH-bis[1,3]dioxolo[4,5-b:4',5'-d]pyran (53)

A mixture of the aldehyde (70 mg, 0.23 mmol) and absolute ethanol (3.1 μL, 54 μmol, 0.2 eq.) in methylene chloride (115 μL, 2 M) was treated with his (2-methoxyethyl)aminosulfur trifluoride (Deoxo-fluor, 85 μL, 0.46 mmol, 1.7 eq.) in a sealed Eppendorf tube. The contents stood at 37° C. for 72 h. The reaction was cooled and then purified by flash chromatography (eluting with 9:1 to 4:1 hexanes-EtOAc). The difluoro-diacetonide intermediate was isolated as a clear oil. Yield: 35 mg, 46% yield. $^1$H-NMR (CDCl$_3$) δ: 1.34 (s, 3H), 1.35 (s, 3H), 1.46 (s, 3H), 1.54 (s, 3H), 3.85-3.92 (m, 1H), 4.33-4.38 (m, 2H), 4.62-4.67 (m, 1H), 5.56 (dd, J=2 Hz, 4.8 Hz, 1H), 5.84 (dt, J=6.8 Hz, 54 Hz, 1H).

(3S,4R,5S,6R)-6-(difluoromethyl)tetrahydro-2H-pyran-2,3,4,5-tetrayl tetraacetate (54)

The aforementioned compound (30 mg, 0.11 mmol) was treated with trifluoroacetic acid (1 mL) and water (100 uL) for 2 h. The mixture was concentrated under high vacuum and peracetylated with acetic anhydride (1 mL), pyridine (1 mL), and DMAP (5 mg), for 1 d. The mixture was concentrated and purified by flash chromatography (eluting with 4:1 to 1:1 hexanes-EtOAc). The desired fractions were pooled and concentrated to give the product as a clear sticky solid. Overall yield: 24 mg (62%). LRMS (ESI$^+$) m/z 309 (M-OAc)$^+$, 391 (M+Na)$^+$.

Example 30

Preparation of 2-Fluoro-2-Deoxyfucose Peracetate (58)

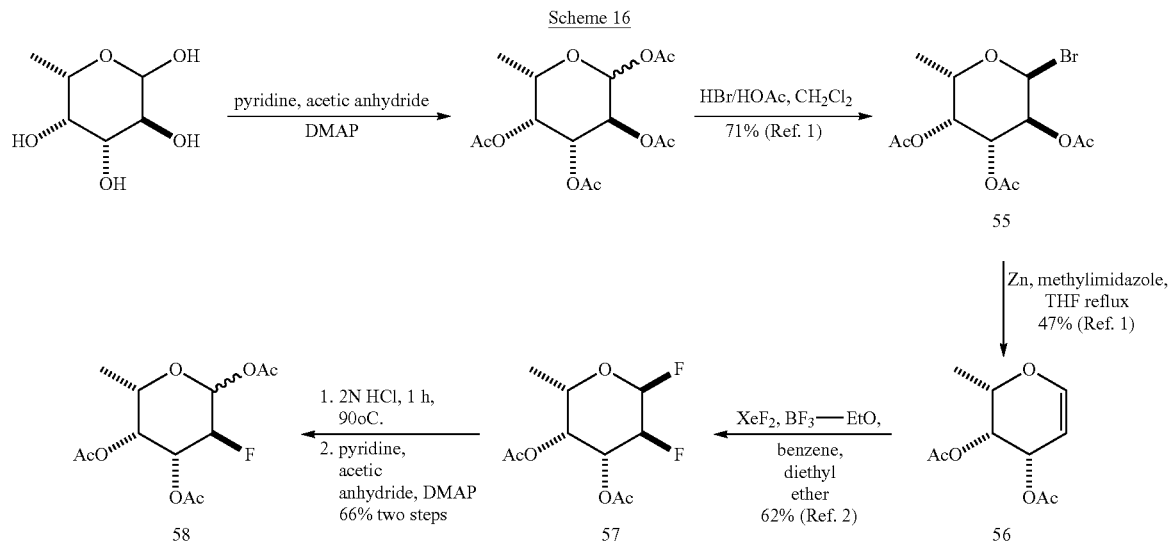

Scheme 16

Compounds 56, 57 and 58 were prepared according to the following references:

1. Oberthur, M.; Leimkuhler, C.; Kuguer, R. G.; Lu, W.; Walsh, C. T.; Kahne, D. *J. Am. Chem. Soc.* 2005, 127, 10747-10752
2. a) Murray, B. W.; Wittmann, V.; Burkhart, M. D.; Hung, S-C.; Wong, C-H. *Biochemistry,* 1997, 36, 823-831. b) Korytnky, W.; Valentekovic-Horvath, S.; Petrie, C. R. *Tetrahedron,* 1982, 38(16), 2547-2550.

Example 31

Preparation of (3S,4R,5R,6S)-6-(propa-1,2-dienyl)-tetrahydro-2H-pyran-2,3,4,5-tetrayl tetraacetate (60)

Scheme 17

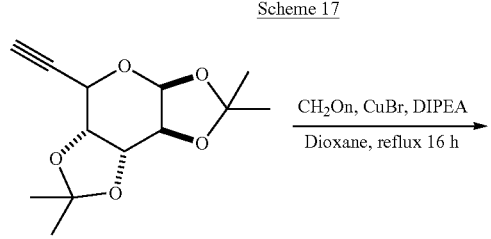

CH$_2$On, CuBr, DIPEA
Dioxane, reflux 16 h

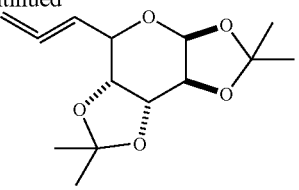

59

1. 10% H$_2$O/TFA
2. Ac$_2$O, Pyridine, DMAP

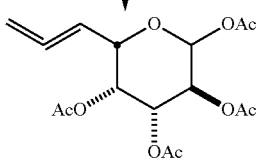

60
+ furanose form

Allenyl diacetonide (59)

To a suspension of alkyne (compound 5, 25 mg, 0.1 mmol), paraformaldehyde (7 mg, 0.215 mmol), CuBr (5 mg, 0.035 mmol) and dioxane (0.5 mL) in a pressure tube was added DIPEA (28 μL, 0.223 mmol). The pressure tube was sealed and the brown mixture was heated at reflux for 16 h then cooled to rt and filtered. The solid was washed with Et$_2$O, and the combined filtrates were concentrated under reduced pressure. Purification by flash chromatography (25% ethyl acetate in hexanes) afforded the desired allene compound 59, 2.3 mg (9%): $^1$H NMR (CDCl$_3$; 400 mHz) δ: 5.56 (d, J=4.0 Hz, 1H), 5.36 (q, J=8.0 Hz, 1H), 4.84 (m, 2H), 4.62 (dd, J=7.8 Hz, 3.4 Hz, 1H), 4.37 (dd, J=8.2 Hz, 1.7 Hz, 1H), 4.32 (d, 1H, J=2.3 Hz, 1H), 1.54 (s, 3H), 1.49 (s, 3H), 1.36 (s, 3H), 1.34 (s, 3H).

To the acetonide (compound 59, 2.3 mg, 8.5 mmol) in a round-bottom flask and cooled in an ice-bath was added ice-cold 10% H$_2$O/TFA (4 mL) and the mixture was stirred for 1 h. After concentration under reduced pressure, the resulting residue was treated with pyridine (2 mL), DMAP (0.5 mg) and acetic anhydride (2 mL). The reaction mixture was stirred overnight and the mixture was concentrated under reduced pressure and purified by radial chromatography on a 1 mm plate eluting with 25% ethyl acetate in hexanes. A single band was collected and concentrated to give 4.1 mg compound 60 as a mixture of anomeric acetates: LRMS (ESI$^+$) m/z 378.98 (M+Na$^+$)

Example 32

Preparation of 2-Fluoro-2-Deoxyfucose Peracetate

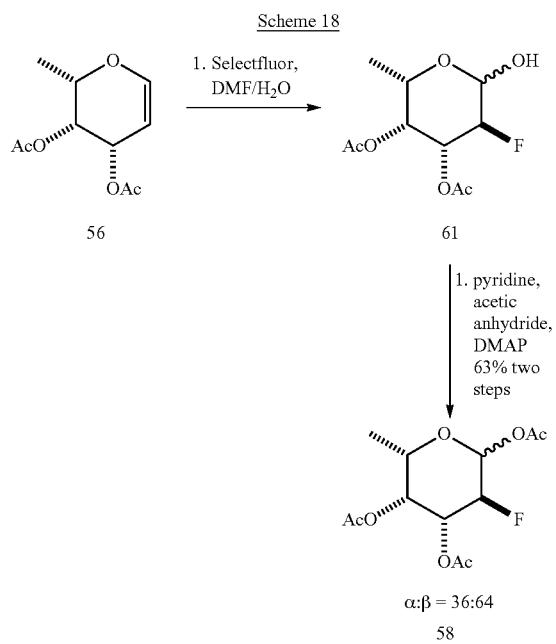

Preparation of 61

To a solution of compound 56 (500 mg, 2.3 mmol) in DMF/H$_2$O (30 mL of a 1:1 mixture) was added Selectfluor® (1.24 g, 3.5 mmol) and the mixture was stirred at an ambient temperature for 12 h. The mixture was diluted with ethyl acetate (100 mL) and washed with water (3×100 mL). The organic layer was dried over Na$_2$SO$_4$, filtered and concentrated under reduced pressure: LRMS (ESI$^+$) m/z 273.04 (M+Na$^+$). See published procedure: Burkart, M. D.; Zhang, Z.; Hung, S-C.; Wong, C-H. *J. Am. Chem. Soc.* 1997, 119, 11743-11746.

(3S,4R,5R,6S)-3-fluoro-6-methyl-tetrahydro-2H-pyran-2,4,5-triyl triacetate (58)

To a mixture of compound 61 in pyridine (10 mL) was added acetic anhydride (10 mL) followed by DMAP (10 mg) and the mixture was stirred for 2 h at an ambient temperature. The mixture was concentrated under reduced pressure, dissolved in DCM (5 mL) and aspirated onto a 2 mm radial chromatotron plate; eluting with 25% ethyl acetate in hexanes. A single band was collected and concentrated to give 420 mg of compound 58 (1.44 mmol, 63%) as an inseparable mixture of anomers (α/β=36.64): $^1$H NMR (CDCl$_3$; 400 mHz) δ (α-anomer): 6.43 (d, J=4.11 Hz, 1H), 5.41 (dt, J=10.8, 3.72 Hz, 1H), 5.37 (m, 1H), 4.88 (ddd, J=49.5, 10.2, 3.9 Hz, 1H), 4.25 (q, 1H, J=6.7 Hz, 1H), 2.9 (s, 3H), 2.07 (s, 3H), 1.15 (d, J=6.5 Hz, 3H); β-anomer: 5.77 (dd, J=8.02, 4.2 Hz, 1H), 5.3 (m, 1H), 5.17 (dq, J=9.8, 3.5 Hz, 1H), 4.64 (ddd, J=51.8, 9.8, 8.0 Hz, 1H), 3.98 (dq, J=6.4 Hz, 1.0 Hz, 1H), 2.18 (s, 3H), 2.07 (s, 3H), 1.22 (d, J=6.2 Hz, 3H); LRMS (ESI$^+$) m/z 315.02 (M+Na$^+$).

Example 33

Preparation of L-2-deoxy-2-chlorofucopyranose-1,3,4-triacetate, 62

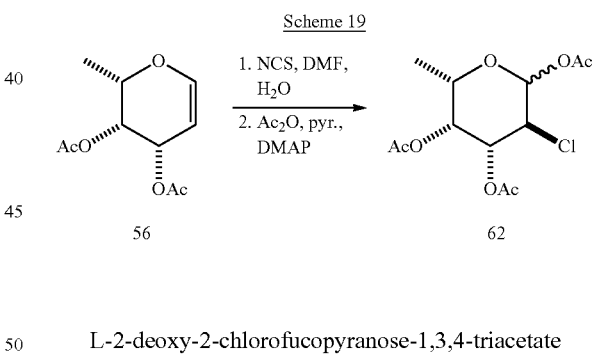

L-2-deoxy-2-chlorofucopyranose-1,3,4-triacetate

To a mixture of the compound 56 (100 mg, 0.47 mmol) in DMF/H$_2$O (2 mL of a 1:1 mixture) was added N-chlorosuccinimide (91 mg, 0.7 mmol) and the mixture was stirred for 16 h at an ambient temperature. The reaction mixture was poured into ethyl acetate (100 mL) and washed with water and brine, dried over MgSO$_4$, filtered and concentrated under reduced pressure. The mixture was taken up in pyridine (2 mL). DMAP (2 mg) was added and acetic anhydride (2 mL) was added. The mixture was stirred for 16 h at an ambient temperature before being concentrated and purified via radial chromatography on a 1 mm plate eluting with 25% ethyl acetate in hexanes to give 98 mg (0.79 mmol, 79%) of the 2-deoxy-2-chlorofucose triacetate 62 as a mixture of anomers (α/β=0.73/1.0) as determined by 1H NMR: LRMS (ESI$^+$) m/z 330.98 (M+Na$^+$).

Example 34

Preparation of (2S,4R,5R,6S)-3,3-difluoro-6-methyl-tetrahydro-2H-pyran-2,4,5-triyl triacetate (65) and (2R,4R,5R,6S)-3,3-difluoro-6-methyl-tetrahydro-2H-pyran-2,4,5-triyl triacetate (66)

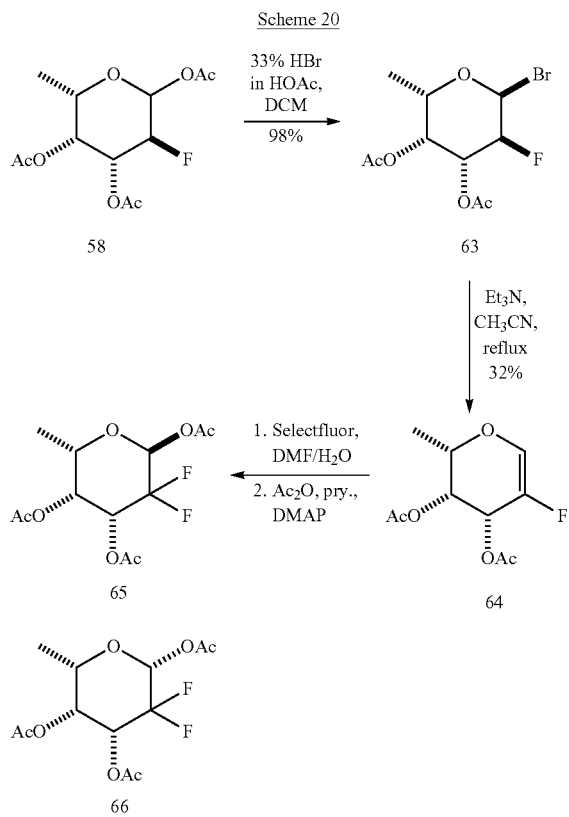

1-α-bromofucopyranose-3,4-diacetate (63)

To the 2-fluorofucose triacetate (compound 58, 300 mg, 1.027 mmol) in CH$_2$Cl$_2$ (1 mL) was added 33% HBr in HOAc (0.25 mL). The mixture was stirred for 2 h and was poured into ice-water (100 mL) and extracted (3×50 mL) with DCM. The combined extracts were washed with water and dried with MgSO$_4$. Filtration and concentration gave 0.313 g (1.0 mmol, 98%) of the L-α-1-bromofucopyranoside-3,4-diacetate (63). The material was carried forward without purification: $^1$H NMR (CDCl$_3$; 400 mHz) δ 6.60 (d, J=4.3 Hz, 1H), 5.48 (dt, J=10.0, 3.5 Hz, 1H), 5.39 (m, 1H), 4.74 (ddd, J=50.5, 10.2, 4.3 Hz, 1H), 4.44 (dq, J=5.9, 1.3 Hz), 2.17 (s, 3H), 2.06 (s, 3H), 1.22 (d, J=6.4 Hz, 3H).

2-fluorofucal-3,4-diacetate, 64

To a mixture of the bromide (63, 312 mg, 1 mmol) in acetonitrile (10 mL) was added Et$_3$N (500 μL, 3 mmol) and the reaction mixture was heated to reflux. The reaction was monitored by TLC. After 2 h, the reaction mixture was poured into ethyl acetate (100 mL) and washed with 1N HCl, water and brine and dried over MgSO$_4$. Filtration and concentration gave a residue that was purified by radial chromatography on a 2 mm plate eluting with 25% ethyl acetate hexanes to give 73 mg (32%): $^1$H NMR (CDCl$_3$; 400 mHz) δ: 6.74 (dd, J=4.9, 1.2 Hz, 1H), 5.97 (dd, J=3.9, 1.2 Hz, 1H), 5.3 (dt, J=5.3, 1.4 Hz, 1H), 4.15 (q, J=6.7 Hz, 1H), 2.18 (s, 3H), 2.07 (s, 3H), 1.56 (s, 3H), 1.22 (d, J=6.5 Hz, 3H).

2-deoxy-2,2-difluorofucopyranose-1,3,4-triacetate (65 and 66)

To a mixture of the fluorofucal (64, 50 mg, 0.216 mmol) in DMF/H$_2$O (1 mL, 1:1 mixture) was added Selectfluor® and the reaction mixture was stirred overnight at an ambient temperature. The reaction mixture was poured into EtOAc (100 mL) and washed with water (3×50 mL) and brine, dried over NaSO$_4$, decanted and concentrated. The resulting residue was acetylated with a mixture of pyridine (1 mL), DMAP (2 mg) and acetic anhydride (1 mL). The mixture was stirred for several hours and concentrated under reduced pressure and purified on a 1 mm radial chromatotron plate eluting with 10% ethyl acetate in hexanes to give a mixture of anomeric 2-deoxy-2,2-difluorofucose-1,3,4-diacetates. α-anomer (65): $^1$H NMR (CDCl$_3$; 400 mHz) δ 6.21 (d, J=7.2, 1H), 5.43 (m, 1H), 5.33 (m, 1H), 4.33 (dq, J=6.5, 0.9 Hz), 2.19 (s, 6H), 2.12 (s, 3H), 1.22 (d, J=6.6 Hz, 3H); LRMS (ESI$^+$) m/z 332.90 (M+Na$^+$). β-anomer (66): $^1$H NMR (CDCl$_3$; 400 mHz) δ 5.78 (d, J=15.5 Hz, 1H), 5.3 (m, 1H), 5.24 (m, 1H), 4.06 (dq, J=6.5, 1.4 Hz), 2.23 (s, 3H), 2.19 (s, 3H), 2.12 (s, 3H), 1.29 (d, J=6.5 Hz, 1H); LRMS (ESI$^+$) m/z 332.99 (M+Na$^+$).

Example 35

Preparation of (2S,4S,5R,6S)-6-methyl-tetrahydro-2H-pyran-2,4,5-triyl triacetate

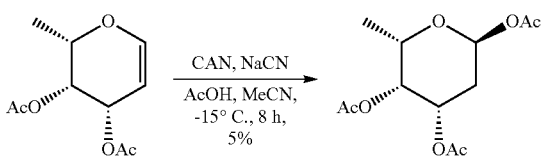

(2S,4S,5R,6S)-6-methyl-tetrahydro-2H-pyran-2,4,5-triyl triacetate

To a flame-dried flask maintained under a nitrogen atmosphere was added fucal-3,4-diacetate (110 mg, 0.51 mmol) dissolved in 2.6 mL of anhydrous acetonitrile. Ceric(IV)ammonium nitrate (727 mg, 1.33 mmol) and glacial acetic acid (290 pt, 5.1 mmol) were added and the reaction mixture was then cooled to −15° C. Sodium cyanide (33 mg, 0.66 mmol) was then added and the reaction was stirred at 15° C. under nitrogen for 8 h. The reaction was quenched with 0.1 M sodium thiosulfate (50 mL). The aqueous layer was extracted with dichloromethane (3×50 mL) and the combined organic layer was washed with brine, dried over sodium sulfate, filtered and concentrated. The residue was purified by flash chromatography on silica gel eluted with a hexane:ethyl acetate solvent mixture (90:10 to 75:25) to provide the title compound (8 mg, 5%). TLC (SiO$_2$, 3:1 hexanes/ethyl acetate): R$_f$=0.20. $^1$H NMR (CDCl$_3$; 400 MHz) δ: 6.29 (m, 1H), 5.29 (ddd, J=12.4, 4.8, 2.8 Hz, 1H), 5.22 (m, 1H), 4.17 (q, J=6.8 Hz, 1H), 2.19 (m, 1H), 2.17 (s, 3H), 2.11 (s, 3H), 2.01 (s, 3H), 1.88 (ddt, J=13.6, 4.8, 1.2, 1H), 1.15 (d, J=6.8 Hz).

Example 35

Activity of Fucose Analogs

The effects of fucose analogs on antibody core fucosylation were tested at concentrations of 50 μM and 1 mM as follows: A CHO DG44 cell line producing a humanized IgG1 anti-CD70 monoclonal antibody, h1F6 (see International Patent Publication WO 06/113909) was cultured at 7.5×10$^5$ cells per mL in 2 mLs of CHO culture media at 37°, 5% CO$_2$ and shaking at 100 RPM in a 6 well tissue culture plate. Media was supplemented with insulin like growth factor (IGF), penicillin, streptomycin and either 1 mM or 50 μM of the fucose analog (prepared as described supra). On day 5 post inoculation, the culture was centrifuged at 13000 RPM for 5 minutes to pellet cells; antibodies were then purified from supernatant.

Antibody purification was performed by applying the conditioned media to protein A resin pre-equilibrated with 1× phosphate buffered saline (PBS), pH 7.4. After washing resin with 20 resin bed volumes of 1×PBS, antibodies were eluted with 5 resin bed volumes of Immunopure IgG elution buffer (Pierce Biotechnology, Rockford, Ill.). A 10% volume of 1M tris pH 8.0 was added to neutralize the eluted fraction. The amount of non-core fucosylated antibody produced was determined as described in Example 7. The results are shown in the following tables.

TABLE 1

| Name (Chemical name) | R$^5$ | R$^1$-R$^4$ | Inhibition at 50 μM | Inhibition at 1 mM |
|---|---|---|---|---|
| Alkynyl fucose (5-ethynylarabinose) | —C≡CH | —OH | >80% | ND |
| Alkynyl fucose peracetate Alkynyl fucose tetraacetate (5-ethynylarabinose tetraacetate) | —C≡CH | —OAc | >80% | >80% |
| 5-propynyl fucose tetraacetate (5-propynylarabinose tetraacetate) | —C≡CCH$_3$ | —OAc | 50% | >80% |
| propargyl fucose tetraacetate ((3S,4R,5R,6S)-6-(prop-2-ynyl)-tetrahydro-2H-pyran-2,3,4,5-tetrayl tetraacetate) | —CH$_2$C≡CH | —OAc | ~10% | ~10-20% |
| Peracetyl galactose (galactose pentaacetate) | —OAc | —OAc | ~0% | ~0% |
| 5-vinyl fucose tetraacetate (5-ethylenylarabinose tetraacetate) | —CHCH$_2$ | —OAc | ~0% | ~4% |
| 6-cyano fucose tetraacetate (6-cyanofucose tetraacetate) | —CH$_2$CN | —OAc | 30% | >80% |
| 5-cyano fucose tetraacetate (pyranose form) (5-cyanoarabinopyranose tetraacetate) | —CN | —OAc | 20% | ND |
| 5-cyano fucose tetraacetate (furanose form) (5-cyanoarabinofuranose tetraacetate) | —CN | —OAc | 5-10% | ND |
| 5-methylester fucose tetraacetate (5-carboxymethyl arabinose tetraacetate) | —C(O)OCH$_3$ | —OAc | 30% | >80% |
| 5-(CH(OAc)CH$_3$) peracetyl fucose (6-methylgalactose pentaacetate) | ~CH(OAc)CH$_3$ | —OAc | ~0% | 40% |
| 5-methyloxiran-arabinose tetraacetate ((3S,4R,5S,6R)-6-((S)-2-methyloxiran-2-yl)-tetrahydro-2H-pyran-2,3,4,5-tetrayl tetraacetate) | (S)-2-methyloxiran-2-yl | —OAc | ~0% | ~35-40% |
| 6-iodo-fucose tetraacetate (6-iodofucose tetraacetate) | —CH$_2$I | —OAc | 3% | 30% |
| 6-chloro-fucose tetraacetate (6-chlorofucose tetraacetate) | —CH$_2$Cl | —OAc | 20% | 20-30% |
| 6-bromo-fucose tetraacetate (6-bromofucose tetraacetate) | —CH$_2$Br | —OAc | 50% | 80% |
| Alkynyl fucose tetrapropanonate (5-ethynylarabinose tetrapropanoate) | —C≡CH | —OC(O)CH$_2$—CH$_3$ | >80% | >80% |
| Alkynyl fucose tetra-n-hexanoate | —C≡CH | —OC(O)(CH$_2$)$_4$—CH$_3$ | >80% | >80% |

TABLE 1-continued

| Name (Chemical name) | $R^5$ | $R^1$-$R^4$ | Inhibition at 50 μM | Inhibition at 1 mM |
|---|---|---|---|---|
| Alkynyl fucose tetrakis(trimethylacetate) (5-ethynylarabinose tetrahexanoate) | —C≡CH | —OC(O)C(CH$_3$)$_3$ | 20% | 60% |
| Alkynyl fucose tetrakis(trimethylacetate) (5-ethynylarabinose tetra(trimethylacetate)) | —C≡CH | —OC(O)C(CH$_3$)$_3$ | 5% | 10% |
| Alkynyl fucose 1, 2, 3-(trimethylacetate) (5-ethynylarabinose 1, 2, 3-(trimethylacetate)) | —C≡CH | —OC(O)C(CH$_3$)$_3$ and —OH | ~0% | ND |
| Alkynyl fucose di(trimethylacetate) (5-ethynylarabinose 1, 3-(trimethylacetate)) | —C≡CH | —OC(O)C(CH$_3$)$_3$ and —OH | >80% | ND |
| Alkynyl fucose pernicotinate | —C≡CH | —C(O)-3-pyridyl | >80% | >80% |
| Alkynyl fucose perisonicotinate | —C≡CH | —C(O)-4-pyridyl | >80% | >80% |
| Alkynyl fucose per-PEG ester | —C≡CH | —C(O)—(CH$_2$CH$_2$O)$_2$—OCH$_3$ | >80% | >80% |
| 1-methyl-2,3,4-triacetyl alkynyl fucose | —C≡CH | $R^1$ = OCH$_3$ $R^2$, $R^3$, $R^4$ = OAc | 68% | >80% |
| Alkynyl fucose perisobutanoate | —Cl≡CH | —OC(O)CH(CH$_3$)$_2$ | >80% | >80% |

"ND" means non-core fucosylated antibody was not detected due to poor antibody production or inhibition of cell growth in the presence of the fucose analog.

TABLE 2

| Name (Chemical name) | $R^5$ | $R^1$ | $R^2/R^{2a}$ | $R^3/R^{3a}$ | Inhibition at 50 μM | Inhibition at 1 mM |
|---|---|---|---|---|---|---|
| 2-deoxy-2-fluorofucose diacetate ($R^4$ = OAc) | —CH$_3$ | —OH | —F/—H | —OAc/—H | >80% | >80% |
| 2-deoxy-2-chlorofucose triacetate ($R^4$ = OAc) | —CH$_3$ | —OAc | —Cl/—H | —OAc/—H | 17% | >80% |
| Allene ($R^4$ = OAc) | —CH=C=CH$_2$ | —OAc | —OAc/—H | —OAc/—H | 23% | 34% |
| 2-deoxy-2-fluorofucose ($R^4$ = OH) | —CH$_3$ | —OH | —F/—H | —OH/—H | >80% | >80% |
| 2-deoxy-2-fluorofucose peracetate ($R^4$ = OAc) | —CH$_3$ | —OAc | —F/—H | —OAc/—H | >80% | >80% |
| 1,2-difluoro-1,2-didexoy fucose peracetate ($R^4$ = OAc) | —CH$_3$ | —F | —F/—H | —OAc/—H | >80% | >80% |
| 6,6-difluorofucose tetraacetate ($R^4$ = OAc) | —CHF$_2$ | —OAc | —OAc/—H | —OAc/—H | >80% | >80% |
| 2-deoxy-2,2-difluorofucopyranose triacetate (alpha) ($R^4$ = OAc) | —CH$_3$ | —OAc | —F/—F | —OAc/—H | 0 | 64% |
| 2-deoxy-2,2-difluorofucopyranose triacetate (beta) ($R^4$ = OAc) | —CH$_3$ | —OAc | —F/—F | —OAc/—H | 0 | 75% |
| 6-methyl-tetrahydro-2H-pyran-2,4,5-triyl triacetate ($R^4$ = OAc) | —CH$_3$ | —OAc | —H/—H | —OAc/—H | 0 | 36% |
| 5-Benzyloxy fucose peracetate ($R^4$ = OAc) | —CH$_2$OCH$_2$Ph | —OAc | —OAc/—H | —OAc/—H | 0 | 75% |

"ND" means non-core fucosylated antibody was not detected due to poor antibody production or inhibition of cell growth in the presence of the fucose analog.

Certain other fucose analogs were tested for their ability to be incorporated into antibodies. These fucose analogs were tested at concentrations of 50 μM and 1 mM using the methodology as described above and in Example 7. The results are shown in the following table.

TABLE 3

| Name (Chemical name) | $R^5$ | $R^1$-$R^4$ | % Incorporation |
|---|---|---|---|
| Propargyl fucose or (3S,4R,5R)-6-(prop-2-ynyl)tetrahydro-2H-pyran-2,3,4,5-tetrayl tetraacetate | (alkyne) | —OAc | 80% (1 mM) |
| 5-(Z)-propenyl fucose peracetate | (Z-propenyl) | —OAc | ~30% |
| Isopropenyl peracetyl fucose or (3S,4R,5R,6S)-6-(prop-1-en-2-yl)-tetrahydro-2H-pyran-2,3,4,5-tetrayl tetraacetate | (isopropenyl) | —OAc | >80% (1 mM and 50 uM) |
| 5-ethyl fucose or (3S,4R,5S,6S)-6-ethyl-tetrahydro-2H-pyran-2,3,4,5-tetraol | —CH$_3$CH$_2$ | —OH | >80% (1 mM and 50 uM) |
| 5-ethyl fucose peracetate or (3S,4R,5S,6S)-6-ethyl-tetrahydro-2H-pyran-2,3,4,5-tetrayl tetraacetate | —CH$_3$CH$_2$ | —OAc | >90% (1 mM and 50 uM) |
| 5-cyclopropyl fucose or (3S,4R,5S,6S)-6-cyclopropyltetrahydro-2H-pyran-2,3,4,5-tetraol | (cyclopropyl) | —OH | ~80% |
| 5-cyclopropyl fucose peracetate or (3S,4R,5R,6S)-6-cyclopropyltetrahydro-2H-pyran-2,3,4,5-tetrayl tetraacetate | (cyclopropyl) | —OAc | ~80% |
| 5-propyloxyarabinose tetraacetate or (3S,4R,5S,6R)-6-((S)-2-methyloxiran-2-yl)tetrahydro-2H-pyran-2,3,4,5-tetrayl tetraacetate | (methyloxiranyl) | —OAc | ~60% |
| Fluoromethylene fucose or (3S,4R,5S)-6-(fluoromethyl)tetrahydro-2H-pyran-2,3,4,5-tetrayl tetraacetate | —CH$_2$F | —OAc | >90% (1 mM and 50 uM) |
| 5-chloromethylene peracetyl fucose or (3S,4R,5S)-6-(chloromethyl)tetrahydro-2H-pyran-2,3,4,5-tetrayl tetraacetate | —CH$_2$Cl | —OAc | ~80% |
| 5-bromomethylene peracetyl fucose or (3S,4R,5S)-6-(bromomethyl)tetrahydro-2H-pyran-2,3,4,5-tetrayl tetraacetate | —CH$_2$Br | —OAc | ~50% (50 uM; 20% at 1 mM) |
| 5-iomethylene-peracetyl fucose or (3S,4R,5S)-6-(iodomethyl)tetrahydro-2H-pyran-2,3,4,5-tetrayl tetraacetate | —CH$_2$I | —OAc | ~30% |
| Azido peracetyl fucose or (3S,4R,5R)-6-(azidomethyl)tetrahydro-2H-pyran-2,3,4,5-tetrayl tetraacetate | —CH$_2$N$_3$ | —OAc | 60% |
| 5-(2-azidoethyl) arabinose tetraacetate or (3S,4R,5R,6S)-6-(2-azidoethyl)tetrahydro-2H-pyran-2,3,4,5-tetrayl tetraacetate | —CH$_2$CH$_2$N$_3$ | —OAc | 20% |
| | —CH=C=CH$_2$ | —OAc | ~30% |
| Isopropyl peracetyl fucose or (3S,4R,5R,6S)-6-isopropyltetrahydro-2H-pyran-2,3,4,5-tetrayl tetraacetate | Isopropyl | —OAc | Not detected |

Example 36

Titration Method to Determine Effective Levels of Fucose Analogs

A CHO DG44 cell line producing a humanized IgG1 anti-CD70 monoclonal antibody, h1F6 (see International Patent Publication WO 06/113909) was cultured at 3.0×10$^5$ cells per mL in 30 mLs of CHO culture media at 37°, 5% CO$_2$ and shaking at 100 RPM in a 125 mL shake flask. Media was supplemented with insulin like growth factor (IGF), penicillin, streptomycin and either 100 μM, 50 μM, 5 μM, 500 nM, or 50 nM alkynyl fucose peracetate. Cultures were fed on day 3 with 2% volume of a feed media containing 5 mM, 2.5 mM, 250 μM, 25 μM, and 2.5 μM alkynyl fucose peracetate for the respective cultures. On day four, the culture was split 1:4 into fresh culture media. Cultures were fed with a 6% volume of production feed media containing 1.66 mM, 833 μM, 83 μM, 8.3 μM and 833 nM alkynyl fucose peracetate, respectively, on days 5, 7, 9 and 10. Supplementation of the feed media is optional. Conditioned media was collected on day 13 by passing culture through a 0.2 μm filter.

Antibody purification was performed by applying the conditioned media to a protein A column pre-equilibrated with 1× phosphate buffered saline (PBS), pH 7.4. After washing the column with 20 column volumes of 1×PBS, antibodies were eluted with 5 column volumes of Immunopure IgG elution buffer (Pierce Biotechnology, Rockford, Ill.). A 10% volume of 1M tris pH 8.0 was added to eluted fraction. The sample was dialyzed overnight into 1×PBS. The carbohydrate composition was determined using capillary electrophoresis.

Figure 6:
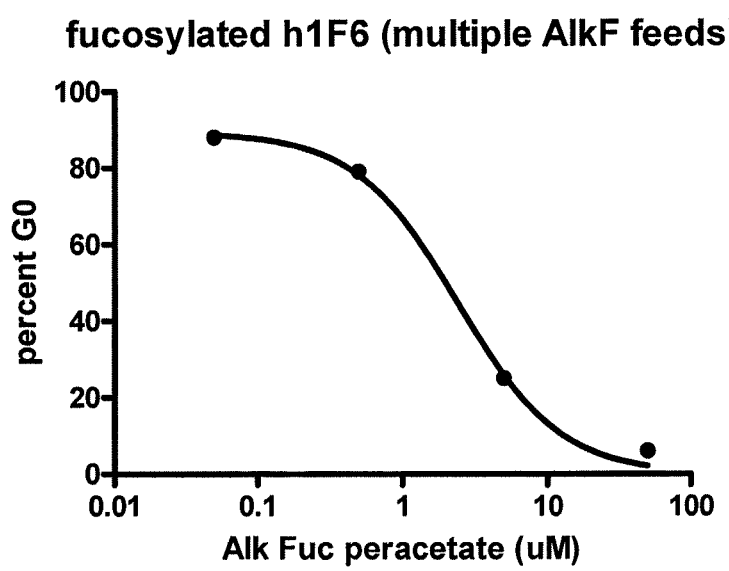
FIG. 6 shows the results of a titration of alkynyl fucose peracetate ("Alk Fuc peracetate") on a culture of host cells expressing h1F6 antibody and the effect on production of Ab with core fucosylation (G0).

Referring to FIG. 6, the results of a titration of alkynyl fucose peracetate ("Alk Fuc peracetate") on a culture of host cells expressing h1F6 antibody and the effect on production of Ab with core fucosylation (G0). As the amount of G0 antibody produced decreased, the amount of non-core-fucosylated antibody increased.

Example 37

Non-Core Fucosylated Antibody Production in Different Culture Media

To determine the effect of different culture media on non-core fucosylated antibody production, a CHO DG44 cell line producing a humanized IgG1 anti-CD70 monoclonal antibody, h1F6 (see International Patent Publication WO 06/113909), was cultured in various media. The cells (7.5× $10^5$ cells per mL in 2 mLs) were cultured in PowerCHO (Lonza Group Ltd., Basil, Switzerland) or OptiCHO (Invitrogen, Carlsbad, Calif.) media CHO culture media at 37°, 5% $CO_2$ and shaking at 100 RPM in a 6 well tissue culture plate. Media was supplemented with insulin like growth factor (IGF), penicillin, streptomycin and 50 μM alkynyl fucose peracetate. On day 5 post-inoculation, the culture was centrifuged at 13000 RPM for 5 minutes to pellet cells; antibodies were then purified from supernatant.

Antibody purification was performed by applying the conditioned media to protein A resin pre-equilibrated with 1× phosphate buffered saline (PBS), pH 7.4. After washing resin with 20 resin bed volumes of 1×PBS, antibodies were eluted with 5 resin bed volumes of Immunopure IgG elution buffer (Pierce Biotechnology, Rockford, Ill.). A 10% volume of 1M tris pH 8.0 was added to neutralize the eluted fraction. Production of non-core fucosylated antibody was determined as described in Example 7. The proportion of non-core fucosylated to core fucosylated antibody produced from each media was similar.

The present invention is not limited in scope by the specific embodiments described herein. Various modifications of the invention in addition to those described herein will become apparent to those skilled in the art from the foregoing description and accompanying figures. Such modifications are intended to fall within the scope of the appended claims. Unless otherwise apparent from the context any step, element, embodiment, feature or aspect of the invention can be used in combination with any other. All patent filings, and scientific publications, accession numbers and the like referred to in this application are hereby incorporated by reference in their entirety for all purposes to the same extent as if so individually denoted.

What is claimed is:

1. A mammalian cell culture medium for the production of antibodies or antibody derivatives having reduced core fucosylation, comprising an effective amount of a fucose analog, wherein the fucose analog is selected from the group consisting of one of the following formulae (III) or (IV):

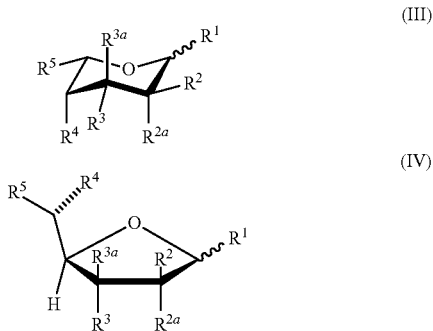

or a biologically acceptable salt or solvate thereof, wherein each of formula (III) or (IV) can be the alpha or beta anomer or the corresponding aldose form;

each of $R^1$-$R^4$ is independently selected from the group consisting of fluoro, chloro, —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene (aryl), —OC(O)$C_2$-$C_{10}$ alkynyl(aryl), —OC(O)$C_1$-$C_{10}$ alkylene heterocycle, —OC(O)$C_2$-$C_{10}$ alkenylene(heterocycle), —OC(O)$C_2$-$C_{10}$ alkynyl heterocycle, —OCH$_2$OC(O) alkyl, —OCH$_2$OC(O)O alkyl, —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O (CH$_2$CH$_2$O)$_n$CH$_3$, —O-tri-$C_1$-$C_3$ alkylsilyl and —OC$_1$-$C_{10}$ alkyl, wherein each n is an integer independently selected from 0-5; and each of $R^{2a}$ and $R^{3a}$ is independently selected from the group consisting of H, F and Cl;

$R^5$ is selected from the group consisting of —CH$_3$, —CHF$_2$, —CH=C=CH$_2$, —C≡CH, —C≡CCH$_3$, —CH$_2$C≡CH, —C(O)OCH$_3$, —CH(OAc)CH$_3$, —CN, —CH$_2$CN, —CH$_2$X (wherein X is Br, Cl or I), and methoxiran;

wherein when $R^5$ is other than —CH=C=CH$_2$ or —CHF$_2$, at least one of $R^1$, $R^2$, $R^3$, $R^{2a}$ and $R^{3a}$ is fluoro or chloro.

2. The culture medium of claim 1 wherein each of $R^1$—$R^4$ is independently selected from the group consisting of fluoro, chloro, —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkynyl (aryl), —OC(O)$C_1$-$C_{10}$ alkylene heterocycle, —OC(O)$C_2$-$C_{10}$ alkenylene(heterocycle), —OC(O)$C_2$-$C_{10}$ alkynyl heterocycle, —OCH$_2$OC(O) alkyl, —OCH$_2$OC(O)O alkyl, —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$—O—(CH$_2$CH$_2$O)$_n$CH$_3$, —O-tri-$C_1$-$C_3$ alkylsilyl and —OC$_1$-$C_{10}$ alkyl, wherein each n is an integer independently selected from 0-5; and at least one of $R^1$, $R^2$, $R^3$, $R^{2a}$ and $R^{3a}$ is fluoro or chloro.

3. The culture medium of claim 1, which:
(i) is free of added animal protein;
(ii) is free of serum;
(iii) is free of added fucose; and
(iv) is a powder or a liquid.

4. The culture medium of claim 2, which:
(i) is free of added animal protein;
(ii) is free of serum;
(iii) is free of added fucose; and
(iv) is a powder or a liquid.

5. The culture medium of claim 3, wherein at least one of $R^1$, $R^2$, $R^{2a}$, $R^3$ and $R^{3a}$ is fluoro.

6. The culture medium of claim 3, wherein two of $R^1$, $R^2$, $R^{2a}$, $R^3$ and $R^{3a}$ are fluoro or chloro.

7. The culture medium of claim 3 wherein the effective amount is an amount of the analog that is sufficient to decrease fucose incorporation into a complex N-glycoside-linked sugar chain of an antibody or antibody derivative by at least 90%.

8. The culture medium of claim 7, wherein $R^1$, $R^3$ and $R^4$ are each independently selected from —OH and —OAc; $R^2$ is F; $R^{2a}$ and $R^{3a}$ are each H; and $R^5$ is —CH$_3$.

9. The culture medium of claim 3, wherein the fucose analog is 2-deoxy-2-fluorofucose diacetate, 2-deoxy-2-chlorofucose triacetate, 2-deoxy-2-fluorofucose, 2-deoxy-2-fluorofucose peracetate, 1,2-difluoro-1,2-didexoy fucose peracetate, or 6,6-difluorofucose tetraacetate.

10. The culture medium of claim 3, wherein the fucose analog is 2-deoxy-2-fluorofucose diacetate or 2-deoxy-2-chlorofucose triacetate.

11. The culture medium of claim 3, wherein the fucose analog is 2-deoxy-2-fluorofucose.

12. The culture medium of claim 11, wherein the effective amount is an amount of the analog that is sufficient to decrease fucose incorporation into a complex N-glycoside-linked sugar chain of an antibody or antibody derivative by at least 80%.

13. The culture medium of claim 12, which is free of added fucose.

14. The culture medium of claim 1 wherein the antibody or antibody derivative is a humanized or human antibody or antibody derivative.

15. The culture medium of claim 1 wherein the mammalian cell culture medium is a Chinese hamster ovary cell culture medium.

16. The culture medium of claim 2 wherein the antibody or antibody derivative is a humanized or human antibody or antibody derivative.

17. The culture medium of claim 2 wherein the mammalian cell culture medium is a Chinese hamster ovary cell culture medium.

18. The culture medium of claim 7 wherein the antibody or antibody derivative is a humanized or human antibody or antibody derivative.

19. The culture medium of claim 7 wherein the mammalian cell culture medium is a Chinese hamster ovary cell culture medium.

20. The culture medium of claim 8 wherein the antibody or antibody derivative is a humanized or human antibody or antibody derivative.

21. The culture medium of claim 8 wherein the mammalian cell culture medium is a Chinese hamster ovary cell culture medium.

22. The culture medium of claim 11 wherein the antibody or antibody derivative is a humanized or human antibody or antibody derivative.

23. The culture medium of claim 11 wherein the mammalian cell culture medium is a Chinese hamster ovary cell culture medium.

24. The culture medium of claim 12 wherein the antibody or antibody derivative is a humanized or human antibody or antibody derivative.

25. The culture medium of claim 12 wherein the mammalian cell culture medium is a Chinese hamster ovary cell culture medium.

26. The culture medium of claim 13 wherein the antibody or antibody derivative is a humanized or human antibody or antibody derivative.

27. The culture medium of claim 13 wherein the mammalian cell culture medium is a Chinese hamster ovary cell culture medium.

* * * * *